(12) United States Patent
Xing et al.

(10) Patent No.: US 9,476,087 B2
(45) Date of Patent: Oct. 25, 2016

(54) METHODS AND COMPOUNDS FOR DETECTING BETA-LACTAMASE ACTIVITY

(71) Applicant: Nanyang Technological University, Singapore (SG)

(72) Inventors: Bengang Xing, Singapore (SG); Xianfeng Huang, Singapore (SG); Tingting Jiang, Singapore (SG); Rongrong Liu, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 14/326,215

(22) Filed: Jul. 8, 2014

(65) Prior Publication Data

US 2014/0322739 A1 Oct. 30, 2014

Related U.S. Application Data

(62) Division of application No. 12/113,109, filed on Apr. 30, 2008, now Pat. No. 8,802,387.

(51) Int. Cl.

| | | |
|---|---|---|
| *C12Q 1/34* | (2006.01) | |
| *C07D 501/04* | (2006.01) | |
| *C07D 501/18* | (2006.01) | |
| *C07D 501/16* | (2006.01) | |
| *C07D 519/06* | (2006.01) | |

(52) U.S. Cl.
CPC ............. *C12Q 1/34* (2013.01); *C07D 501/04* (2013.01); *C07D 501/16* (2013.01); *C07D 501/18* (2013.01); *C07D 519/06* (2013.01); *G01N 2333/986* (2013.01)

(58) Field of Classification Search
CPC .... C07D 501/04; C07D 501/18; C12Q 1/34; G01N 2333/986
USPC .................. 435/18, 6.16; 540/310, 347, 225
See application file for complete search history.

(56) References Cited

U.S. PATENT DOCUMENTS

| 4,264,595 A | 4/1981 | Numata et al. |
| 5,641,623 A | 6/1997 | Martin |
| 8,278,561 B2 | 10/2012 | Kamata et al. |
| 2007/0224273 A1* | 9/2007 | Xu et al. ............. A61K 9/0014 424/488 |

OTHER PUBLICATIONS

Liu et al. (Angewandte Chemie, International Edition (2008) 47(17), 3081.*
Allenmark, "Chiroptical Methods in the Stereochemical Analysis of Natural Products," *Natural Product Reports* 17:145-155, 2000.
Asano et al., "An Alkaline D-Stereospecific Endopeptidase with β-Lactamase Activity from *Bacillus cereus*," *J. Biol. Chem.* 271(47):30256-30262, 1996.
Bush et al., "A Functional Classification Scheme for β-Lactamases and Its Correlation with Molecular Structure," *Antimicrob. Agents Chemother.* 39:1211-1233, 1995.
Bush, "Extended-Spectrum β-Lactamases in North America, 1987-2006," *Clin. Microbiol. Infect.* 14(Suppl. 1):134-143, 2008.
Buynak, "Understanding the Longevity of the β-Lactam Antibiotics and of Antibiotic/β-Lactamase Inhibitor Combinations," *Biochemical Pharmacology* 71:930-940, 2006.
Cantón et al., "Prevalence and Spread of Extended-Spectrum β-Lactamase-Producing Enterobacteriaceae in Europe," *Clin. Microbiol. Infect.* 14(Suppl. 1):144-153, 2008.
De Vlaminck et al., "Local Electrical Detection of Single Nanoparticle Plasmon Resonance," *Nano Letters* 7(3):703-706, 2007.
Fisher et al., "Bacteria Resistance to β-Lactam Antibiotics: Compelling Opportunism, Compelling Opportunity," *Chem. Rev.* 105:395-424, 2005.
Gao et al., "Novel Fluorogenic Substrates for Imaging β-Lactamase Gene Expression" *J. Am. Chem. Soc.* 125:11146-11147, 2003.
Gniadkowski, "Evolution of Extended-Spectrum β-Lactamases by Mutation," *Clin. Microbiol. Infect.* 14(Suppl 1.):11-32, 2008.
Greaves et al., "Protic Ionic Liquids: Properties and Applications," *Chem. Rev.* 108:206-237, 2008.
Guarise et al., "Gold Nanoparticles-Based Protease Assay," *Proc. Natl. Acad. Sci. USA* 103: 3978-3982, 2006.
Hafner, "Gold Nanoparticles are Shaped for Effect," *Laser Focus World* 42:99-101, Apr. 2006.
Hakimelahi et al., "Carbapenem-Based Prodrugs. Design, Synthesis, and Biological Evaluation of Carbapenems," *European Journal of Medicinal Chemistry* 40(4):339-349, 2005.
Harper et al., "Stereochemical Analysis by Solid-State NMR: Structural Predictions in Ambuic Acid," *J. Org. Chem.* 68:4609-4614, 2003.
Härtling et al., "Photochemical Turning of Plasmon Resonances in Single Gold Nanoparticles," *Journal of Physical Chemistry C* 112(13):4920-4924, 2008.
Hiep et al., "Label-Free Detection of Melittin Binding to a Membrane Using Electrochemical-Localized Surface Plasmon Resonance," *Analytical Chemistry* 80(6):1859-1864, 2008.
Homola, "Present and Future of Surface Plasmon Resonance Biosensors," *Anal Bioanal Chem.* 377:528-539, 2003.

(Continued)

*Primary Examiner* — Janet Epps-Smith
(74) *Attorney, Agent, or Firm* — Seed IP Law Group LLP

(57) ABSTRACT

The present invention relates to compounds for and a method of detecting beta-lactamase activity in a sample. The sample is contacted with a nanoparticulate tag. The nanoparticulate tag comprises a metal or a combination of metals, or it comprises a nanotube of a metal, boron nitride and/or carbon. The respective metal is capable of forming one of a covalent bond, a coordinative bond and a non-covalent interaction with a thio or a seleno group. The sample is contacted with a compound of one of general formulas (I)-(III) and (VII)-(IX). At least one beta-lactam moiety of the compound is cleaved by the beta-lactamase activity in the sample. As a result a cleavage moiety Z-A-Z, Z-A-Z—$R^{15}$, Z-A-Z—$R^{16}$, Z-A-Z—$R^{17}$, Z-A-Z—$R^{18}$ or Z-G-N($R^8$) $R^9$ is released that is immobilized on the surface of the nanoparticulate tag by a covalent bond via a Z atom. The presence of beta-lactamase activity is determined based on the presence of the cleavage moiety immobilized onto the surface of the nanoparticulate tag.

16 Claims, 26 Drawing Sheets

(56) References Cited

OTHER PUBLICATIONS

Ishigami et al., "Properties of Boron Nitride Nanotubes," *Scanning Tunneling Microscopy/Spectroscopy and Related Techniques: 12 International Conference, CP696* edited by P.M. Koenraad and M. Kemerink, 94-99, 2003.
Jacoby, "β-Lactamase Nomenclature," *Antimicrob. Agents Chemother.* 50(4):1123-1129, 2006.
Jin et al., "What Controls the Melting Properties of DNA-Linked Gold Nanoparticle Assemblies?", *J. Am. Chem. Soc.* 125:1643-1654, 2003.
Levy, "The Challenge of Antibiotic Resistance," *Scientific American* 278(3):46-53, 1998.
Li et al., "A Chemiluminescent Metalloimmunoassay Based on Silver Deposition on Colloidal Gold Labels," *Analytical Biochemistry* 359(2):247-252, 2006.
Liu et al., "Colorimetric Biosensors Based on DNAzyme-Assembled Gold Nanoparticles," *Journal of Fluorescence* 14(4):343-354, 2004.
Liu et al., "Optical Properties of Rodlike and Bipyramidal Gold Nanoparticles from Three-Dimensional Computations," *Physical Review B* 76:235428, 2007.
Liu et al., "A Simple and Specific Assay for Real-Time Colorimetric Visualization of β-Lactamase Activity by Using Gold Nanoparticles," *Agnew. Chemie Int. Ed.* 46:8799-8803, 2007.
Lu et al., "Environmentally Friendly Synthesis of Highly Monodisperse Biocompatible Gold Nanoparticles with Urchin-like Shape," *Langmuir* 24:1058-1063, 2008.
Majiduddin et al., "Molecular Analysis of Beta-Lactamase Structure and Function," *Int. J. Med. Microbiol.* 292:127-137, 2002.
Mayer et al., "A Label-Free Immunoassay Based Upon Localized Surface Plasmon Resonance of Gold Nanorods," *ACS Nano* 2(4):687-692, 2008.
Nicasio et al., "The Current State of Multidrug-Resistant Gram-Negative Bacilli in North America: Insights from the Society of Infectious Diseases Pharmacists," *Pharmaco-therapy* 28(2):235-249, 2008.
Norton et al., "Plasmon Resonances of Nanoshells of Spheroidal Shape," *IEEE Transactions on Nanotechnology* 6(6):627-638, 2007.
Pine et al., *Organic Chemistry*, McGraw-Hill, 4th Edition, 1981, "4-2 Conformations of Acyclic Compounds," pp. 97-99 & pp. 115-119.
Rao et al., "Nanotubes," *Chem. Phys. Chem.* 2:78-105, 2001.
Riccio et al., "Stereochemical Analysis of Natural Products. Approaches Relying on the Combination of NMR Spectroscopy and Computational Methods," *Pure Appl. Chem.* 75(2-3): 295-308, 2003.
Sau et al., "Room Temperature, High-Yield Synthesis of Multiple Shapes of Gold Nanoparticles in Aqueous Solution," *J. Am. Chem. Soc.* 126(28):8648-8649, 2004.
Schuck, "Use of Surface Plasmon Resonance to Probe the Equilibrium and Dynamic Aspects of Interactions Between Biological Macromolecules," *Annu. Rev. Biophys. Biomol. Struct.* 26: 541-566, 1997.
Smith et al., *March's Advanced Organic Chemistry: Reactions Mechanisms and Structure*, Sixth Edition, Wiley-Interscience, pp. 155-158 & pp. 164-166, 2007.
Stalmashonak et al., "Optical Three-Dimensional Shape Analysis of Metallic Nanoparticles after Laser-Induced Deformation," *Optics Letters* 32(21):3215-3217, 2007.
Steiner et al., "Plasmon-Enhanced Emission in Gold Nanoparticle Aggregates," *J. Phys. Chem. C* 112:3103-3108, 2008.
Turkevich et al., "The Nucleation and Growth Processes in the Synthesis of Colloidal Gold," *J. Discuss. Faraday Soc.* 11:55-75, 1951.
Wilke et al., "β-Lactam Antibiotic Resistance: A Current Structural Perspective," *Current Opinion in Microbiology* 8:525-533, 2005.
Willets et al., "Localized Surface Plasmon Resonance Spectroscopy and Sensing," *Annu. Rev. Phys. Chem.* 58:267-297, 2007.
Xing et al., "Cell-Permeable Near-Infrared Fluorogenic Substrates for Imaging β-Lactamase Activity," *J. Am. Chem. Soc.* 127:4158-4159, 2005.
Xu et al., "A Self-Assembled Quantum Dot Probe for Detecting β-Lactamase Activity," *Biochemical and Biophysical Research Communications* 344(3):931-935, 2006.
Yang et al., "Using β-Lactamase to Trigger Supramolecular Hydrogelation," *J. Am. Chem. Soc.* 129:266-267, 2007.
Yeshchenko et al., "Optical Properties of Sol-Gel Fabricate Mn/SiO$_2$ Nanocomposites: Observation of Surface Plasmon Resonance in Mn Nanoparticles," *Applied Surface Science* 254:2736-2742, 2008.
Zhang et al., "Nickle and Cobalt Nanoparticles Produced by Laser Ablation of Solids in Organic Solution," *Materials Letters* 62:1521-1524, 2008.
Zlokarnik et al., "Quantitation of Transcription and Clonal Selection of Single Living Cells with β- Lactamase as Reporter," *Science* 279:84-88, 1998.

\* cited by examiner

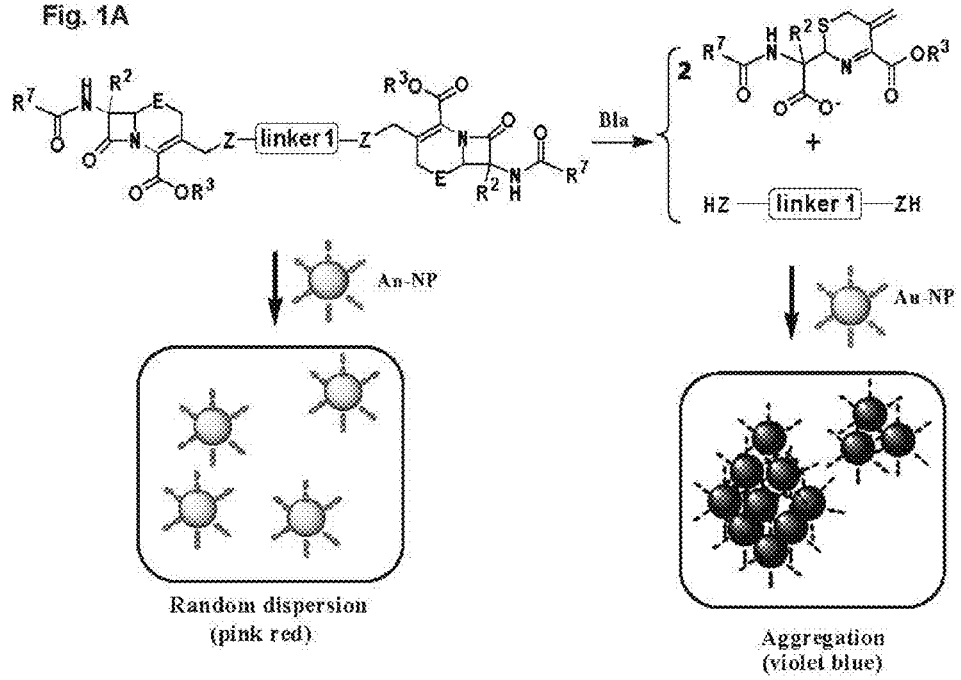
Fig. 1A
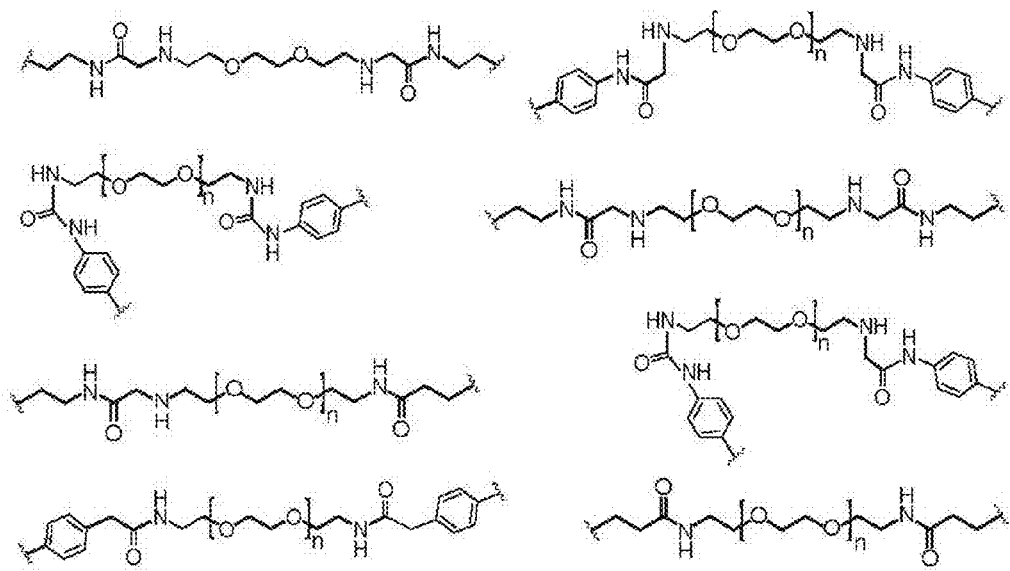
Fig. 1B    exemplary linkers:

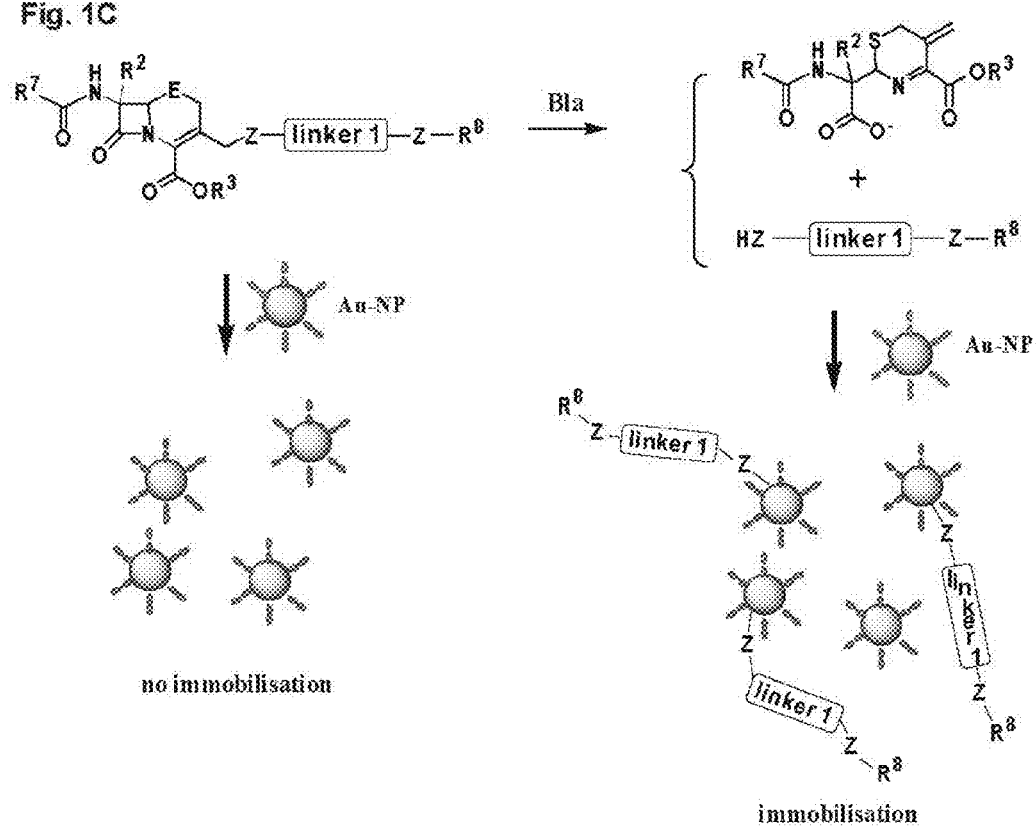
Fig. 1C
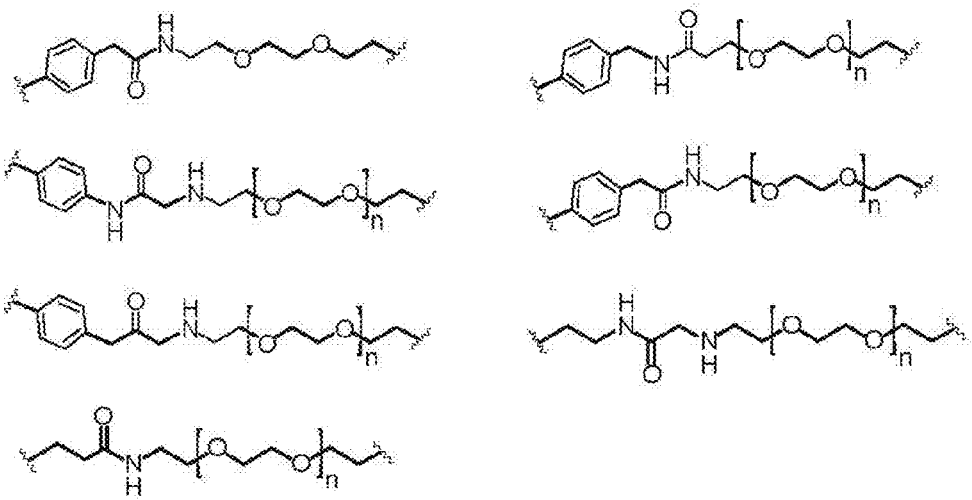
Fig. 1D    additional exemplary linkers:

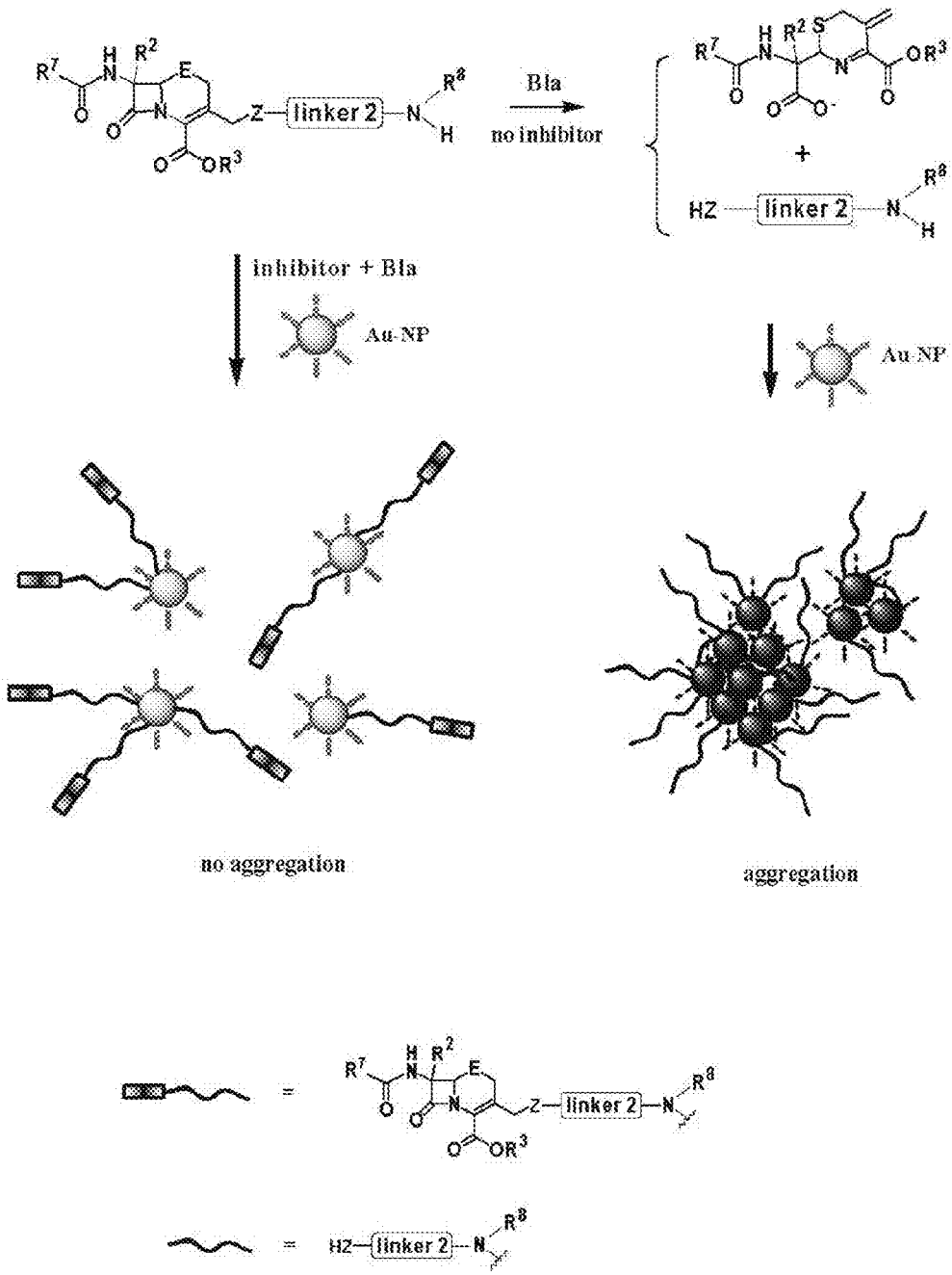

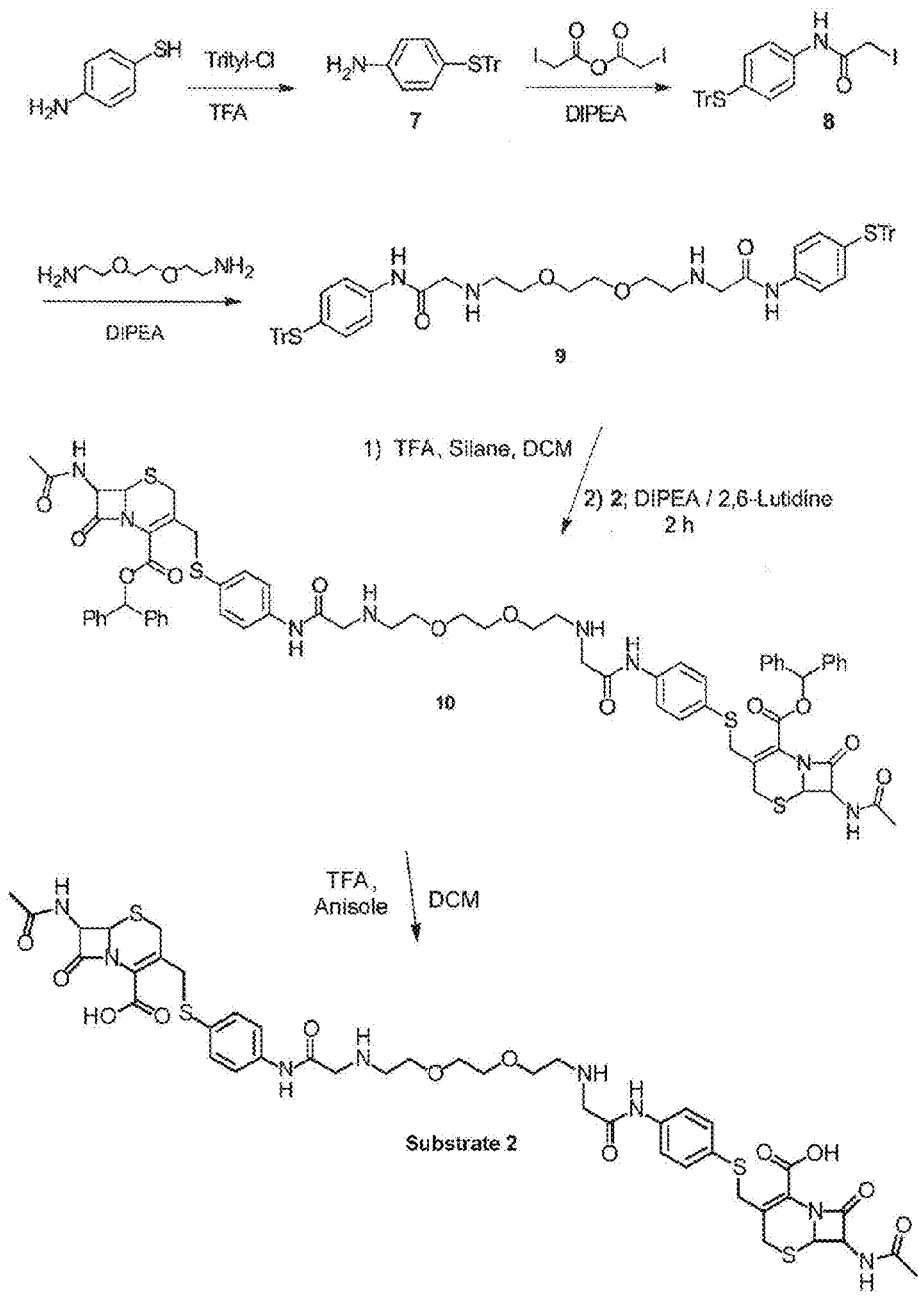

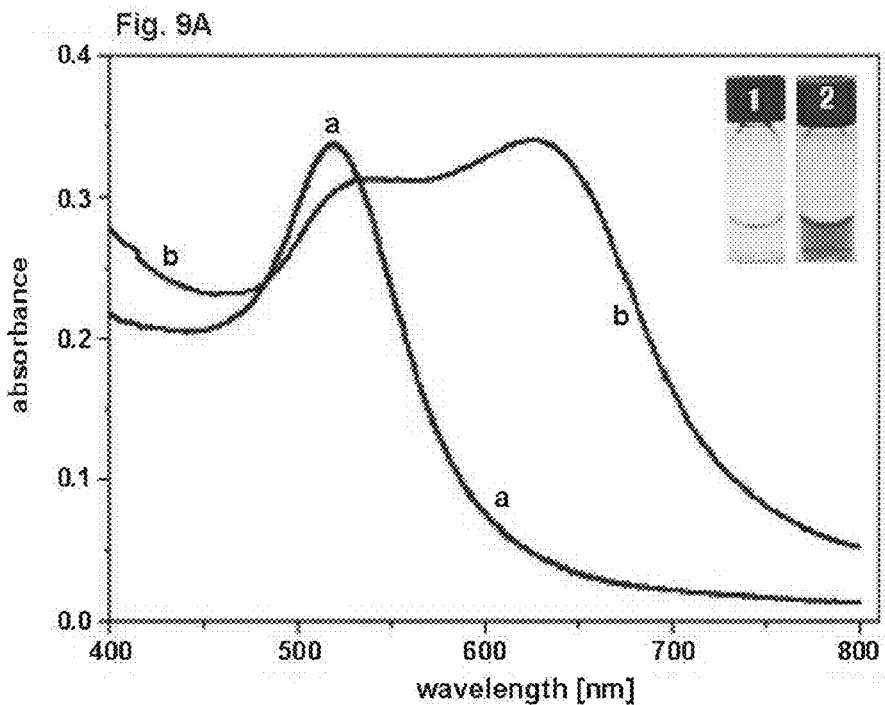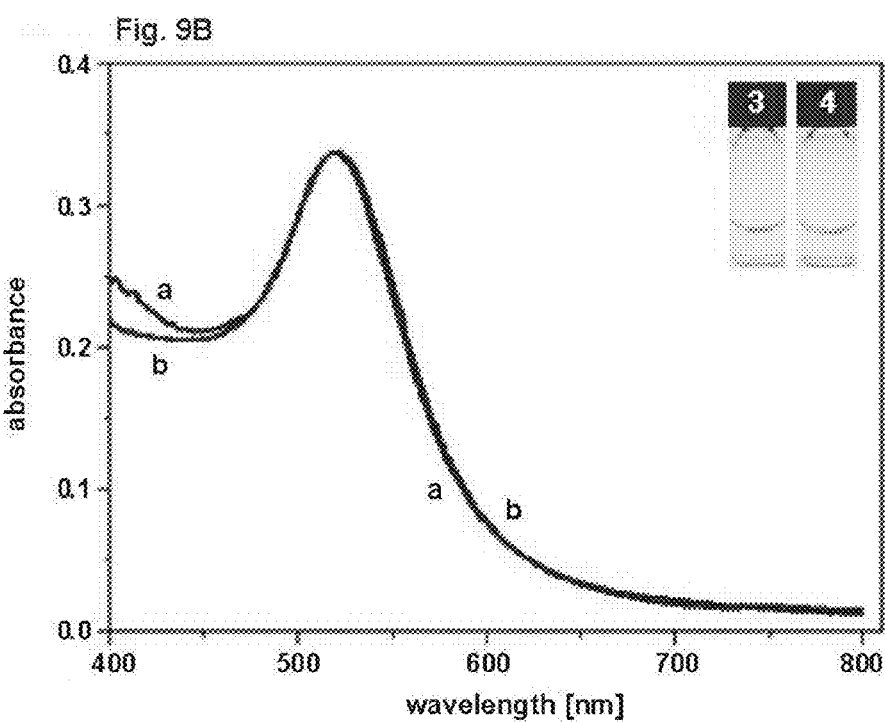

A: blue color
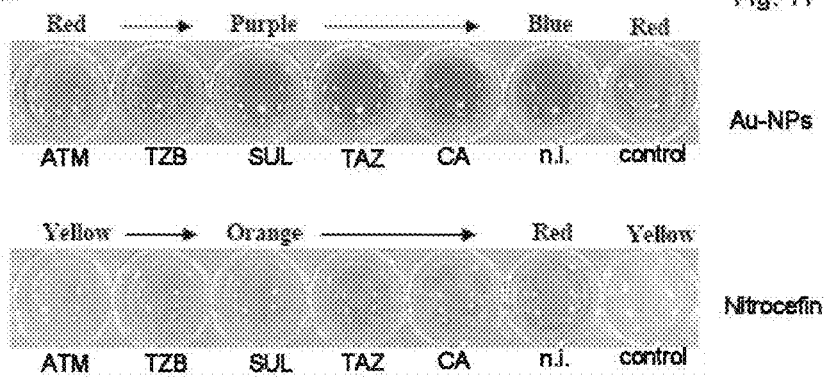
B: red color
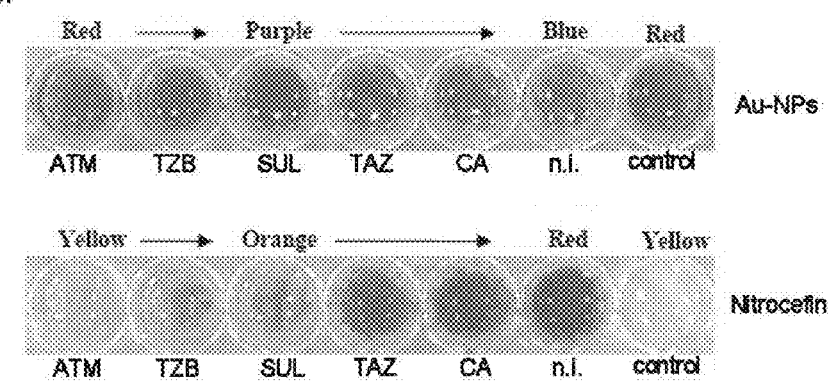
C: yellow color
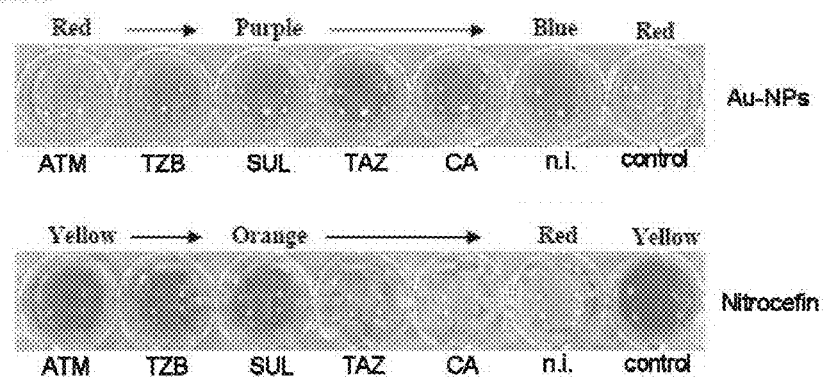
Fig. 11

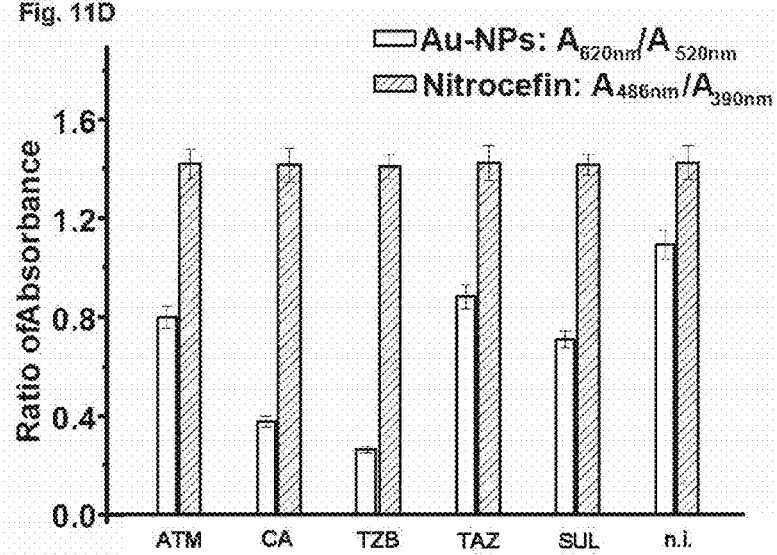
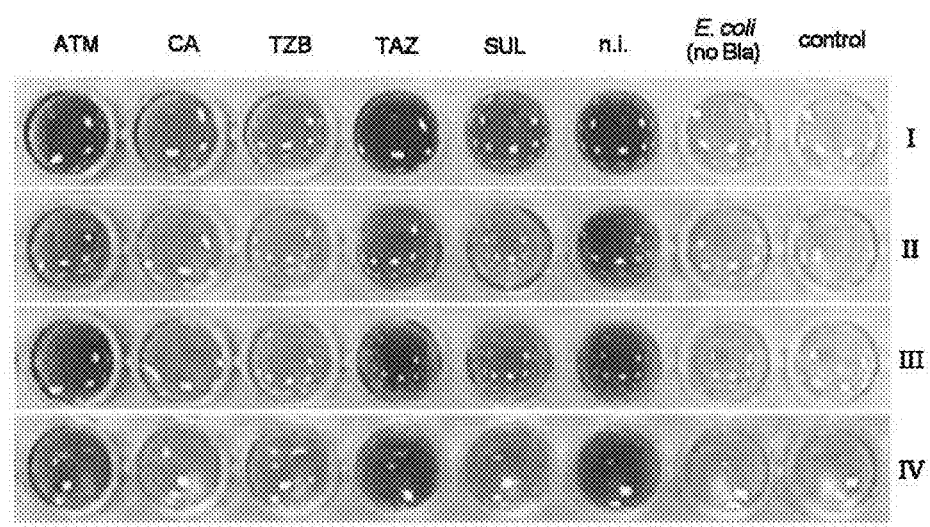

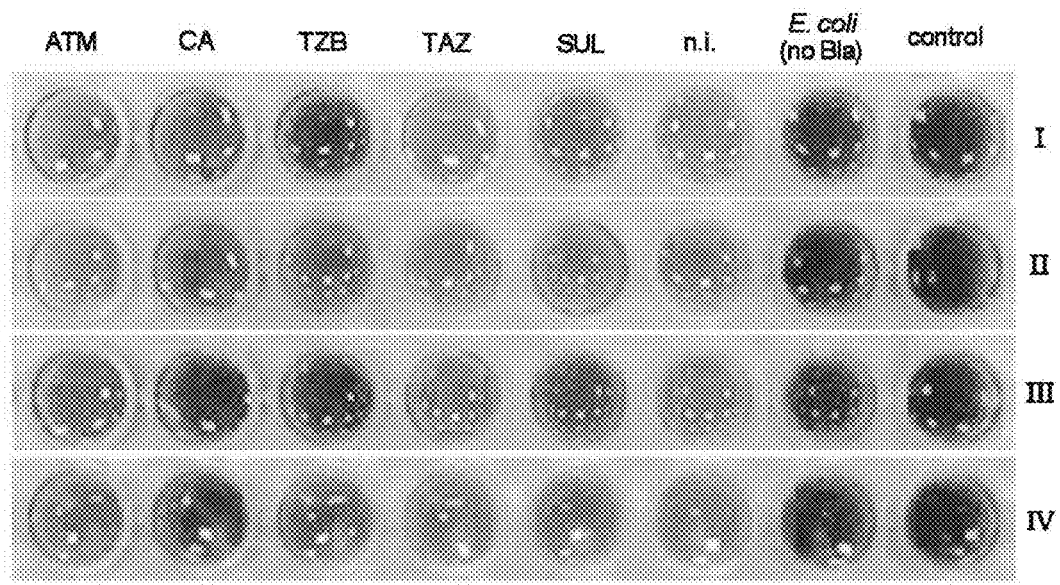
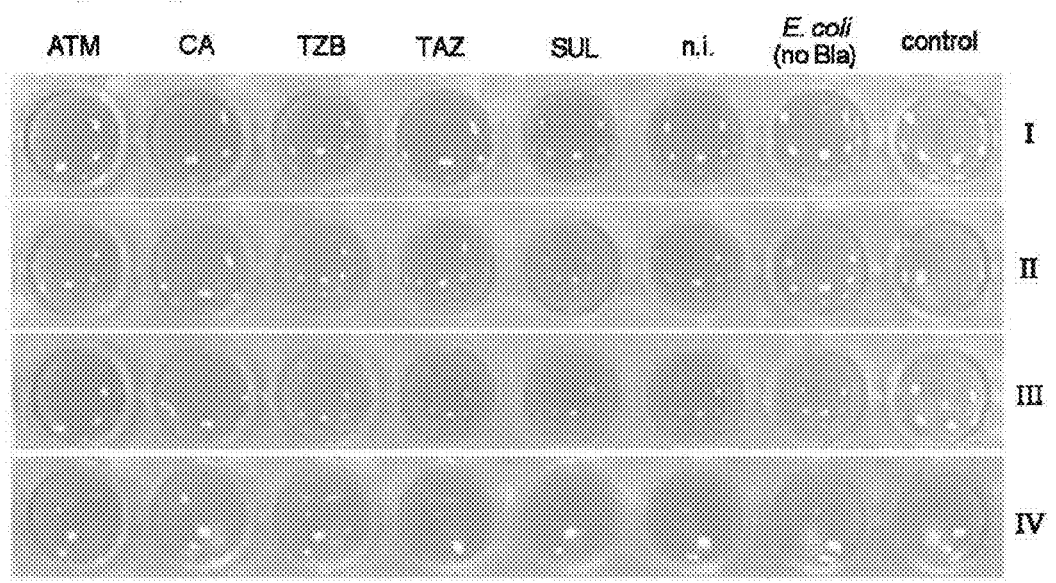

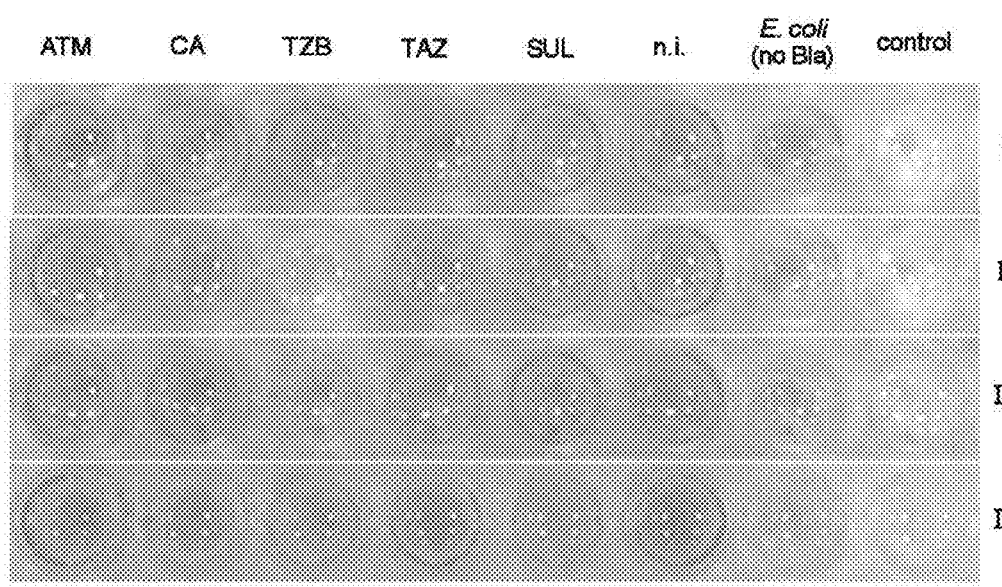
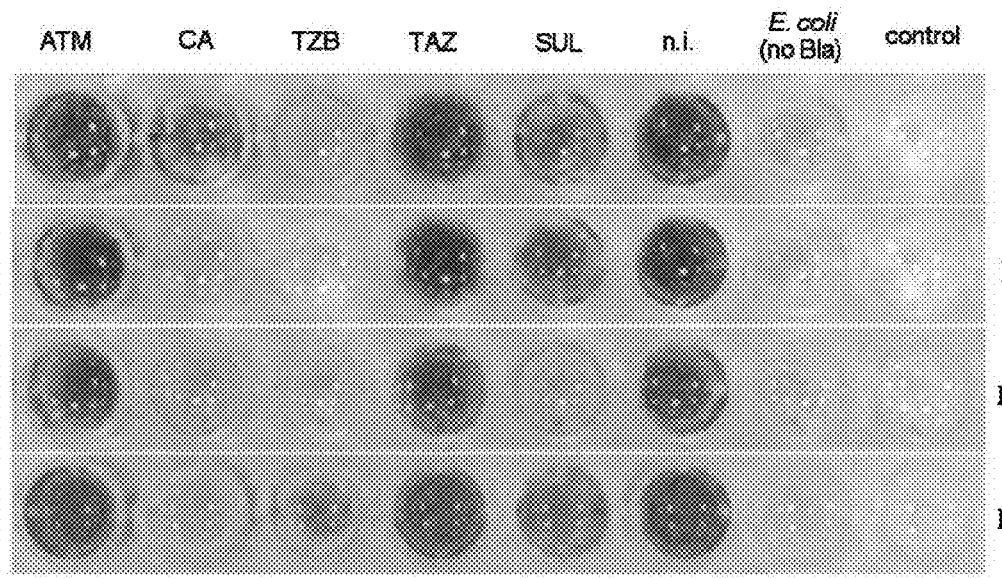
Fig. 13

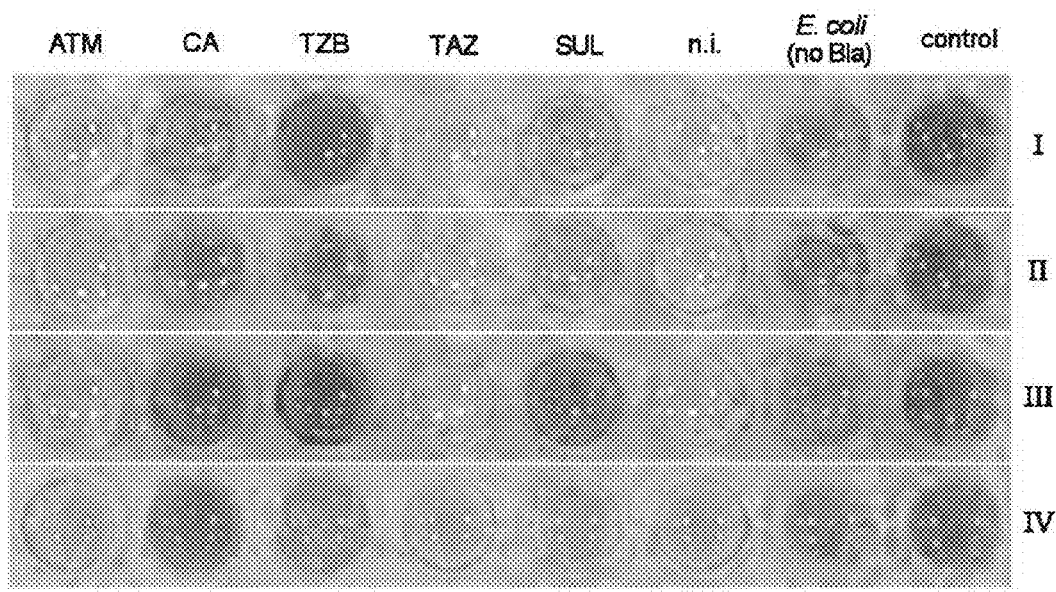
Fig. 13C: yellow color
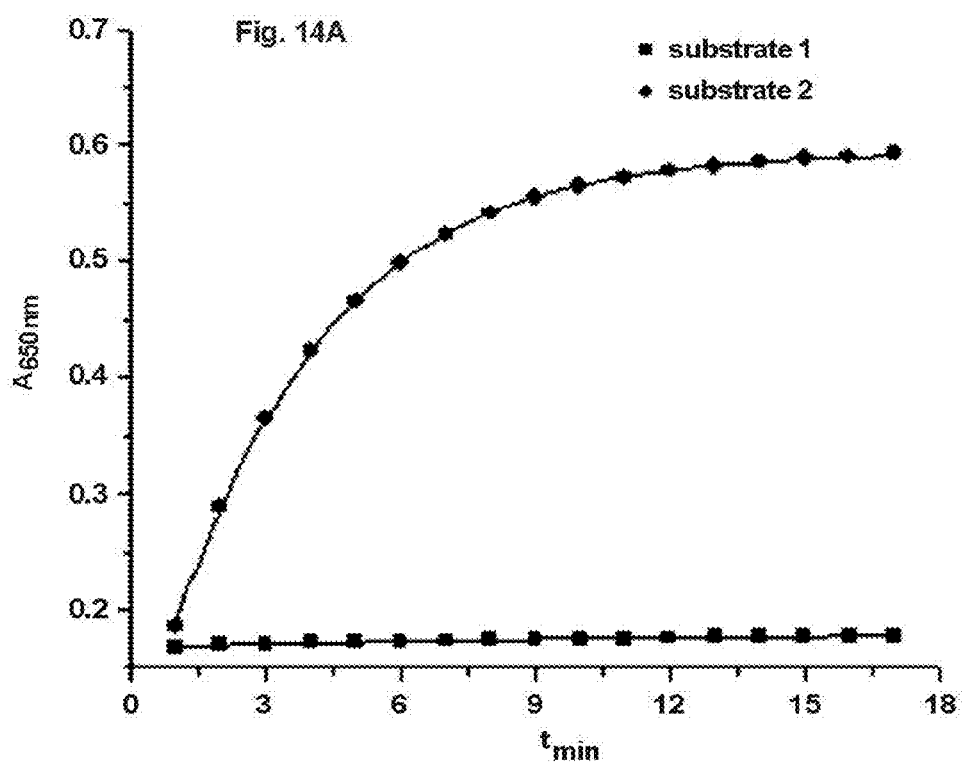

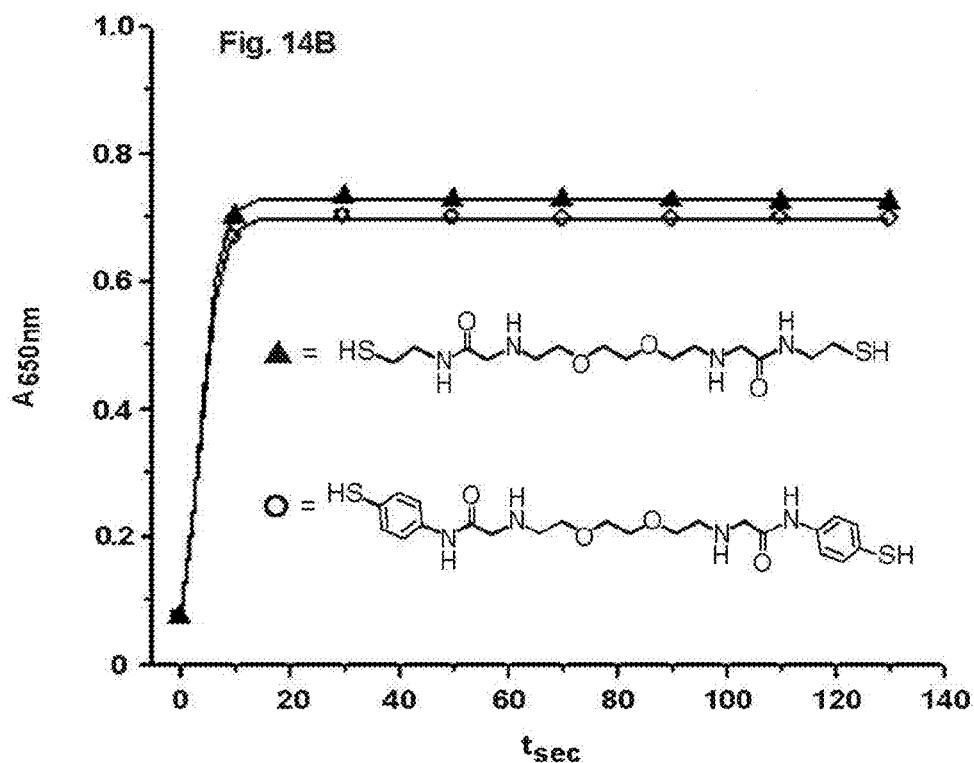
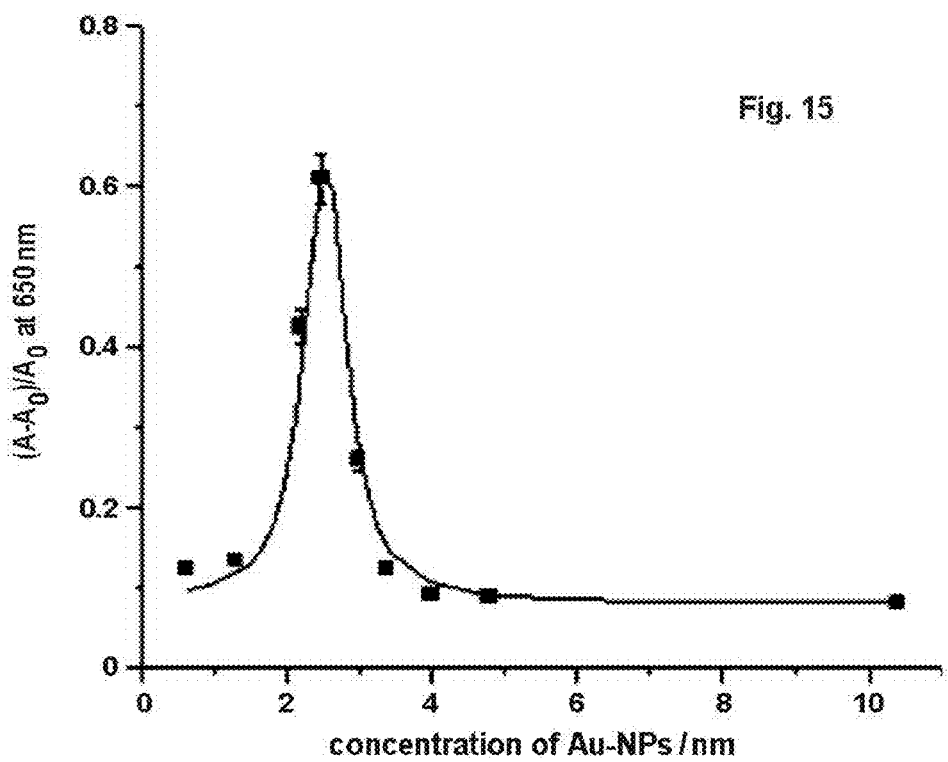

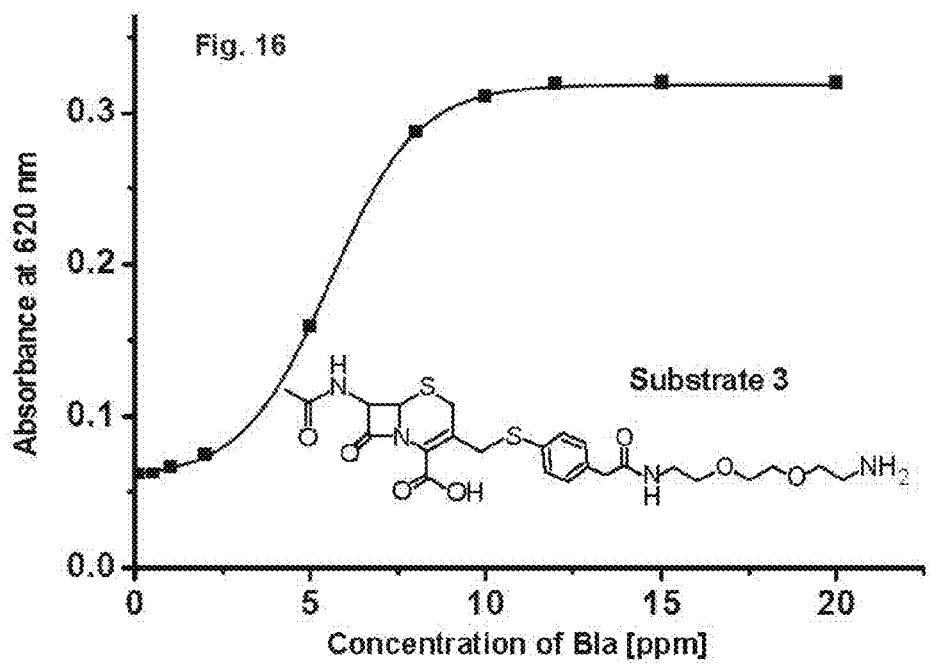
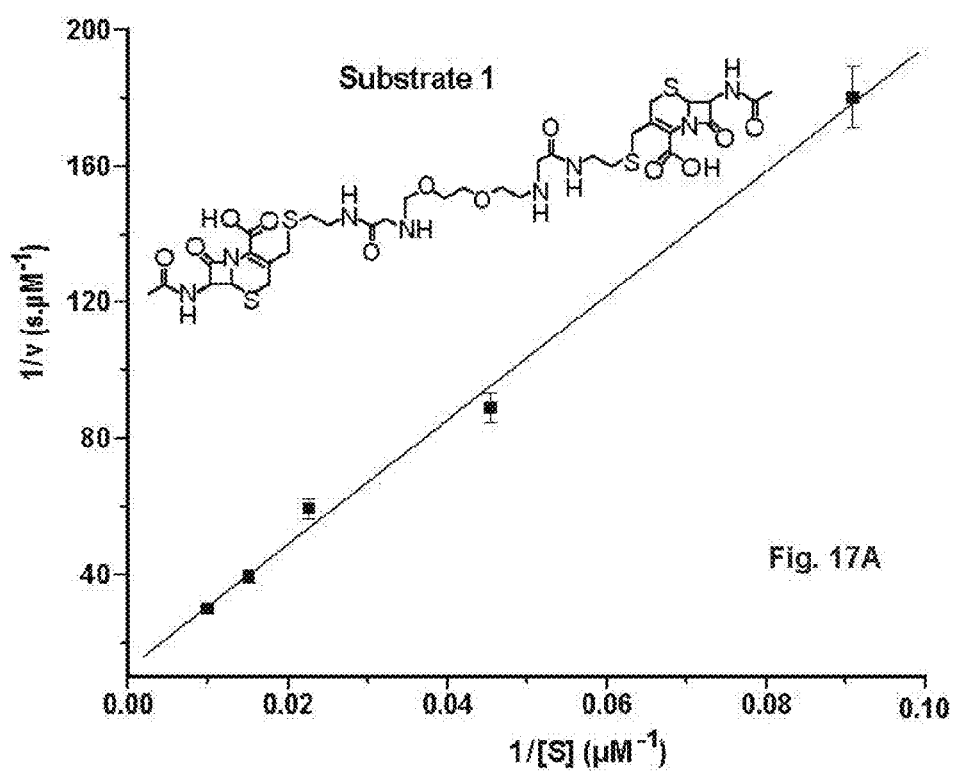

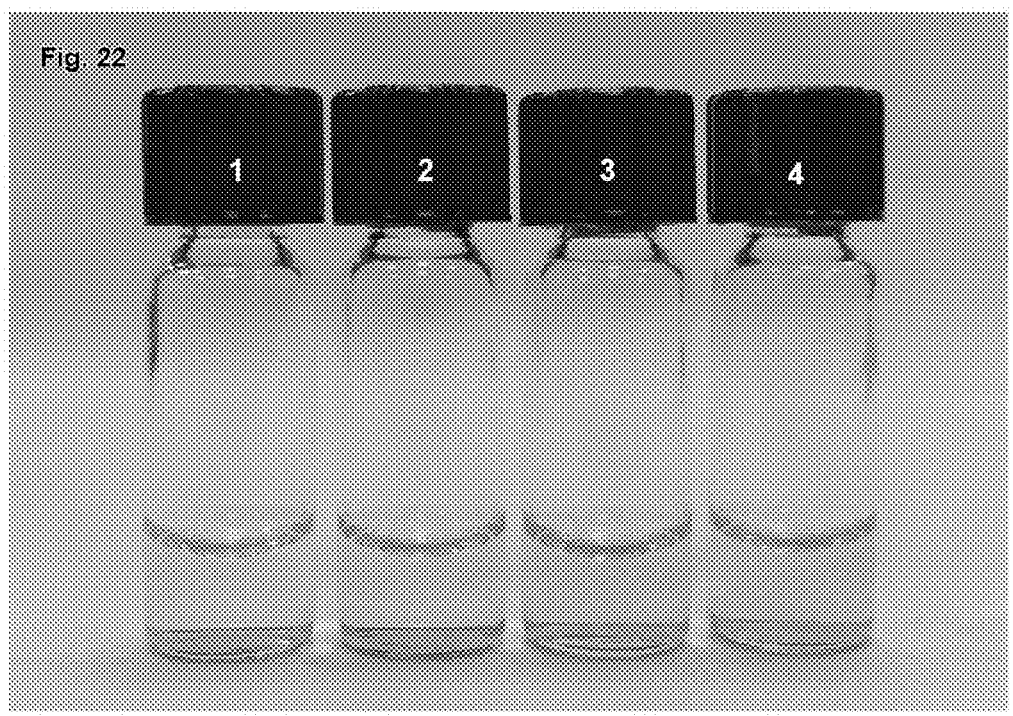

METHODS AND COMPOUNDS FOR DETECTING BETA-LACTAMASE ACTIVITY

CROSS-REFERENCE TO RELATED APPLICATION

This application is a divisional of U.S. patent application Ser. No. 12/113,109 filed Apr. 30, 2008, now allowed, which is incorporated herein by reference in its entirety.

FIELD OF THE INVENTION

The present invention relates to methods of and compounds for detecting β-lactamase activity, including methods of forming these compounds. The invention also relates to a method of identifying a β-lactamase modulator and to a kit for detecting β-lactamase activity.

BACKGROUND OF THE INVENTION

The discovery of β-lactam antibiotics was one of the most important steps in the struggle against pathogenic bacteria. β-Lactam antibiotics such as penicillins and cephalosporins are one of the three largest antibiotic classes and the most heavily prescribed antibiotics in clinical use today. They target enzymes that synthesize the bacterial cell wall. However, increased resistance of bacterial infections to antibiotic treatment has been extensively documented and has become a generally recognized problem for clinicians worldwide, in both hospital and community settings (see, e.g., Levy, S. B. *Scientific American* (1998) 278, 3, 46-53; Fisher, J. F., et al. *Chem. Rev.* (2005) 105, 395-424). One mechanism of bacterial self-defense against β-lactam antibiotics is the production of β-lactamases (Bla), bacterial enzymes that can hydrolyze the β-lactam ring in penicillins and cephalosporins with high catalytic efficiency and render the bacteria resistant to the β-lactam antimicrobial reagents (see, e.g., Wilke, M. S., et al. *Current Opinion in Microbiology* (2005) 8, 525-533).

β-Lactamases are organized into four molecular classes (A, B, C and D) based on their amino acid sequence, their substrate spectrum and responses to inhibitors. Class A enzymes have a molecular weight of about 29 kDa and can preferentially hydrolyze penicillins. Class B enzymes include metalloenzymes that have a broader substrates profile than other β-lactamase classes. Class C enzymes have molecular weights of approximately 39 kDa and include the chromosomal cephalosporinases of gram-negative bacteria, which are responsible for the resistance of gram-negative bacteria to a variety of both traditional and newly designed antibiotics. In addition, class C enzymes also include the lactamase of P99 *Enterobacter cloacae*, which is responsible for making this *Enterobacter* species one of the most widely spread bacterial agents in United States hospitals. The recently recognized class D enzymes are serine hydrolases, which exhibit a unique substrates profile. The spread of antibiotics resistance conferred by expression of β-lactamase in bacteria threatens the ability to treat bacterial infections.

Therefore, detecting β-lactamases and screening their inhibitors (see, e.g., Buynak, J. D., *Biochemical Pharmacology* (2006) 71, 930-940) in biological samples before conducting the efficient antibiotic therapy, is extremely important clinically. Accordingly procedures for detecting β-lactamases have been developed such as fluorescent (e.g., genotyping based on polymerase chain reaction (PCR)) or chromogenic assays (such as the well known nitrocefin and PADAC indicators). Some other fluorogenic and hydrogel based substrates have also been developed as reporters for imaging the gene expression of β-lactamases in vitro and in vivo (Zlokarnik, L., et al., *Science* (1998) 279, 84-88; Gao, W. Z., et al., *J. Am. Chem. Soc.* (2003) 125, 11146-11147; Xing, B. G., et al., *J. Am. Chem. Soc.* (2005) 127, 4158-4159; Yang, Z. M., et al., *J. Am. Chem. Soc.* (2007) 129, 266-267).

However, current detection methods have significant drawbacks such as laborious manipulation, time-consuming processes, requirement for highly specific instrumentation, and limited chemical stability and aqueous solubility of reagents used. There is therefore a need for a simple, rapid, sensitive and economical detection method.

Accordingly, it is an object of the present invention to provide an alternative method of detecting β-lactamases that avoids these disadvantages.

This object is solved by modulating the formation of such complex among others by the methods as described in the independent claims.

SUMMARY OF THE INVENTION

In a first aspect the invention provides a compound of one of general formulas (I)-(III) and (VII)-(IX):

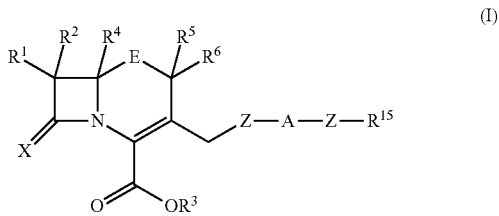

(I)

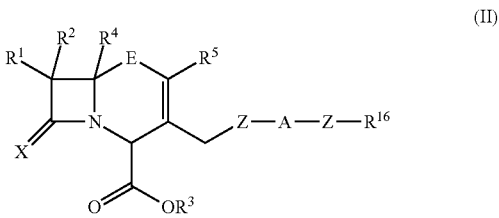

(II)

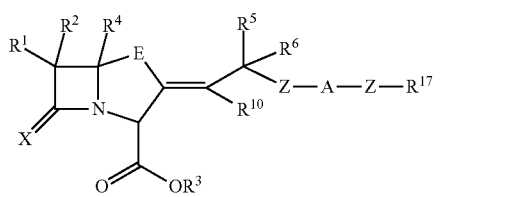

(III)

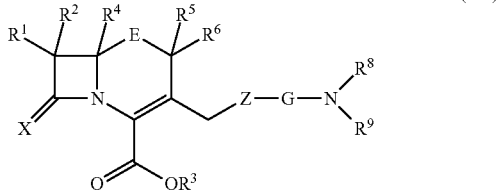

(VII)

-continued

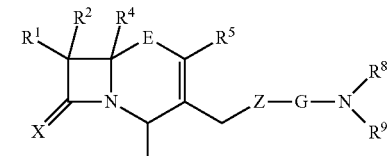
(VIII)

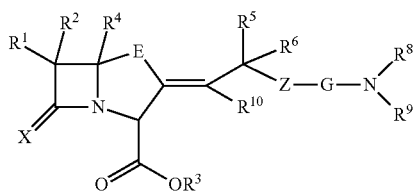
(IX)

In these general formulas $R^1$ is H, a halogen atom or

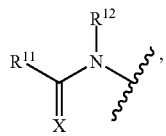

with X being O, S, Se or NH. $R^{11}$ and $R^{12}$ are independently selected hydrogen or an aliphatic, an alicyclic, an aromatic, an arylaliphatic, or an arylalicyclic group that includes 0 to about 3 heteroatoms independently selected from the group consisting of N, O, S, Se and Si. $R^2$ is one of H, halogen, an aliphatic group, an alicyclic group, an aromatic group, an arylaliphatic group and an arylalicyclic group, that includes 0 to about 3 heteroatoms selected from the group consisting of N, O, S, Se and Si. $R^3$ to $R^5$, $R^6$ in general formulas (I), (III), (VII) and (IX), as well as $R^8$ and $R^9$ in general formulas (VII)-(IX), and $R^{10}$ in general formulas (III) and (IX), are independently selected H or one of an aliphatic group, an alicyclic group, an aromatic group, an arylaliphatic group and an arylalicyclic group, that includes 0 to about 3 heteroatoms selected from the group consisting of N, O, S, Se and Si. $R^{15}$ in general formula (I), $R^{16}$ in general formula (II) and $R^{17}$ in general formula (III) are independently selected from H or one of an aliphatic group, an alicyclic group, an aromatic group, an arylaliphatic group and an arylalicyclic group, that includes 0 to about 5 heteroatoms selected from the group consisting of N, O, S, Se and Si. E is S, SO, $SO_2$ or $CH_2$. Z is S or Se. In general formulas (I)-(III) and (VII)-(IX) X is also O, S, Se or NH (supra). A in general formulas (I)-(III) is a bridge defined by an aliphatic, alicyclic, aromatic, arylaliphatic, or arylalicyclic radical with a main chain of 1-50 carbon atoms and 0-50 heteroatoms. G in general formulas (VII)-(IX) is also a bridge defined by an aliphatic, alicyclic, aromatic, arylaliphatic, or arylalicyclic radical with a main chain of 1-50 carbon atoms and 0-50 heteroatoms. The above compounds of general formulas (I) to (III) and (VII)-(IX), and in particular of general formulas (I) and (II), are provided with the proviso that from the bridge A the following group is excluded:

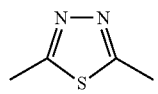

In a second aspect the invention provides a compound of one of general formulas (XXII)-(XXIV), (XXXIII), (XXXIV) or (XXXVI):

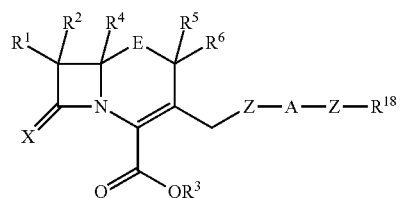
(XXII)

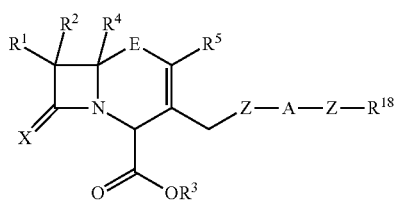
(XXIII)

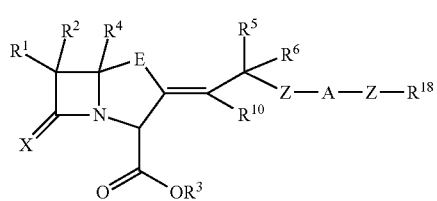
(XXIV)

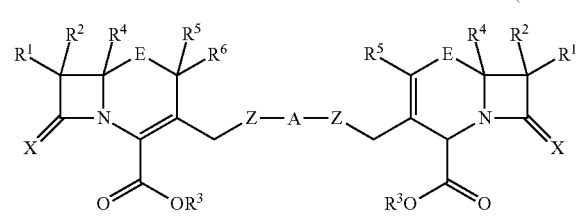
(XXXIII)

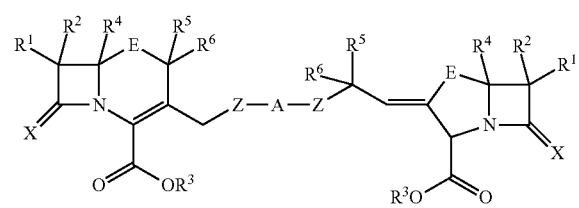
(XXXIV)

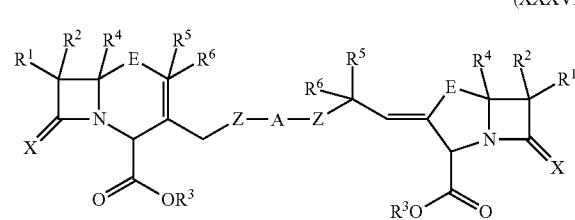
(XXXVI)

-continued

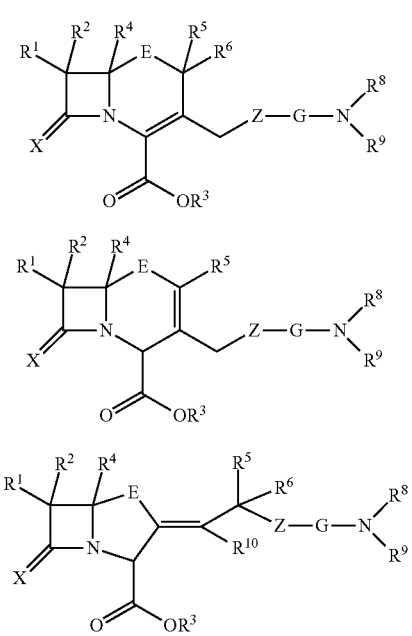

In these general formulas R¹ is H, a halogen atom or

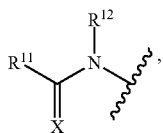

with X being O, S, Se or NH. $R^{11}$ and $R^{12}$ are independently selected hydrogen or an aliphatic group, an alicyclic group, an aromatic group, an arylaliphatic group, or an arylalicyclic group, that includes 0 to about 3 heteroatoms selected from the group consisting of N, O, S, Se and Si. $R^2$ in the above general formulas is one of H, halogen, an aliphatic group, an alicyclic group, an aromatic group, an arylaliphatic group and an arylalicyclic group, that includes 0 to about 3 heteroatoms selected from the group consisting of N, O, S, Se and Si. $R^3$ to $R^5$, $R^6$ in general formulas (VII), (IX), (XXII), (XXIV), (XXXIII), (XXXIV) and (XXXVI), as well as $R^8$ and $R^9$ in general formulas (VII)-(IX), and $R^{10}$ in general formula (XXIV), are independently selected H or one of an aliphatic group, an alicyclic group, an aromatic group, an arylaliphatic group and an arylalicyclic group, that includes 0 to about 3 heteroatoms selected from the group consisting of N, O, S, Se and Si. $R^{18}$ in formulas (XXII)-(XXIV) is an aliphatic group, an aromatic group, an arylaliphatic group, an arylalicyclic group or a monocyclic alicyclic group, that includes 0 to about 3 heteroatoms selected from the group consisting of N, O, S, Se and Si. E is S, SO, $SO_2$ or $CH_2$. Z in the above general formulas is S or Se. In the above general formulas X is also O, S, Se or NH (supra).

A in general formulas (XXII)-(XXIV), (XXXIII), (XXXIV) and (XXXVI) is a bridge defined by an aliphatic, alicyclic, aromatic, arylaliphatic, or arylalicyclic radical with a main chain of 1-50 carbon atoms and 0-50 heteroatoms. G in general formulas (VII)-(IX) is also a bridge defined by an aliphatic, alicyclic, aromatic, arylaliphatic, or arylalicyclic radical with a main chain of 1-50 carbon atoms and 0-50 heteroatoms.

The above compounds (I)-(III), (VII)-(IX), (XXII)-(XXIV), (XXXIII), (XXXIV) and (XXXVI) are further provided with the proviso that the three following compounds are excluded:

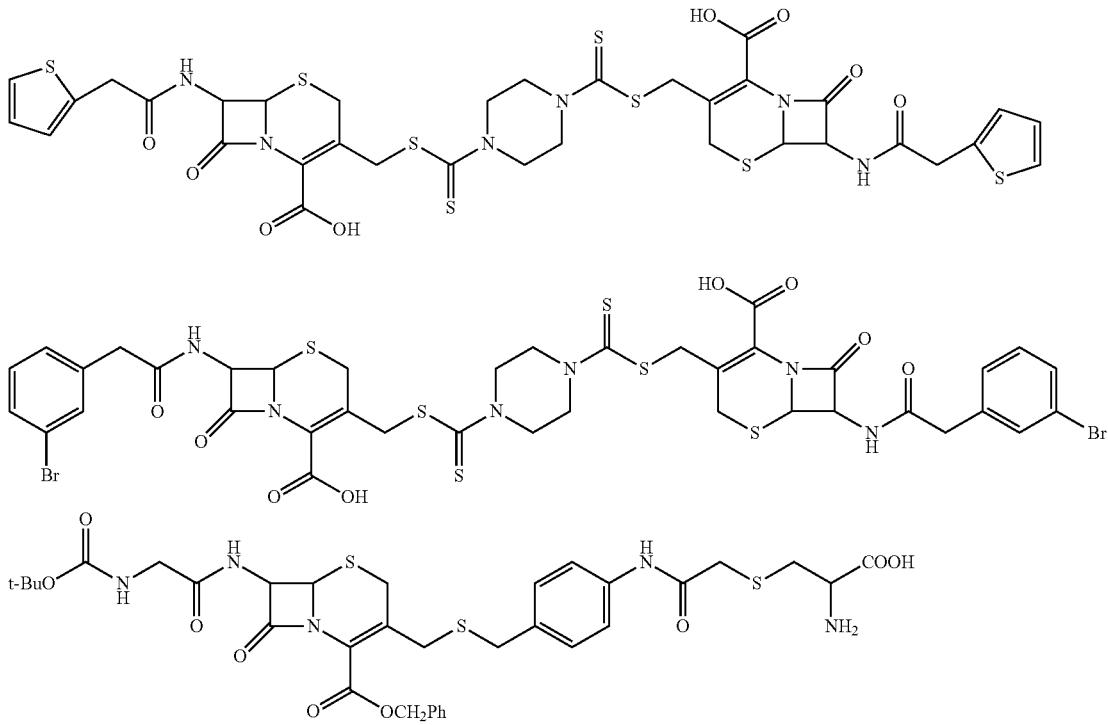

The above compound (VII) is furthermore provided with the proviso that the following compounds are excluded:
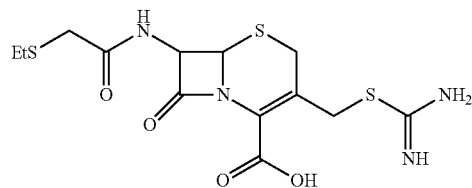
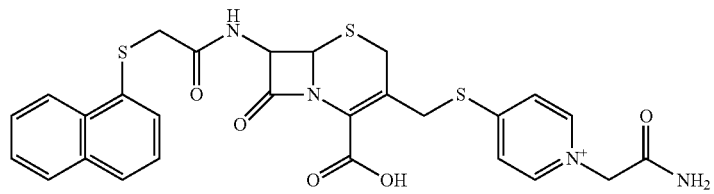
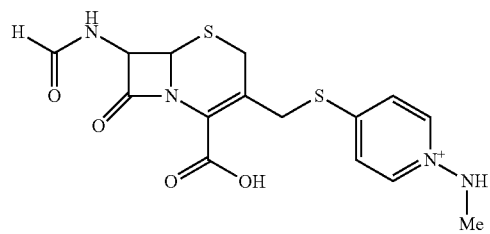
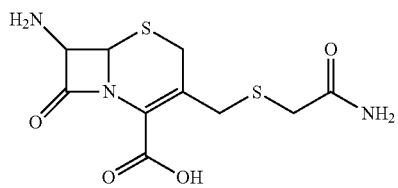
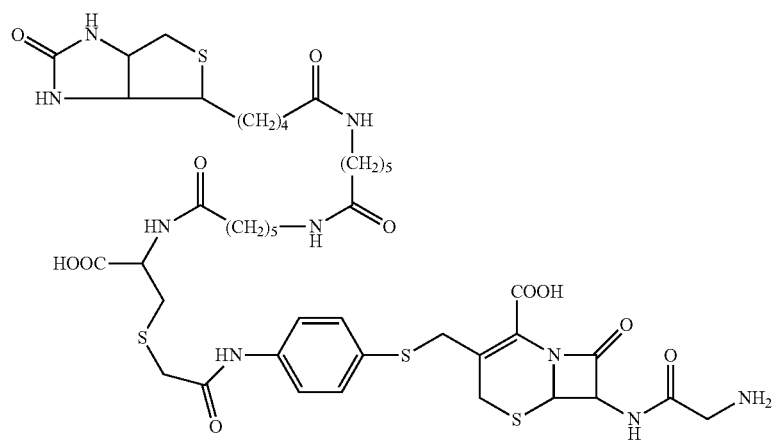
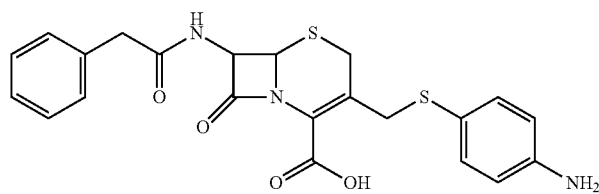
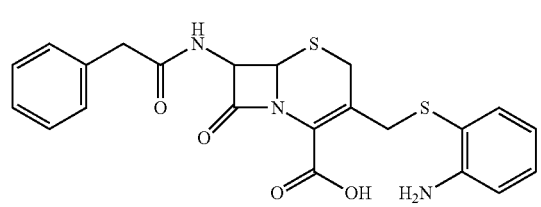
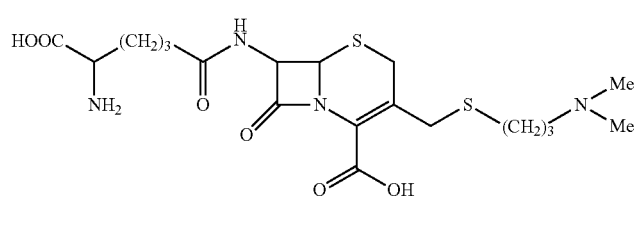
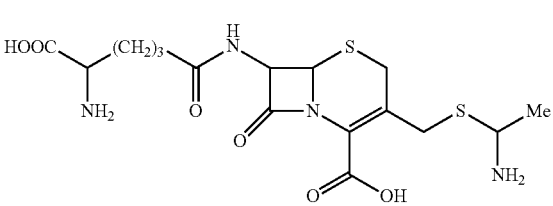

In a third aspect the present invention provides a method of forming a compound of one of general formulas (I)-(III) (supra). The method includes reacting a compound of one of general formulas (XX), (XXX) and (XXXI):

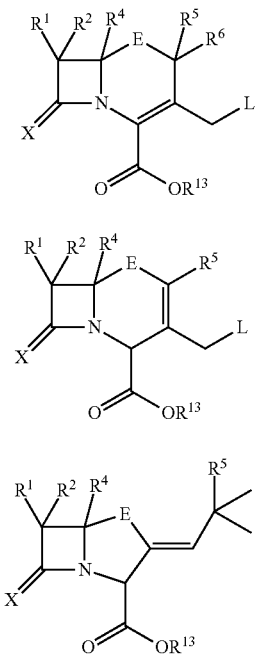

with a compound of general formula $R^{14}$—Z-A-Z—$R^{14}$. L in formula (XX) is a suitable leaving group. $R^{13}$ in formulas (XX), (XXX) and (XXXI) is one of an aliphatic, an alicyclic, an aromatic, an arylaliphatic, and an arylalicyclic group, that includes 0 to about 3 heteroatoms independently selected from N, O, S, Se and Si. $R^{14}$ in the compound of formula $R^{14}$—Z-A-Z—$R^{14}$ is one of an aliphatic, an alicyclic, an aromatic, an arylaliphatic, and an arylalicyclic group, that includes 0 to about 3 heteroatoms selected from N, O, S, Se and Si. X in the above formulas, as well as in other formulas below, is one of O, S, Se and NH.

In a fourth aspect the present invention provides a method of forming a compound of one of general formulas (XXII)-(XXIV) (supra). The method includes reacting a compound of one of general formulas (XX), (XXX) and (XXXI) (supra) with a compound of one of general formula

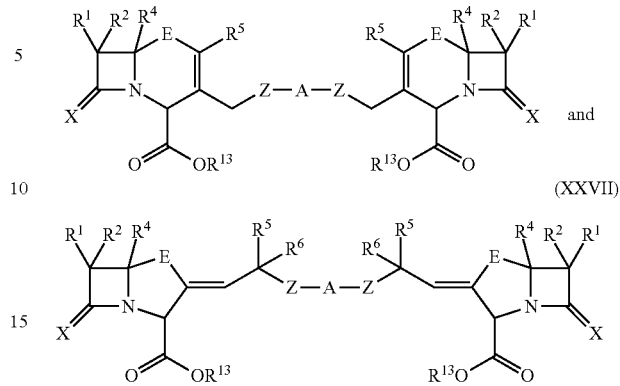

$R^{13}$ in formulas (XXV), (XXVI) and (XXVII) is one of an aliphatic, an alicyclic, an aromatic, an arylaliphatic, and an arylalicyclic group, that includes 0 to about 3 heteroatoms independently selected from N, O, S, Se and Si. $R^{14}$ in formula (LI) is selected from the group consisting of an aliphatic group, an alicyclic group, an aromatic group, an arylaliphatic group, and an arylalicyclic group, that includes 0 to about 3 heteroatoms selected from the group consisting of N, O, S, Se and Si. $R^6$ in formulas (XXV) and (XXVII) is H or one of an aliphatic group, an alicyclic group, an aromatic group, an arylaliphatic group and an arylalicyclic group, that includes 0 to about 3 heteroatoms selected from the group consisting of N, O, S, Se and Si.

In a fifth aspect the present invention provides a method of forming a compound of one of general formulas (VII) to (IX) (supra). The method includes reacting a compound of one of general formulas (XX), (XXX) and (XXXI) (supra) with a compound of general formula (LII)

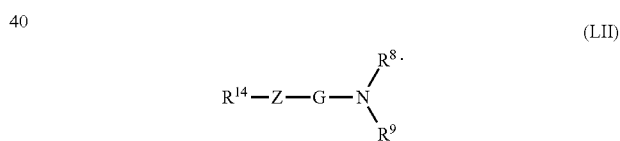

In formula (LII) $R^{14}$ is selected from the group consisting of an aliphatic group, an alicyclic group, an aromatic group, an arylaliphatic group, and an arylalicyclic group, that includes 0 to about 3 heteroatoms independently selected from the group consisting of N (nitrogen), O (oxygen), S (sulfur), Se (selenium) and Si (silicon). Z, G, $R^8$ and $R^9$ are as defined above.

In a sixth aspect the present invention provides a method of detecting β-lactamase activity in a sample. The method includes contacting the sample with a nanoparticulate tag. The nanoparticulate tag includes a metal or a combination of metals, or it includes a nanotube of a metal, of boron nitride and/or of carbon. The nanoparticulate tag is capable of forming one of a covalent bond, a coordinative bond and a non-covalent interaction with a thio and/or a seleno group. The method further includes contacting the sample with a compound of one of general formulas (I)-(III) and (VII)-(IX) (supra). The method also includes allowing beta-lactamase activity in the sample to cleave a β-lactam moiety of the compound of one of general formulas (I) to (III) and (VII) to (IX). A compound of one of formulas (I) to (III) may in some embodiments have a moiety $R^{15}$, $R^{16}$ and $R^{17}$, respectively, that is or includes one of the bicyclic moieties (IV)-(VI):

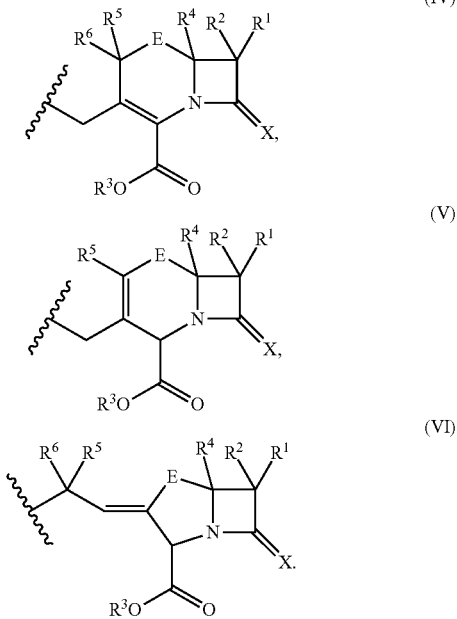

$R^1$ to $R^5$, $R^6$ in general formulas (IV) and (VI), as well as E and X, are as defined above. Where a respective compound is used the method generally includes allowing β-lactamase activity in the sample to cleave at least one β-lactam moiety of the respective compound.

As a result of allowing β-lactamase activity to cleave a β-lactam moiety a cleavage moiety is released. The cleavage moiety can be of one of the formulas Z-A-Z, Z-A-Z—$R^{15}$, Z-A-Z—$R^{16}$, and Z-A-Z—$R^{17}$ where the cleaved compound is of one of general formulas (I) to (III). The cleavage moiety is of the formula Z-G-N($R^8$)$R^9$ where the cleaved compound is of one of general formulas (VII) to (IX). The method also includes allowing this cleavage moiety, Z-A-Z, Z-A-Z—$R^{15}$, Z-A-Z—$R^{16}$, Z-A-Z—$R^{17}$ or Z-G-N($R^8$)$R^9$, respectively, to be immobilized on the surface of the nanoparticulate tag by forming one of a covalent bond, a coordinative bond and a non-covalent interaction therewith via a Z atom. Where the cleaved compound is of one of general formulas (I) to (III), the cleavage moiety Z-A-Z, Z-A-Z—$R^{15}$, Z-A-Z—$R^{16}$, and Z-A-Z—$R^{17}$, respectively is immobilized on the surface of the nanoparticulate tag by forming a covalent bond, a coordinative bond or a non-covalent interaction therewith via a Z atom, typically via at least one of its Z atoms. Where the cleaved compound is of one of general formulas (VII) to (IX), the cleavage moiety Z-G-N($R^8$)$R^9$ is immobilized on the surface of the nanoparticulate tag by forming a covalent bond, a coordinative bond or a non-covalent interaction therewith via the Z atom. Further, the method includes determining the presence of beta-lactamase activity based on the presence of the cleavage moiety, Z-A-Z, Z-A-Z—$R^{15}$, Z-A-Z—$R^{16}$, Z-A-Z—$R^{17}$ or Z-G-N($R^8$)$R^9$, respectively, immobilized onto the surface of the nanoparticulate tag.

In a seventh aspect the present invention provides a method of detecting β-lactamase activity in a sample. The method includes contacting the sample with a nanoparticulate tag. The nanoparticulate tag includes a metal or a combination of metals, or it includes a nanotube of a metal, of boron nitride and/or of carbon. The nanoparticulate tag is capable of forming one of a covalent bond, a coordinative bond and a non-covalent interaction with a thio and/or a seleno group. The method further includes contacting the sample with a compound of one of general formulas (VII)-(IX), (XXII)-(XXIV), (XXXIII), (XXXIV) and (XXXVI) (supra). The method also includes allowing beta-lactamase activity in the sample to cleave a beta-lactam moiety of the compound of one of general formulas (VII)-(IX), (XXII)-(XXIV), (XXXIII), (XXXIV) and (XXXVI). As a result of allowing β-lactamase activity to cleave a β-lactam moiety a cleavage moiety is released. The cleavage moiety is of the formula Z-A-Z where the cleaved compound is of one of general formulas (XXXIII), (XXXIV) and (XXXVI). The cleavage moiety is of the formula Z-A-Z—$R^{18}$ where the cleaved compound is of one of general formulas (XXII)-(XXIV). The cleavage moiety is of the formula Z-G-N($R^8$)$R^9$ where the cleaved compound is of one of general formulas (VII) to (IX). The method also includes allowing this cleavage moiety, Z-A-Z, Z-A-Z—$R^{18}$, and Z-G-N($R^8$)$R^9$, respectively, to be immobilized on the surface of the nanoparticulate tag by forming one of a covalent bond, a coordinative bond and a non-covalent interaction therewith via a Z atom, typically via at least one of its Z atoms. Further, the method includes determining the presence of beta-lactamase activity based on the presence of the cleavage moiety, Z-A-Z, Z-A-Z—$R^{18}$, and Z-G-N($R^8$)$R^9$, respectively, immobilized onto the surface of the nanoparticulate tag.

In an eighth aspect the present invention provides a method of identifying a beta-lactamase modulator. The method includes providing a sample with beta-lactamase activity. The method also includes contacting the sample with a compound suspected to have beta-lactamase modulatory activity. Further, the method includes contacting the sample with a nanoparticulate tag. The nanoparticulate tag includes a metal or a combination of metals, or it includes a nanotube of a metal, boron nitride and/or carbon. The nanoparticulate tag is capable of forming one of a covalent bond, a coordinative bond and a non-covalent interaction with a thio and/or a seleno group. The method further includes contacting the sample with a compound of one of general formulas (I)-(III) and (VII)-(IX) (supra). The method also includes allowing beta-lactamase activity in the sample to cleave a beta-lactam moiety of the compound of one of general formulas (I) to (III) and (VII) to (IX). As a result a cleavage moiety is released. The cleavage moiety is of one of the formulas Z-A-Z, Z-A-Z—$R^{15}$, Z-A-Z—$R^{16}$, and Z-A-Z—$R^{17}$ where the cleaved compound is of one of general formulas (I) to (III). The cleavage moiety is of the formula Z-G-N($R^8$)$R^9$ where the cleaved compound is of one of general formulas (VII) to (IX). The method also includes allowing this cleavage moiety, Z-A-Z, Z-A-Z—$R^{15}$, Z-A-Z—$R^{16}$, Z-A-Z—$R^{17}$ or Z-G-N($R^8$)$R^9$, respectively, to be immobilized on the surface of the nanoparticulate tag by forming a covalent bond, a coordinative bond or a non-covalent interaction therewith via a Z atom. Where the cleaved compound is of one of general formulas (I) to (III), the cleavage moiety Z-A-Z, Z-A-Z—$R^{15}$, Z-A-Z—$R^{16}$, and Z-A-Z—$R^{17}$, respectively is immobilized on the surface of the nanoparticulate tag by forming a covalent bond, a coordinative bond or a non-covalent interaction therewith via a Z atom, typically via at least one of its Z atoms. Where the cleaved compound is of one of general formulas (VII) to (IX), the cleavage moiety Z-G-N($R^8$)$R^9$ is immobilized on the surface of the nanoparticulate tag by forming a covalent bond, a coordinative bond and a non-covalent interaction therewith via the Z atom. Further, the method includes determining the presence of β-lactamase activity based on the presence of the cleavage moiety, Z-A-Z, Z-A-Z—$R^{15}$, Z-A-Z—$R^{16}$, Z-A-Z—$R^{17}$ or Z-G-N($R^8$)$R^9$, respectively, immobilized onto the surface of the nanoparticulate tag. The method thereby includes identifying β-lactamase modulatory activity of the candidate compound and identifying a β-lactamase modulator.

In a ninth aspect the present invention provides a method of identifying a β-lactamase modulator. The method includes providing a sample with beta-lactamase activity. The method also includes contacting the sample with a compound suspected to have β-lactamase modulatory activity. Further, the method includes contacting the sample with a nanoparticulate tag. The nanoparticulate tag includes a metal or a combination of metals, or it includes a nanotube of a metal, boron nitride and/or carbon. The respective metal is capable of forming one of a covalent bond, a coordinative bond and a non-covalent interaction with a thio and/or a seleno group. The method further includes contacting the sample with a compound of one of general formulas (VII)-(IX), (XXII)-(XXIV), (XXXIII), (XXXIV) and (XXXVI) (supra). The method also includes allowing β-lactamase activity in the sample to cleave a β-lactam moiety of the compound of one of general formulas (VII)-(IX), (XXII)-(XXIV), (XXXIII), (XXXIV) and (XXXVI). As a result a cleavage moiety is released. The cleavage moiety is of the formula Z-A-Z where the cleaved compound is of one of general formulas (XXXIII), (XXXIV) and (XXXVI). The cleavage moiety is of the formula Z-A-Z—$R^{18}$ where the cleaved compound is of one of general formulas (XXII)-(XXIV). The cleavage moiety is of the formula Z-G-N($R^8$)$R^9$ where the cleaved compound is of one of general formulas (VII) to (IX). The method also includes allowing this cleavage moiety, Z-A-Z, Z-A-Z—$R^{18}$, and Z-G-N($R^8$)$R^9$, respectively, to be immobilized on the surface of the nanoparticulate tag by forming a covalent bond, a coordinative bond or a non-covalent interaction therewith via a Z atom, typically via at least one of its Z atoms. Further, the method includes determining the presence of β-lactamase activity based on the presence of the cleavage moiety, Z-A-Z, Z-A-Z—$R^{18}$, and Z-G-N($R^8$)$R^9$, respectively, immobilized onto the surface of the nanoparticulate tag. The method thereby includes identifying β-lactamase modulatory activity of the candidate compound and identifying a β-lactamase modulator.

In a tenth aspect the present invention provides a kit for detecting β-lactamase activity in a sample. The kit includes a compound of one of general formulas (I)-(III) and (VII)-(IX) (supra). The kit also includes a nanoparticulate tag.

In an eleventh aspect the present invention provides a kit for detecting β-lactamase activity in a sample. The kit includes a compound of one of general formulas (VII)-(IX), (XXII)-(XXIV), (XXXIII), (XXXIV) and (XXXVI) (supra). The kit also includes a nanoparticulate tag.

A method of the invention is an easily operational method, in some embodiments a chromogenic method, based on a nanoparticulate tag that allows monitoring Bla activities for instance in vitro and in antibiotic resistant bacterial suspensions. This method can be used to rapidly identify β-lactamases or factors with a corresponding activity, and to screen β-lactamase inhibitors in a high-throughput fashion through e.g. the naked eye or a simple colorimetric reader.

BRIEF DESCRIPTION OF THE DRAWINGS

The invention will be better understood with reference to the detailed description when considered in conjunction with the non-limiting examples and the accompanying drawings.

FIG. 1A illustrates the design of the β-lactamase (Bla) assay based on detectable changes upon the immobilization of cleavage products on gold nanoparticles (Au-NPs). The embodiments depicted in FIG. 1A and FIG. 1E are further based on color changes during enzyme-induced aggregation of the nanoparticles. Exemplary linkers suitable for the substrate are shown in FIG. 1B. Further exemplary linkers that may be particularly suitable for substrates as depicted in FIG. 1E (linker 2) are shown in FIG. 1D. FIGS. 1C and 1E depict embodiments in which the substrate molecule contains only one cephem nucleus. In embodiments where the linker is connected to the moiety —Z—$R^8$ and where $R^8$ is different from H, the substrate is again not capable of forming a covalent bond to the nanoparticles (see FIG. 1C).

FIG. 2C depicts the synthesis of substrate 2 (see Example 2) from 4-aminothiophenol and 3,6-dioxaoctyl-1,8-diamine.

FIG. 9A-B depicts UV-Vis spectra of gold nanoparticles before (a) and after (b) incubation with Bla treated substrate 3 in the absence (FIG. 9A) and in the presence of an inhibitor (FIG. 9B). Vials with only gold nanoparticles (1 & 3) and with gold nanoparticles, Bla and substrate (2 & 4) are shown as insets.

FIG. 10A).

FIG. 11A-D depicts the colorimetric detection of Bla activity (P99) using substrate 3 in the absence and presence of different inhibitors (indicated below the sample, n.i.=no inhibitor) using gold nanoparticles and nitrocefin (indicated on the right). Appearance in blue (FIG. 11A), red (FIG. 11B) and yellow (FIG. 11C) is shown. FIG. 11D depicts the absorbance change of Bla inhibition assay in the absence and presence of different inhibitors (Inhibitor concentration: 0.1 μM).

FIG. 12A-C depicts the colorimetric detection of Bla activity using gold nanoparticles and substrate 3. Different inhibitors (indicated above the sample, n.i.=no inhibitor) were used on four β-lactam resistant bacteria that contained class A Bla (indicated on the right, I: transformed *E. coli*; II: TEM-1 *E. coli*; III: *B. cereus*; IV: *K. pneumoniae*). Appearance in blue (FIG. 12A), red (FIG. 12B) and yellow (FIG. 12C) is shown.

FIG. 13A-C depicts the colorimetric detection of Bla activity using substrate 3 and nitrocefin. The concentration of inhibitors (see FIG. 12) was maintained at 3.5 μM, which was larger than that used in the method employing nanoparticles. The same bacteria were used as in FIG. 12 (see above), color presented as in FIG. 12.

FIG. 14A-B depicts the aggregation kinetics of gold nanoparticles for Bla. FIG. 14A shows the absorbance change of a suspension of gold nanoparticles with time in the presence of Bla-pretreated substrates (5 μM): substrate 1 (■, see FIG. 2B), substrate 2 (●, see FIG. 2C). FIG. 14B shows the dependence of absorbance change over time for the interactions of free dithiol linkers (5 μM) with the suspension of gold nanoparticles.

FIG. 15 depicts the absorbance change at 650 nm of gold nanoparticles at 2 h after mixing 60 pm Bla-pretreated substrate 2 (8 μM) with various concentrations of gold particles (ranging from 0.65, 1.3, 2.2, 2.6, 3.0, 3.4, 4.0, 4.8, to 10.4 nm; analyses were performed in triplicate).

FIG. 16 depicts the absorbance at 620 nm of gold nanoparticles, in the presence of substrate 3 (8 pretreated for 20 min with a range of concentration of TEM-1 Bla.

FIG. 17A-C depicts the determination of $K_m$ and $K_{cat}$ for substrate 1 (FIG. 17A), substrate 2 (FIG. 17B) and substrate 3 (FIG. 17C) by means of a Lineweaver-Burk plot.

FIG. 22 depicts the coloring of a solution of nitrocefin in the absence or presence of different bacterial strains and substrate 2 (1: Nitrocefin only; 2: Nitrocefin+ with wild type *E. coli* Bl21; 3: Nitrocefin+β-lactam antibiotics resistant *E. coli* Bl21; 4: Nitrocefin+clinical isolate *K. pneumoniae* (ATCC 700603) strains).

DETAILED DESCRIPTION OF THE INVENTION

Figure 2A:
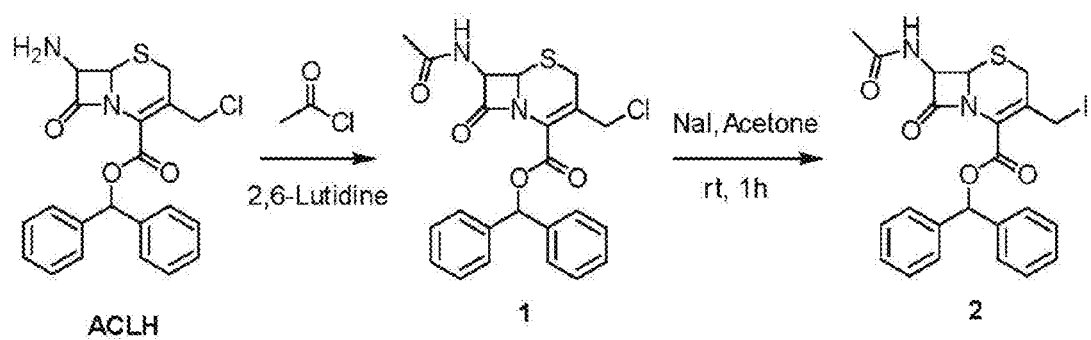
FIG. 2A depicts the synthesis of 2 from 7-Amino-3-chloromethyl cephalosporanic acid benzylhydryl ester hydrochloride (ACLH).

The compounds provided by the invention can be represented by one of general formulas (I)-(III) and (VII)-(IX):

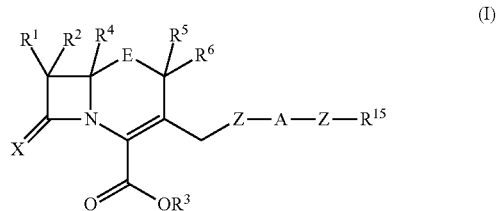

(I)

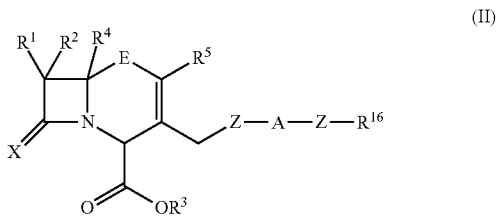

(II)

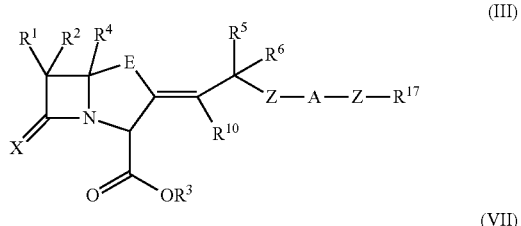

(III)

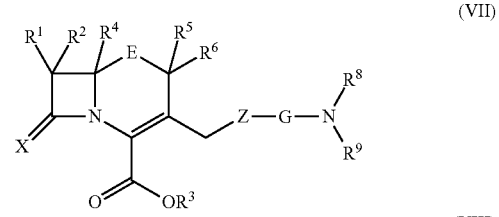

(VII)

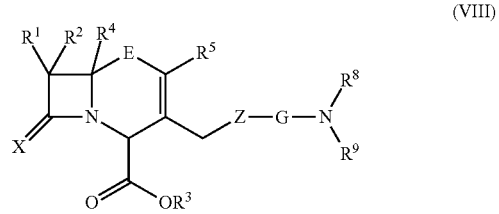

(VIII)

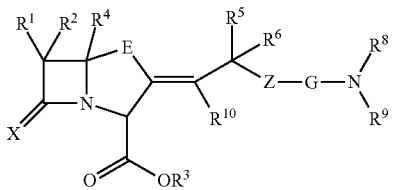

(IX)

In these general formulas $R^1$ may be H, a halogen atom,

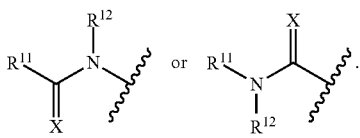

Any suitable halogen atom may be present, whether e.g. F, Cl, Br or I. X is O, S, Se or NH. $R^{11}$ and $R^{12}$ are independently selected hydrogen or an aliphatic, an alicyclic, an aromatic, an arylaliphatic, or an arylalicyclic group with a main chain of a length of 1 to about 20 carbon atoms, about 2 to about 20 carbon atoms, about 2 to about 15 carbon atoms or about 2 to about 10 carbon atoms. In addition the main chain may in some embodiments include 0 to about 3 heteroatoms, such as about 1, 2, or 3 heteroatoms. Examples of suitable heteroatoms include, but are not limited to, N, O, S, Se and Si.

The term "aliphatic" means, unless otherwise stated, a straight or branched hydrocarbon chain, which may be saturated or mono- or poly-unsaturated and include heteroatoms (see above). An unsaturated aliphatic group contains one or more double and/or triple bonds (alkenyl or alkynyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to about 5, to about 10, to about 15, to about 20, to about 30 or to about 40 carbon atoms. Examples of alkenyl radicals are straight-chain or branched hydrocarbon radicals which contain one or more double bonds. Alkenyl radicals normally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec.-butyl, tert.-butyl, neopentyl and 3,3-dimethylbutyl. Both the main chain as well as the branches may furthermore contain heteroatoms as for instance N, O, S, Se or Si or carbon atoms may be replaced by these heteroatoms.

The term "alicyclic" may also be referred to as "cycloaliphatic" and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted.

The term "aromatic" means an at least essentially planar cyclic hydrocarbon moiety of conjugated double bonds, which may be a single ring or include multiple fused or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, oxazolyl-, oxoninyl-, oxepinyl-, benzoxepinyl-, azepinyl-, thiepinyl-, selenepinyl-, thioninyl-, azecinyl-, (azacyclodecapentaenyl-), diazecinyl-, azacyclododeca-1,3,5,7,9,11-hexaene-5,9-diyl-, azozinyl-, diazocinyl-, benzazocinyl-, azecinyl-, azaundecinyl-, thia[11]-annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties include, but are not limited, to 1-ethyl-naphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethylphenyl)ethyl]-4-ethyl-quinazoline or 7,8-dibutyl-5,6-diethyl-isoquinoline.

As already indicated above, each of the terms "aliphatic", "alicyclic", "aromatic" and "arylaliphatic" as used herein is meant to include both substituted and unsubstituted forms of the respective moiety. Substituents may be any functional group such as —COOH (carboxy), —OH (hydroxy), —SH (thiol-), a dithiane-, —SeH (seleno-), —CHO (aldehyde), —CO— (carbonyl), —OSO— (sulfonyl), sulfo-, sulfido-, —O— (oxo), sulfate (—OSO$_3$H), —NH$_2$ (amino), —NO (nitro), —NS, —NSe, a halogen such as —Br (bromo), —Cl (chloro) or —F (fluoro), an amino-, an imino-, an amido-, an imido-, an azido-, a diazo-, a cyano-, an isocyano-, a thiocyano-, a nitro-, a nitroso-, asulfonyl- (e.g. a trifluoromethyl sulfonyl-, p-toluenesulfonyl-, bromobenzenesulfonyl-, nitrobenzenesulfonyl-, or a methane-sulfonyl), silyl-, silano- or a siloxy-group.

In the above general formulas $R^2$ is one of H, a halogen atom (see above), an aliphatic group, including e.g. a silyl group, an alicyclic group, an aromatic group, an arylaliphatic group and an arylalicyclic group, that includes 0 to about 3 heteroatoms selected from the group consisting of N, O, S, Se and Si. $R^2$ may for example be one of fluoro-, methyl, trifluoromethyl, tribromomethyl, ethyl, heptafluoroethyl, propyl, isopropyl, butyl, isobutyl, tert.-butyl, trimethylsilyl-, pentyl, cylcopentyl, isopentyl, neopentyl, hexyl, cylcohexyl, phenyl, pyridinyl, piperidinyl, 3,3-dimethylbutyl, heptyl, methylcyclohexyl, cycloheptyl, methylphenyl, octyl, cyclooctyl, dimethylcyclohexyl, dimethylphenyl, nonyl, decyl, diphenylmethyl, triphenylmethyl and naphtyl.

$R^3$ and $R^8$ to $R^{10}$ in the above general formulas are independently selected H, or one of an alicyclic group (also called "cycloaliphatic"), an aromatic group, an arylaliphatic group and an arylalicyclic group (also called "arylcycloaliphatic") with a main chain of a length of 1 to about 40 carbon atoms, such as 1 to about 20 carbon atoms, about 2 to about 20 carbon atoms, about 2 to about 15 carbon atoms or about 2 to about 10 carbon atoms. In addition the main chain may in some embodiments include 0 to about 3 heteroatoms, such as about 1, 2, or 3 heteroatoms. Examples of suitable heteroatoms include, but are not limited to, N, O, S, Se and Si.

$R^4$ to $R^6$ in the above general formulas are independently selected H, fluoro-, or one of an alicyclic group an aromatic group, an arylaliphatic group and an arylalicyclic group (also called "arylcycloaliphatic") with a main chain of a length of 1 to about 40 carbon atoms, such as 1 to about 20 carbon atoms, about 2 to about 20 carbon atoms, about 2 to about 15 carbon atoms or about 2 to about 10 carbon atoms. In addition the main chain may in some embodiments include 0 to about 3 heteroatoms, such as about 1, 2, or 3 heteroatoms. Examples of suitable heteroatoms include, but are not limited to, N, O, S, Se and Si.

$R^{15}$ in above general formula (I) as well as $R^{16}$ in above general formula (II) and $R^{17}$ in above general formula (III) are independently selected H, an aliphatic group, an alicyclic group, an aromatic group, an arylaliphatic group or an arylalicyclic group, which includes 0 to about 5 heteroatoms selected from the group consisting of N, O, S, Se and Si. In some embodiments $R^{15}$ in formula (I), $R^{16}$ in formula (II) and $R^{17}$ in formula (III) are independently selected from one of the following moieties:

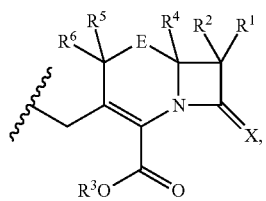

(IV)

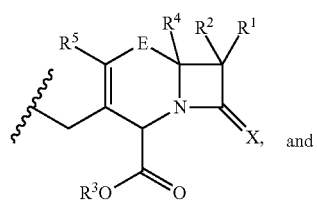

(V)

and

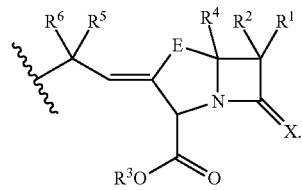

(VI)

In these moieties $R^1$ to $R^5$, X, and in moieties (IV) and (VI) $R^8$ to $R^{10}$ are as defined above (for E see below). Accordingly, in some embodiments the compound of general formula (I) is a compound of one of formulas (XXXII), (XXXIII) or (XXXIV):

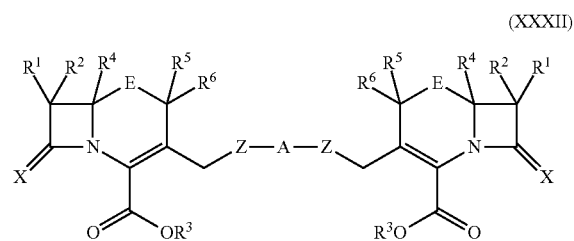

(XXXII)

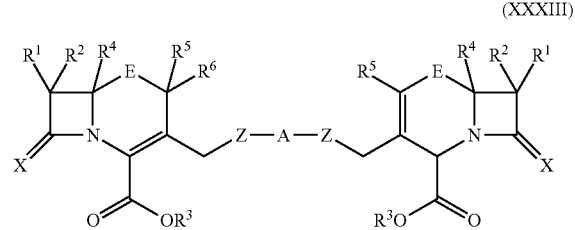

(XXXIII)

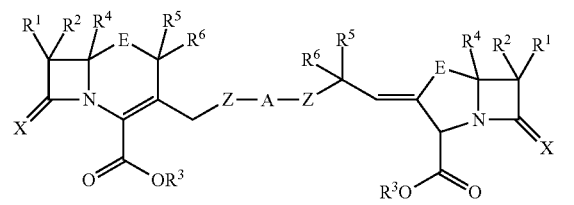

(XXXIV)

In these formulas $R^1$ to $R^5$ and in formulas (XXXIII) and (XXXIV) $R^6$ are as defined above (for E see below). In some embodiments the compound of general formula (II) is a compound of one of formulas (XXXV) or (XXXVI):

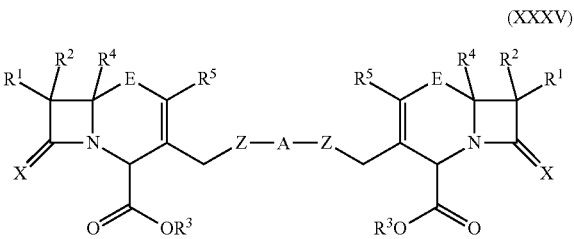

(XXXV)

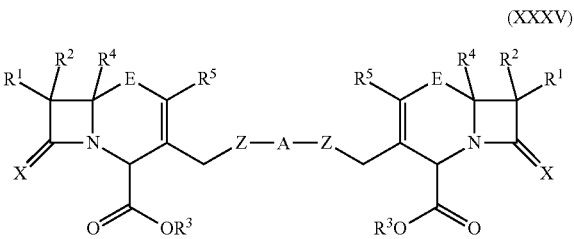

-continued

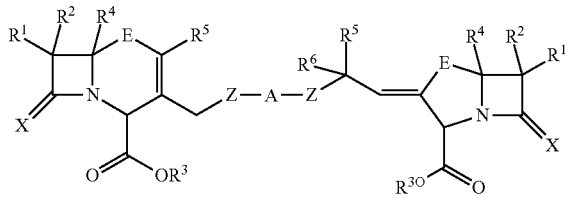
(XXXVI)

The compounds of formula (XXXIII) may also be regarded as compounds of general formula (II), and the compounds of formulas (XXXIV) and (XXXVI) can also be seen as compounds of general formula (III). Again, $R^1$ to $R^5$ in formulas (XXXV) to (XXXVII) and $R^6$ in formula (XXXVI) are as defined above (for E see below). In some embodiments the compound of general formula (III) is a compound of formula (XXXVII):

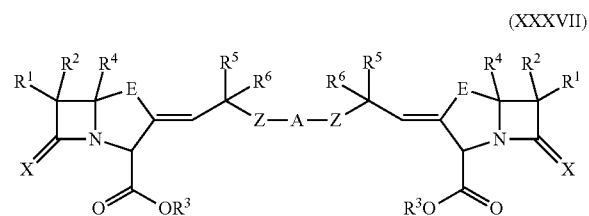
(XXXVII)

In the above formulas, including moieties (IV) to (VI), E is S, SO, $SO_2$ or $CH_2$. Z is sulphur, S, or selenium, Se. X in general formulas used herein is O, S, or NH. A in the above general formulas is a bridge that in formulas (I) to (III) connects two sulfur, two selenium or a selenium and a sulfur atom. In formulas (I) to (III) it may further connect two sulfur, two selenium or a selenium and a sulfur atom. Generally the bridge is linear or branched. The bridge is defined by an aliphatic, alicyclic, aromatic, arylaliphatic, or arylalicyclic radical with a main chain of 1 to about 60 carbon atoms, such as 1 to about 50 carbon atoms, 1 to about 40 carbon atoms, 1 to about 30 carbon atoms, 1 to about 20 carbon atoms, about 2 to about 20 carbon atoms, 1 to about 15 carbon atoms, about 2 to about 15 carbon atoms, about 1 to about 10 carbon atoms, about 2 to about 10 carbon atoms or about 1 to about 5 carbon atoms. In embodiments where the main chain of the bridge A includes one or more cyclic structures such as an alicyclic or aromatic ring, the main chain of a respective alicyclic, aromatic, arylaliphatic or aryl alicyclic radical is taken to include that ring portion or those ring portions that is/are defined by the smallest number of atoms that are part of the cyclic structure(s). In addition the main chain may in some embodiments include 0 to about 50 heteroatoms, such as 0 to about 40 heteroatoms, 0 to about 30 heteroatoms, 0 to about 20 heteroatoms, 0 to about 25 heteroatoms, 0 to about 18 heteroatoms or 0 to about 12 heteroatoms, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 heteroatoms. Examples of suitable heteroatoms include, but are not limited to, N, O, S, Se and Si.

In typical embodiments the atom of the bridge A that is covalently bonded to an atom Z, i.e. in for instance formulas (I)-(III), (XXII)-(XIV), (XXXIV) or (XXXVI), is a carbon atom. Likewise, in typical embodiments the atom of the bridge G that is covalently bonded to the respective atom Z, i.e. in for instance formulas (VII)-(IX), is a carbon atom. In some embodiments this atom of the bridge A or of the bridge G that is covalently bonded to an atom Z is an unsubstituted carbon atom such as a methylene group. In some embodiments the atom of the bridge A or G that is covalently bonded to an atom Z is part of an aromatic ring, which may for instance be part of an aromatic or of an arylaliphatic bridge A or G. In some embodiments such a bridge A or G is different from a benzene ring, or different from an unsubstituted benzene ring. In typical embodiments the atom of the bridge G that is covalently bonded to the nitrogen atom (N), e.g. in formulas (VII)-(IX), is also a carbon atom. In some embodiments this atom of the bridge G that is covalently bonded to the nitrogen atom is an unsubstituted carbon atom such as a methylene group. In some embodiments the atom of the bridge G that is covalently bonded to the nitrogen atom is part of an aromatic ring, which may for instance be part of an aromatic or of an arylaliphatic bridge G. In some embodiments such a bridge G is different from a benzene ring, or different from an unsubstituted benzene ring.

In some embodiments the bridge A is or includes an arylaliphatic moiety of the structure ar-Q-ar. In this structure ar is an aromatic radical such as benzyl or naphthyl (see above for examples of aromatic moieties). Q is an aliphatic or an alicyclic radical with a main chain of 1 to about 50 carbon atoms, such as 1 to about 40 carbon atoms, 1 to about 30 carbon atoms, 1 to about 20 carbon atoms, 2 to about 20 carbon atoms, about 1 to about 15 carbon atoms, about 2 to about 15 carbon atoms, about 1 to about 10 carbon atoms, about 2 to about 10 carbon atoms or about 1 to about 5 carbon atoms. In embodiments where the main chain of the radical Q includes one or more alicyclic structures, the main chain of a respective cyclic, radical is taken to include that ring portion or those ring portions that is/are defined by the smallest number of atoms that are part of the cyclic structure(s). In some embodiments the main chain of radical Q includes 0 to about 50 heteroatoms, e.g. N, O, S, Se and Si, such as 0 to about 40 heteroatoms, 0 to about 30 heteroatoms, 0 to about 20 heteroatoms, 0 to about 25 heteroatoms, 0 to about 16 heteroatoms, 0 to about 14 heteroatoms, or 0 to about 12 heteroatoms, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 heteroatoms.

In some embodiments the bridge A is or includes an arylaliphatic moiety of the structure ar-J-Q-M-ar. In this structure ar and Q are as defined above. J and M are each an independently selected aliphatic spacer with a main chain of 0 to about 10 carbon atoms, such as 0 to about 8, 0 to about 6 or 0 to about 3 carbon atoms, for example 1, 2, 3, 4, 5, 6, 7, 8, 9 or 10 carbon atoms. The main chain of the spacer J and of the spacer M may furthermore include 0 to about 3, such as 1, 2, or 3 heteroatoms, e.g. N, O, S, Se or Si. In some embodiments J and M are identical. In such embodiments the bridge can be represented by the structure ar-J-Q-J-ar.

In some embodiments the bridge A is or includes an arylaliphatic moiety of the structure J-Q-M. Q, J and M are as defined above. In embodiments where J and M are identical, the corresponding bridge can also be represented by the structure J-Q-J. In some embodiments the bridge A is of the structure, or includes the structure, J-ar-M with J, M and ar as defined above.

In some embodiments the bridge A is of symmetrical structure in that it can be taken to consist of two identical molecular halves connected by a covalent bond. As an illustrative example, the radical Q in the structure ar-Q-ar or in the structure J-Q-J may be a radical of the general structure —[O—CH$_2$—CH$_2$—O—]$_n$, with n being an integer from 0 to about 20, including 0 to about 10, such as 1, 2, 3, 4, 5, 6, 7, 8, 9, 10, 11, 12, 13, 14, 15, 16, 17, 18, 19 or 20.

In some embodiments the main chain of the bridge A includes an amide bond. Accordingly, in such embodiments the main chain of the bridge A includes nitrogen as a heteroatom, which is linked to a carbonyl group. Examples of a suitable bridge that includes an amide bond include, but are not limited to, the radicals based on the dithiol compound with Chemical Abstracts-No1003885-20-8, on 16-mercapto-N-(2-mercaptoethyl)-hexadecanamide (CAS-No 937395-11-4), N,N'-bis(2-mercaptoethyl)-decanediamide (CAS-No 53162-32-6), N,N'-1,10-decanediylbis[3-mercapto-propanamide (CAS-No 150235-72-6), mercapto[(mercaptoacetyl)amino]-acetic acid ethyl ester (CAS-No 77581-01-2), N,N'-1,5-pentanediylbis[3-mercapto-propanamide (CAS-No 900528-29-2), N,N'-1,7-heptanediylbis[3-mercapto-propanamide (CAS-No 9005 28-31-6), N,N'-bis(2-mercaptoethyl)-nonanediamide (CAS-No 10216-25-8), 2,2'-oxybis[N-(2-mercaptoethyl)-acetamide (CAS-No 441353-71-5), 2-mercapto-N-(5-mercaptopentyl)-butanamide (CAS-No 866132-89-0), 2-mercapto-N-(4-mercaptobutyl)-pentanamide (CAS-No 866133-06-4) and 2-mercapto-N-(3-mercaptopropyl)-pentanamide (CAS-No 866133-04-2). In some embodiments the bridge is one of the radicals depicted in FIG. 1B or FIG. 1D. Where the variable n in subscript is used in these examples n is an integer from 0 to about 20, such as 1, 2, 3, 4, 5, 6, 7, 8, 9, 10, 11, 12, 13, 14, 15, 16, 17, 18, 19 or 20.

The bridge A together with the atoms which it connects, such as the two sulfur, two selenium or the selenium and the sulfur atoms, may be taken to define a linking moiety Z-A-Z in formulas (I)-(VI), and (XXXII)-(XXXVIII). This linking moiety may be taken to be a radical of a corresponding bifunctional compound, e.g., a dithiol or diselenol. In the linking moiety Z-A-Z the bonds between the bridge A and the first atom Z as well between the bridge A and the second atom Z are understood to be single bonds. Furthermore, while the bridge A may include any number of desired cyclic structures, the linking moiety Z-A-Z as a whole is understood to define a linear structure. Accordingly, theoretical embodiments in which the first and the second atom Z might be directly linked to form a ring, or in which $R^{15}$ in general formula (I), $R^{16}$ in general formula (II) and $R^{17}$ in general formula (III) might be linked back into the bridge A by forming a cyclic structure are not encompassed by the invention.

The linking moiety Z-A-Z joins in formulas (XXXII), (XXXV) and (XXXVII) two identical molecular units, each generally including a 4-thia-1-azabicyclo[3.2.0]heptane-2-carboxylic acid, a 5-thia-1-azabicyclo[4.2.0]oct-2-ene-2-carboxylic acid or a 5-thia-1-azabicyclo[4.2.0]oct-3-ene-2-carboxylic acid unit (e.g. a cephem nucleus such as a cephalosporanic moiety). In formulas (XXXIII), (XXXIV) and (XXXVI) the linking moiety Z-A-Z joins two such molecular units that differ from each other, such as one 4-thia-1-azabicyclo[3.2.0]heptane-2-carboxylic acid unit and one 5-thia-1-azabicyclo[4.2.0]oct-2-ene-2-carboxylic acid unit. In some embodiments of formulas (I)-(III) the linking moiety Z-A-Z joins one such molecular unit to an aliphatic, aromatic, alicyclic or arylalicyclic moiety.

For the sake of clarity it is noted that this linking moiety often differs from the cleavage moiety, which may be released from a molecule of a compound of the invention upon exposure to β-lactamase activity (see below). In embodiments where a compound of the invention includes only one β-lactam ring, for instance where $R^{15}$ of a compound of general formula (I) or $R^{16}$ of a compound of general formula (II) does not include a β-lactam ring, being for instance different from bicyclic moieties (IV)-(VI), only the portion of the molecule with the β-lactam ring may be cleaved by β-lactamase activity. The residual structure of the compound remains in such a case intact and accordingly becomes a part of the cleavage moiety. As an example, $R^{15}$ of a compound of general formula (I) or $R^{16}$ of a compound of general formula (II) is typically also included in a cleavage moiety formed from a compound of general formula (I) and general formula (II), respectively, if it does not have a β-lactam ring.

In formulas (VII)-(IX) the bridge G together with the atoms which it connects, i.e., one sulfur or selenium atom and one nitrogen atom, may likewise be taken to define a linking moiety, which is of the formula Z-G-N. This linking moiety may also be taken to be a radical of a corresponding bifunctional compound, e.g., an aminothiol or an aminoselenol. In formulas (VII)-(IX) the linking moiety Z-G-N joins one molecular unit that generally includes a 4-thia-1-azabicyclo[3.2.0]heptane-2-carboxylic acid, a 5-thia-1-azabicyclo[4.2.0]oct-2-ene-2-carboxylic acid or a 5-thia-1-azabicyclo[4.2.0]oct-3-ene-2-carboxylic acid unit and moieties $R^8$ and $R^9$.

The bridge G in the above formulas (VII) to (IX) connects the sulfur or selenium atom of the corresponding moiety to a nitrogen atom. On a general basis the above explanations with regard to the bridge A also apply to the bridge G. Accordingly, in some embodiments the bridge A falls under the above definition of the bridge A. In such embodiments the general formulas (VII) to (IX) could also be represented by the general formulas (VIIa) to (IXa):

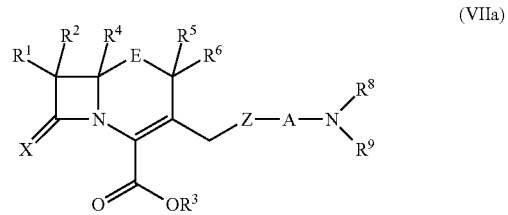

(VIIa)

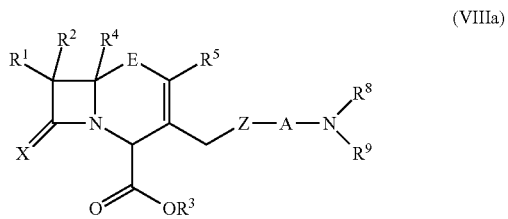

(VIIIa)

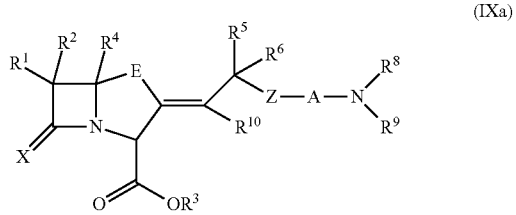

(IXa)

In these general formulas R¹ to R⁵, R⁶ in formulas (VIIa) and (IXa), R⁸ and R⁹, and in formula (IXa) R¹⁰ are as defined above. Further, as noted for the linking moiety Z-A-Z, in the linking moiety Z-G-N the bonds between the bridge G and the atom Z as well between the bridge G and the nitrogen atom are understood to be single bonds. The linking moiety Z-G-N as a whole is also understood to define a linear structure that does not form a cyclic structure, despite the fact that the bridge G may include one or more cyclic structures (see also above).

In some embodiments the bridge G is or includes an arylaliphatic moiety of the structure ar-J-Q-M. J, Q, M and ar are as defined above.

In some embodiments $R^{15}$ in above general formula (I) as well as $R^{16}$ in above general formula (II) and $R^{17}$ in above general formula (III) are independently selected from an aliphatic group, an aromatic group, an arylaliphatic group, an arylalicyclic group or a monocyclic alicyclic group. The respective moiety, $R^{15}$ in above general formula (I), $R^{16}$ in above general formula (II) and $R^{17}$ in above general formula (III), can in such embodiments also be represented as $R^8$. This symbol is understood to serve in simplifying distinguishing the various embodiments encompassed by the invention.

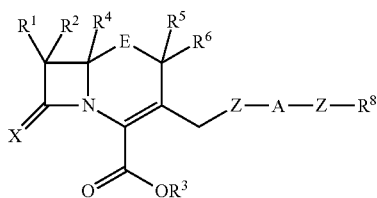
(IV)

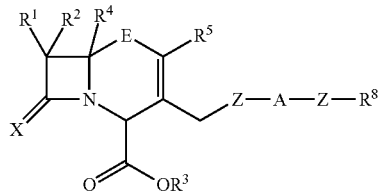
(V)

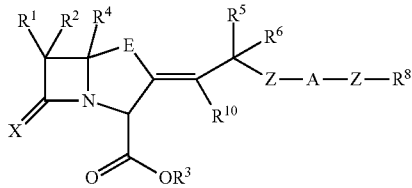
(VI)

In some embodiments the invention provides a compound of one of general formulas (X)-(XII):

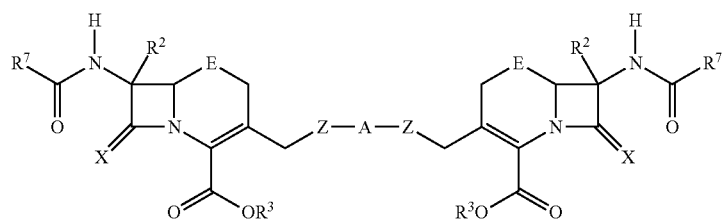
(X)

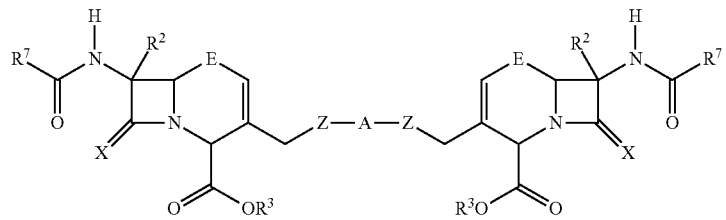
(XI)

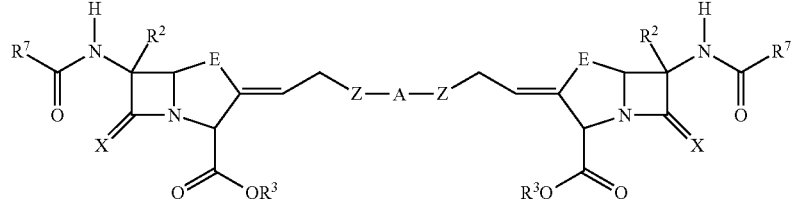
(XII)

In these general formulas (X)-(XII) $R^7$ is an aliphatic, alicyclic, aromatic, arylalicyclic, or an arylalicyclic group. $R^2$ and $R^3$ are independently selected H or one of a alicyclic group, an aromatic group, an arylaliphatic group and an arylalicyclic group with a main chain of a length of 1 to about 20 carbon atoms, such as about 2 to about 20 carbon atoms, about 2 to about 15 carbon atoms, about 2 to about 10 carbon atoms or about 1 to about 5 carbon atoms. In addition the main chain may in some embodiments include 0 to about 3 heteroatoms, such as about 1, 2, or 3 heteroatoms. Examples of suitable heteroatoms include, but are not limited to, N, O, S, Se and Si. Furthermore, $R^2$ may be a halogen atom, such as fluoro-, chloro-, bromo- or iodo.

In some embodiments the invention provides a compound of one of general formulas (XIII)-(XVIII):

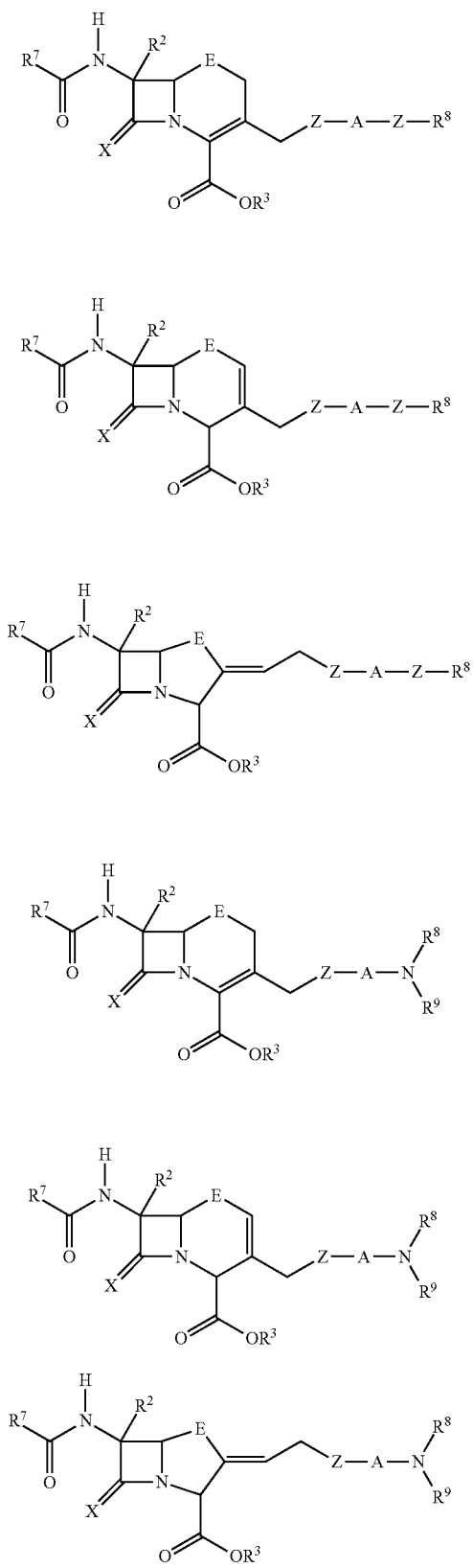

As three further examples, the following compounds are also encompassed by the invention:

In general formulas (XIII)-(IXX), (LVIII) and (IXXX) $R^2$-$R^5$, in formulas (IXX), (LVIII) and (IXXX) $R^6$, in formulas (XIII)-(IXX) $R^7$, in formulas (XIII)-(XVIII) $R^8$, and in formulas (XVI)-(XVIII) $R^9$, are as defined above.

A variety of moieties have already been shown to be suitable groups that may be part of cephem nuclei and that may accordingly serve as illustrative examples of moieties that may be included in a compound of general formulas (I) to (III), (VII) to (IX), (IXXX) and (VVIII). $R^7$ in formulas (X) to (IXX), (XXVII) and (IXXX) may for instance be methyl as in 7-acetamido-3-(mercaptomethyl)-8-oxo-5-thia-1-azabicyclo[4.2.0]oct-2-ene-2-carboxylic acid (Chemical Abstracts No. 875216-86-7) or 4-[[[7-(acetylamino)-2-carboxy-8-oxo-5-thia-1-azabicyclo[4.2.0]oct-2-en-3-yl] methyl]thio]-1-(methylamino)-pyridinium (CAS No. 164299-89-2), H as in 7-(formylamino)-8-oxo-3-[(phenylthio)methyl]-5-thia-1-azabicyclo[4.2.0]oct-2-ene-2-carboxylic acid (CAS No. 105805-48-9), 2-propenyl as in 7-(3-butenamido)-3-[(methylthio)methyl]-8-oxo-5-thia-1-azabicyclo[4.2.0]oct-2-ene-2-carboxylic acid (CAS No. 26622-80-0), cyanomethyl as in 7-(2-cyanoacetamido)-3-[(methylthio)methyl]-8-oxo-5-thia-1-azabicyclo[4.2.0]oct-2-ene-2-carboxylic acid (CAS No. 26622-83-3), (methylthio)methyl as in 7-[2-(methylthio)acetamido]-3-[(methylthio)methyl]-8-oxo-5-thia-1-azabicyclo[4.2.0]oct-2-ene-2-carboxylic acid (CAS No. 26622-81-1), benzyl as in 3-(mercaptomethyl)-8-oxo-7-[(phe-nylacetyl)amino]-5-thia-1-azabicyclo[4.2.0]oct-2-ene-2-carboxylic acid (CAS No. 56654-72-9) or in 3-[(amidinothio)methyl]-8-oxo-7-(2-phenylacetamido)-5-thia-1-azabicyclo[4.2.0]oct-3-ene-2-carboxylic acid (CAS No. 7629-53-0), 2-chloroethyl as in 7-[(chloroacetyl)amino]-8-oxo-3-(thiocyanatomethyl)-5-thia-1-azabicyclo[4.2.0]oct-2-ene-2-carboxylic acid (CAS No. 164718-98-3) or 2-thienyl-methyl as in 3-[[(aminoiminomethyl)thio]methyl]-8-oxo-7-[(2-thienylacetyl)amino]-5-thia-1-azabicyclo[4.2.0]oct-3-ene-2-carboxylic acid (CAS No. 40 704-40-3).

$R^1$ in formulas (I) to (III), (VII)-(IX), (XXII)-(XXIV), (XXXIII), (XXXIV) and (XXXVI) may for example be amino as in 7-amino-3-(mercaptomethyl)-8-oxo-5-thia-1- azabicyclo[4.2.0]oct-2-ene-2-carboxylic acid (CAS No. 56654-74-1), 7-amino-3-(mercaptomethyl)-8-oxo-1-azabicyclo[4.2.0]oct-2-ene-2-carboxylic acid (CAS No. 183385-66-2), 7-amino-3-[(methylthio)methyl]-8-oxo-1-azabicyclo [4.2.0]oct-2-ene-2-carboxylic acid (CAS No. 183427-82-9), 7-amino-3-[(ethylthio)methyl]-8-oxo-1-azabicyclo[4.2.0] oct-2-ene-2-carboxylic acid (CAS No. 183427-83-0, the (6R-trans) compound has CAS-No 80195-44-4), 7-amino-8-oxo-3-[(thiosulfeno)methyl]-1-azabicyclo[4.2.0]oct-2-ene-2-carboxylic acid (CAS No. 183426-68-8, the (6R-trans) compound has CAS-No 183426-26-8), (6R-trans)-7-amino-3-[(methyl thio)methyl]-8-oxo-5-thia-1-azabicyclo [4.2.0]oct-2-ene-2-carboxylic acid (CAS No. 26805-12-9), 1-hydroxyethyl as in 6-(1-hydroxyethyl)-3-(mercaptomethylene)-7-oxo-4-thia-1-azabicyclo[3.2.0]heptane-2-carboxylic acid (CAS No. 100239-36-9), or (6R-trans)-7-amino-8-oxo-3-(thiocyanatomethyl)-5-thia-1-azabicyclo[4.2.0]oct-2-ene-2-carboxylic acid (CAS No. 90211-12-4), or H as in 3-[2-(methylthio)ethylidene]-7-oxo-4-thia-1-azabicyclo [3.2.0]heptane-2-carboxylic acid (the potassium salt has CAS No. 73761-01-0).

The compounds disclosed herein may for instance be a Cephalosporin derivative, a Cefotetan derivative, a Cefmetazole derivative or a Latamoxef derivative. In the above general formulas E, X, Z and A are as defined above.

The compounds encompassed by the present invention generally have a plurality of chiral centers (also termed stereogenic centers) and can thus exist not only in the form of a racemic mixture or in the meso form, but also in both enriched and pure enantiomers and enriched and pure diastereomers. Any respective stereochemical configuration and mixture thereof is encompassed by the above general formulas. A general introduction into the theoretical number of stereoisomers and their nomenclature can for instance be found in March's Advanced Organic Chemistry (Smith, M. B., March, J., Sixth Edition, 2007, Wiley-Interscience, pages 164-166). In some embodiments two enriched or isolated diastereomers of the same of one of the above structural formulas may be provided together or in parallel. Both cis- and trans-carbapenems are for instance known to possess antibacterial activity.

As an example, the configuration of the bicyclic moieties of the compounds of formula (I), (II) and (III) may be as depicted in structural formulas (Ia), (IIa) and (IIIa):

(Ia)

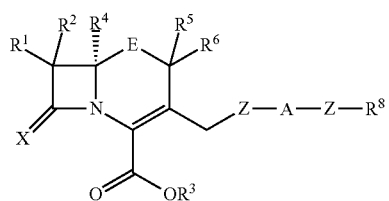

(IIa)

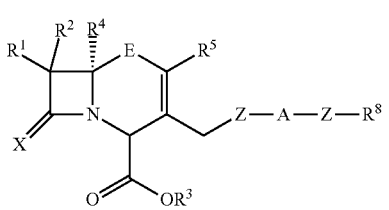

(IIIa)

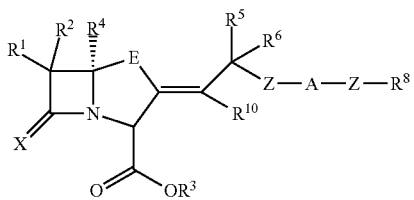

In the above structure representations the well-established wedge representation is used to define the stereochemical configuration of the bicyclic moieties. The wedge representation defines one orientation of a substituent relative to another substituent and relative to a ring structure (see e.g. Pine, Hendrickson, Cram, Hammond: Organic Chemistry, McGraw-Hill, 4th edition, 1981, pages 97-99 & 115-119). By defining nonsuperimposable mirror images the absolute stereochemistry can accordingly be derived from the respective wedge representation. According to the Cahn-Ingold-Prelog system (R,S system) of nomenclature the chiral center defined by the carbon atom carrying $R^4$ of the bicyclic moieties above is in all three formulas, i.e. (Ia), (IIa) and (IIIa), of the (R) configuration if $R^4$ is H. The Cahn-Ingold-Prelog system of nomenclature can however not appropriately be applied on a general basis to the depicted compounds, since this system is based on the ranking of substituents, e.g. H<C<N<O or $CH_3$-<$C_2H_5$-<$CH_2$=CH— (see also e.g. March's Advanced Organic Chemistry, supra, pages 155-158). A compound with the same wedge representation is thus in some embodiments called (R) and in other embodiments (S), depending on the nature of the relevant substituents(s). As an example, according to the Cahn-Ingold-Prelog system of nomenclature a compound may in some embodiments termed the (S,S)- and in some embodiments the (R,R)-diastereomer, depending on the selected substituents of a specific embodiment. As a further note the configuration of the carboxyl substituents in formula (IIa) may be both (R) and (S) and the relative orientation of e.g. $R^1$ and $R^2$ may likewise be (R) or (S). Depending on the substituents $R^1$ and $R^2$, the wedge representation may respectively differ. An indication on the configuration of such and other chiral centers has however been omitted from formulas (Ia), (IIa) and (IIIa) for sake of clarity.

As a further example, diastereomers of a compound of general formula (XXXIII) include inter alia structures that can be represented by the following two formulas (XXXIIIa) and (XXXIIIb):

(XXXIIIa)

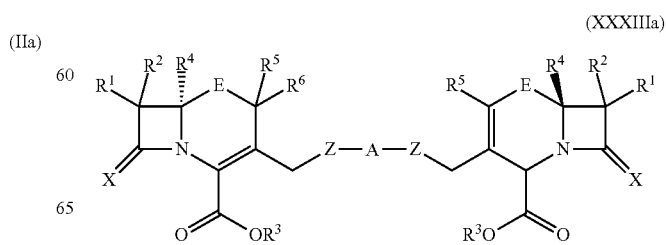

-continued

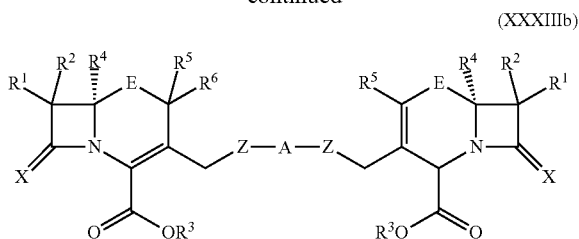
(XXXIIIb)

It is noted in this regard that (5R,6S)-rel-7-oxo-6-[(phenylacetyl)amino]-1-azabicyclo[3.2.0]hept-2-ene-2,3-dicarboxylic acid 3-methyl 2-[1,1,2,2-tetrachloro-2-[[[(5R,6R)-7-oxo-3-phenyl-6-[(phenylacetyl)amino]-1-azabicyclo [3.2.0]hept-2-en-2-yl]carbonyl]oxy]ethyl]ester, which includes a trans carbapenem and a cis carbapenem moiety, has been shown to possess excellent activity against β-lactamase producing microorganisms, including activity against *X. maltophilia* GN 12873 and *S. aureus* 95 (Hakimelahi, G. H., et al., *European Journal of Medicinal Chemistry* (2005) 40, 4, 339-349). Accordingly, compounds with two bicyclic moieties, e.g., units selected from a 4-thia-1-azabicyclo [3.2.0]heptane-2-carboxylic acid derivative, a 5-thia-1-azabicyclo[4.2.0]oct-2-ene-2-carboxylic acid derivative or a 5-thia-1-azabicyclo[4.2.0]oct-3-ene-2-carboxylic acid derivative, may be selected in a variety of stereochemical combinations, with an independently selected stereochemistry of each bicyclic moiety.

The stereochemistry of the respective compound may be analysed according to any method known in the art, such as for instance 2D-NMR based on homo- or heteronuclear J-coupling values (Riccio, R., et al., *Pure Appl. Chem.* (2003) 75, 2-3, 295-308), electron ionisation mass spectrometry, polarimetry, circular dichroism spectroscopy (e.g. using the split Cotton-effect based on the Davydov splitting, see e.g. Allemark, S. G., *Nat. Prod. Rep.* (2000) 17, 145-155), enantioselective chromatography, derivatization in combination with standard analytical techniques such as NMR, including any suitable 2D-NMR technique, for example based on the nuclear Overhauser effect, as well as X-ray crystallography or solid state NMR (see e.g. Harper, J. K., et al., *J. Org. Chem.* (2003) 68, 4609-4614).

The compounds of general formulas (I) to (III), (VII)-(XIV), (IXX), (XXV)-(XXVII), (IXXX), (XXXIII), (XXXIV), (XXXVI) and (LVIII) may be formed from a compound that includes the respective beta-lactam ring containing bicyclic moiety, such as a Clavulanic acid derivative or a cephalosporin derivative, and a suitable leaving group. The leaving group(s) of one or two molecules of such a compound may be replaced by a desired cleavage moiety upon reaction with a compound of the general formula $R^{14}$—Z-A-Z—$R^{14}$. In this formula $R^{14}$ is one of an aliphatic, an alicyclic, an aromatic, an arylaliphatic, and an arylalicyclic group, that includes 0 to about 3 heteroatoms selected from N, O, S, Se and Si.

Likewise, the compounds of general formulas (VII) to (IX) may be formed from a compound that includes the respective beta-lactam ring containing bicyclic moiety (supra). The leaving group of a molecule of such a compound may be replaced by a desired cleavage moiety upon reaction with a compound of the general formula (LII)

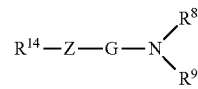
(LII)

In this formula (LII) $R^8$, $R^9$ and $R^{14}$ are as defined above. As an example, a compound of general formula (XX) may be provided:

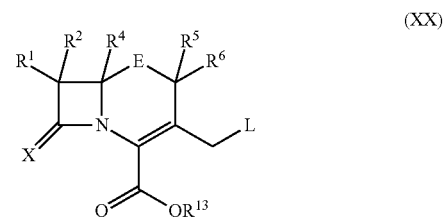
(XX)

L in this formula (XX) may be any suitable leaving group familiar to those skilled in the art, such as halogen, for instance F, Cl, Br or I, cyano, thiocyano, trifluoromethyl sulfonyl, p-toluenesulfonyl, bromobenzenesulfonyl, nitrobenzenesulfonyl, methanesulfonyl or azido. $R^{13}$ in formula (XX) may be an aliphatic, an alicyclic, an aromatic, an arylaliphatic or an arylalicyclic group, that includes 0 to about 3 heteroatoms selected from N, O, S, Se and Si. In some embodiments $R^{13}$ is identical to $R^3$ (see above). In some embodiments $R^{13}$ is converted to $R^3$, for instance before, during or after the reaction with a compound of formula $R^{14}$—Z-A-Z—$R^{14}$. A reaction of a compound of general formula (XX) and a compound of formula $R^{14}$—Z-A-Z—$R^{14}$ generally results in the formation of a compound of general formula I (supra).

Suitable examples of a compound of general formula (XX) include, but are not limited to, an ester of 7-(acetylamino)-3-(chloromethyl)-8-oxo-5-thia-1-azabicyclo[4.2.0] oct-2-ene-2-carboxylic acid (CAS-No 873431-19-7), of β-(bromomethyl)-7-(chloroacetylamino)-8-oxo-5-thia-1-azabicyclo[4.2.0]oct-2-ene-2-carboxylic acid (CAS-No 164718-91-6), of 3-(chloromethyl)-7-(formylamino)-8-oxo-5-thia-1-azabicyclo[4.2.0]oct-2-ene-2-carboxylic acid CAS-No 127388-96-9) or of 7-(chloroacetylamino)-3-(chloromethyl)-8-oxo-5-thia-1-azabicyclo[4.2.0]oct-2-ene-2-carboxylic acid (CAS-No 873431-19-7). Examples of a compound of general formula (XX) include, but are not limited to, (6R-trans)-7-(benzoylamino)-3-(bromomethyl)-8-oxo-5-thia-1-azabicyclo[4.2.0]oct-2-ene-2-carboxylic acid methyl ester (CAS-No 151413-37-5), (6R,7R)-3-(bromomethyl)-8-oxo-7-[(phenylacetyl)amino]-5-thia-1-azabicyclo[4.2.0]oct-2-ene-2-carboxylic acid (4-methoxyphenyl) methyl ester 5-oxide (CAS-No 625380-81-6), (6R,7R)-7-[[(2Z)-(5-amino-1,2,4-thiadiazol-3-yl)(ethoxyimino)acetyl] amino]-3-(bromomethyl)-8-oxo-5-thia-1-azabicyclo[4.2.0] oct-2-ene-2-carboxylic acid diphenylmethyl ester (CAS-No 676125-23-8), (6R,7R)-3-(chloromethyl)-7-[[2-[[(1,1-dimethylethoxy)carbonyl]amino]acetyl]amino]-8-oxo-5-thia-1-azabicyclo[4.2.0]oct-2-ene-2-carboxylic acid diphenylmethyl ester (CAS-No 935278-19-6), [6R-[6a,7b(R*)]]-3-(bromomethyl)-7-[[(3,4-dihydroxyphenyl)[[(4-ethyl-2,3-dioxo-1-piperazinyl)carbonyl]amino]acetyl]amino]-7-(formylamino)-8-oxo-5-thia-1-azabicyclo[4.2.0]oct-2-ene-2-carboxylic acid diphenylmethyl ester, [5S-(5α,6β,7α)]-3-(bromomethyl)-7-[[[2-[[(1,1-dimethylethoxy)carbonyl] amino]-4-thiazolyl]-(methoxyimino)acetyl]amino]-8-oxo- 5-thia-1-azabicyclo[4.2.0]oct-2-ene-2-carboxylic acid diphenylmethyl ester 5-oxide (CAS No. 134203-52-4), [5R-(5α,6α,7β)]-3-(bromomethyl)-7-(1,3-dihydro-1,3-dioxo-2H-isoindol-2-yl)-8-oxo-5-thia-1-azabicyclo[4.2.0]oct-2-ene-2-carboxylic acid methyl ester 5-oxide (CAS No. 124987-05-9), [5S-(5α,6β,7α)]-3-(bromomethyl)-8-oxo-7-[(phenoxyacetyl)amino]-5-thia-1-azabicyclo[4.2.0]oct-2-ene-2-carboxylic acid (4-nitrophenyl) methyl ester 5-oxide (CAS No. 121055-12-7), [6R-(6α,7β)]-3-(bromomethyl)-8-oxo-7-[(phenoxyacetyl)amino]-5-thia-1-azabicyclo[4.2.0]oct-2-ene-2-carboxylic acid methyl ester 5-oxide (CAS No. 80628-86-0), (6R-trans)-3-(bromomethyl)-8-oxo-7-[(phenylacetyl)amino]-5-thia-1-azabicyclo[4.2.0]oct-2-ene-2-carboxylic acid (4-methoxyphenyl)methyl ester (CAS No. 101156-41-6), (6R-trans)-3-(bromomethyl)-7-(1,3-dihydro-1,3-dioxo-2H-isoindol-2-yl)-8-oxo-5-thia-1-azabicyclo[4.2.0]oct-2-ene-2-carboxylic acid (4-nitrophenyl)methyl ester (CAS No. 78986-24-0), [6R-(6α,7β)]-7-(benzoylamino)-3-(bromomethyl)-8-oxo-5-thia-1-azabicyclo[4.2.0]oct-2-ene-2-carboxylic acid 1,1-dimethylethyl ester 5-oxide (CAS No. 71542-82-0), [5S-(5α,6β,7α)]-3-(bromomethyl)-7-[(bromophenylacetyl)amino]-8-oxo-5-thia-1-azabicyclo[4.2.0]oct-2-ene-2-carboxylic acid 1,1-dimethylethyl ester 5-oxide (CAS No. 121025-42-1), (6R-trans)-3-(bromomethyl)-8-oxo-7-[(phenylacetyl)amino]-5-thia-1-azabicyclo[4.2.0]oct-2-ene-2-carboxylic acid 1,1-dimethylethyl ester 5,5-dioxide (CAS No. 121025-24-9), [6R-[6α,7β(Z)]]-3-(bromomethyl)-7-[[[(fluoromethoxy)imino][2-[(triphenylmethyl)amino]-4-thiazolyl]acetyl]amino]-8-oxo-5-thia-1-azabicyclo[4.2.0]oct-2-ene-2-carboxylic acid diphenylmethyl ester (CAS No. 110190-86-8), (6R,7R)-7-(acetylamino)-3-(chloromethyl)-8-oxo-5-thia-1-azabicyclo[4.2.0]oct-2-ene-2-carboxylic acid diphenylmethyl ester (CAS No. 1003884-87-4), β-(chloromethyl)-7-[[2-[[(1,1-dimethylethoxy)carbonyl]amino]acetyl]amino]-5-thia-1-azabicyclo[4.2.0]oct-2-ene-2-carboxylic acid (CAS No. 935278-19-6), (6R,7R)-3-(chloromethyl)-8-oxo-7-[(2-phenylacetyl)amino]-5-thia-1-azabicyclo[4.2.0]oct-2-ene-2-carboxylic acid phenylmethyl ester 5,5-dioxide (CAS No. 929531-96-4), (6R,7R)-3-(chloromethyl)-8-oxo-7-[(2-phenylacetyl)amino]-5-thia-1-azabicyclo[4.2.0]oct-2-ene-2-carboxylic acid phenylmethyl ester 5-oxide (CAS No. 929531-93-1), (6R,7R)-7-(benzoylamino)-3-(chloromethyl)-8-oxo-5-thia-1-azabicyclo[4.2.0]oct-2-ene-2-carboxylic acid (4-methoxyphenyl)methyl ester (CAS No. 623136-61-8), (6R,7R)-3-(chloromethyl)-7-[[[(5-methyl-3-phenyl-4-isoxazolyl)-carbonyl]amino]-8-oxo-5-thia-1-azabicyclo[4.2.0]oct-2-ene-2-carboxylic acid diphenylmethyl ester (CAS No. 908287-20-7), 7-(benzoylamino)-3-(chloromethyl)-8-oxo-5-thia-1-azabicyclo[4.2.0]oct-2-ene-2-carboxylic acid (4-methoxy-phenyl)methyl ester (CAS No. 886219-89-2), (6R,7R)-3-(chloromethyl)-7-[(4-methylbenzoyl)amino]-8-oxo-5-thia-1-azabicyclo[4.2.0]oct-2-ene-2-carboxylic acid [4-[(di-phenylmethoxy)carbonyl]phenyl]methyl ester 5,5-dioxide (CAS No. 206856-18-0), (6R,7R)-3-(chloromethyl)-7-[(4-methylbenzoyl)amino]-8-oxo-5-thia-1-azabicyclo-[4.2.0]oct-2-ene-2-carboxylic acid (4-methylphenyl)methyl ester 5,5-dioxide (CAS No. 206855-92-7), (6R-trans)-7-(benzoylamino)-3-(chloromethyl)-8-oxo-5-thia-1-azabicyclo-[4.2.0]oct-2-ene-2-carboxylic acid methyl ester (CAS No. 151413-35-3), (6R-trans)-3-(chloromethyl)-8-oxo-7-[(phenylacetyl)amino]-5-thia-1-azabicyclo[4.2.0]oct-2-ene-2-carboxylic acid 4-methoxyphenyl ester (CAS No. 127431-38-3), (6R-trans)-7-(benzoylamino)-3-(iodomethyl)-8-oxo-5-thia-1-azabicyclo[4.2.0]oct-2-ene-2-carboxylic acid methyl ester (CAS No. 151413-36-4), (6R,7R)-7-(benzoylamino)-3-(iodomethyl)-8-oxo-5-thia-1-azabicyclo[4.2.0]oct-2-ene-2-carboxylic acid (4-methoxyphenyl)methyl ester (CAS No. 288091-94-1), (6R,7R)-7-(acetylamino)-3-(iodomethyl)-8-oxo-5-thia-1-azabicyclo[4.2.0]oct-2-ene-2-carboxylic acid diphenylmethyl ester (CAS No. 1003884-90-9), (6R-trans)-3-(iodomethyl)-8-oxo-7-[(phenoxyacetyl)amino]-5-thia-1-azabicyclo-[4.2.0]oct-2-ene-2-carboxylic acid methyl ester (CAS No. 140647-35-4), (6R-trans)-3-(iodomethyl)-8-oxo-7-[(phenylacetyl)amino]-5-thia-1-azabicyclo[4.2.0]oct-2-ene-2-carboxylic acid (4-nitrophenyl)methyl ester (CAS No. 133383-57-0), (6R,7R)-3-(iodomethyl)-8-oxo-7-[(2-phenylacetyl)amino]-5-thia-1-azabicyclo[4.2.0]oct-2-ene-2-carboxylic acid 2-propen-1-yl ester (CAS No. 140647-36-5), (6R,7S)-3-(iodomethyl)-8-oxo-7-[(phenoxyacetyl)amino]-1-azabicyclo[4.2.0]oct-2-ene-2-carboxylic acid 1,1-dimethylethyl ester (CAS No. 292621-64-8), (6R)-3-(bromomethyl)-8-oxo-5-thia-1-azabicyclo[4.2.0]oct-2-ene-2-carboxylic acid 1,1-dimethylethylester 5,5-dioxide (CAS No. 370 588-53-7), and (6R)-3-(iodomethyl)-8-oxo-5-thia-1-azabicyclo[4.2.0]oct-2-ene-2-carboxylic acid (4-nitrophenyl)methyl ester (CAS No. 359004-13-0).

Examples of a compound of general formula (XXX) include, but are not limited to, (2R,6R)-3-(bromomethyl)-8-oxo-5-thia-1-azabicyclo[4.2.0]oct-3-ene-2-carboxylic acid 1,1-dimethylethyl ester (CAS No. 370588-52-6), [6R-(6α,7β)]3-(bromomethyl)-8-oxo-7-[(2-thienylacetyl)amino]-5-thia-1-azabicyclo[4.2.0]oct-3-ene-2-carboxylic acid 1,1-dimethylethyl ester (CAS No. 66872-24-0), [6R-(6α,7β)]-3-(bromomethyl)-8-oxo-7-[(phenoxyacetyl)amino]-5-thia-1-azabicyclo[4.2.0]oct-3-ene-2-carboxylic acid diphenylmethyl ester (CAS No. 92411-31-9), [6R-[6α,7β(R*)]]-3-(bromomethyl)-7-[[[[(1,1-dimethylethoxy)carbonyl]amino]phenylacetyl]amino]-8-oxo-5-thia-1-azabicyclo[4.2.0]oct-3-ene-2-carboxylic acid diphenylmethylester (CAS No. 71492-25-6), (6R,7R)-3-[(acetyloxy)methyl]-8-oxo-7-[[2-[[7-(trifluoromethyl)-4-quinolinyl]-amino]acetyl]amino]-5-thia-1-azabicyclo[4.2.0]oct-3-ene-2-carboxylic acid diphenylmethyl ester (CAS No. 874918-78-2), (6R,7R)-3-(chloromethyl)-7-[[[[2,5-dichloro-4-[(1E)-3-[[2-(1,1-dimethylethoxy)-2-oxoethyl]amino]-3-oxo-1-propenyl]phenyl]thio]acetyl]amino]-8-oxo-5-thia-1-azabicyclo[4.2.0]oct-3-ene-2-carboxylic acid diphenylmethyl ester, (CAS No. 307002-29-5), (6R,7R)-3-[[[(3,4-dihydro-3-methyl-4-oxoimidazo[5,1-d]-1,2,3,5-tetrazin-8-yl)carbonyl]oxy]methyl]-8-oxo-7-[(2-thienylacetyl)amino]-5-thia-1-azabicyclo[4.2.0]oct-3-ene-2-carboxylic acid 2-propenyl ester (CAS No. 473988-52-2), (6R,7R)-3-[[[(3,4-dihydro-3-methyl-4-oxoimidazo[5,1-d]-1,2,3,5-tetrazin-8-yl)carbonyl]oxy]methyl]-8-oxo-7-[(phenylacetyl)amino]-5-thia-1-azabicyclo[4.2.0]oct-3-ene-2-carboxylic acid 2-propenyl ester (CAS No. 473988-51-1), (6R,7R)-3-[[[[5-chloro-2-(2,4-dichlorophenoxy)phenoxy]carbonyl]oxy]methyl]-8-oxo-7-[(2-thienylacetyl)amino]5-thia-1-azabicyclo[4.2.0]oct-3-ene-2-carboxylic acid (CAS No. 371915-01-4), [6R-(6α,7β)]-3-(chloromethyl)-8-oxo-7-[(phenylacetyl)amino]-5-thia-1-azabicyclo[4.2.0]oct-3-ene-2-carboxylic acid (4-methoxyphenyl)methyl ester 5-oxide (CAS No. 116133-79-0), (2R,6R,7E)-3-[(acetyloxy)methyl]-7-3-butenylidene)-8-oxo-5-thia-1-azabicyclo[4.2.0]oct-3-ene-2-carboxylic acid diphenylmethyl ester (CAS No. 222535-87-7), (2R,6R,7E)-3-[(acetyloxy)methyl]-8-oxo-7-(2-pyridinylmethylene)-5-thia-1-azabicyclo[4.2.0]oct-3-ene-2-carboxylic acid diphenylmethyl ester (CAS No. 222535-80-0), (2R,6R,7E)-3-[(acetyloxy)methyl]-8-oxo-7-(2-thienylmethylene)-5-thia-1-azabicyclo[4.2.0]oct-3-ene-2-carboxylic acid diphenylmethyl ester (CAS No. 222535-82-2), [2R-(2α,6α,7β)]-3-(bromomethyl)-7-[(methoxycarbonyl)amino]-8-oxo- 5-thia-1-azabicyclo[4.2.0]oct-3-ene-2-carboxylic acid 1,1-dimethylethyl ester (CAS No. 103957-61-5), [2R-(2α,6α,7β)]-3-(iodomethyl)-8-oxo-7-[(2-thienylacetyl)amino]-5-thia-1-azabicyclo[4.2.0]oct-3-ene-2-carboxylic acid diphenylmethyl ester (CAS No. 99364-09-7), [6R-(6α,7β)]-3-(bromomethyl)-8-oxo-7-[(phenylacetyl)amino]-5-thia-1-azabicyclo[4.2.0]oct-3-ene-2-carboxylic acid diphenylmethyl ester (CAS No. 94126-33-7), [2R-(2α,6α,7β)]-3-(bromomethyl)-7-(1,3-dihydro-1,3-dioxo-2H-isoindol-2-yl)-8-oxo-5-thia-1-azabicyclo[4.2.0]oct-3-ene-2-carboxylic acid (CAS No. 103841-51-6), (2R,6R,7R)-3-[(acetyloxy)methyl]-7-[[(1,1-dimethylethoxy)carbonyl]amino]-8-oxo-5-thia-1-azabicyclo-[4.2.0]oct-3-ene-2-carboxylic acid methyl ester (CAS No. 213265-43-1), 6R-(6α,7β)]-3-(bromomethyl)-8-oxo-7-[(phenoxyacetyl)amino]-5-thia-1-azabicyclo[4.2.0]oct-3-ene-2-carboxylic acid diphenylmethyl ester (CAS No. 92411-31-9), 6R-(6α,7β)]-3-(bromomethyl)-7-[(methoxycarbonyl)amino]-8-oxo-5-thia-1-azabicyclo[4.2.0]oct-3-ene-2-carboxylic acid 1,1-dimethylethyl ester (CAS No. 88109-60-8), [6R-(6α,7β)]-3-(chloromethyl)-4-methyl-8-oxo-7-[(2-thienylacetyl)amino]-5-thia-1-azabicyclo[4.2.0]oct-3-ene-2-carboxylic acid diphenylmethyl ester (CAS No. 87263-06-7), [6R-(6α,7β)]-3-(bromomethyl)-7-[[[[(1,1-dimethylethoxy)carbonyl]amino]phenylacetyl]amino]-8-oxo-5-thia-1-azabicyclo[4.2.0]oct-3-ene-2-carboxylic acid (4-nitrophenyl)methyl ester (CAS No. 64979-25-5), [6R-(6α,7β)]-3-(chloromethyl)-8-oxo-7-[(2-thienylacetyl)amino]-5-thia-1-azabicyclo[4.2.0]oct-3-ene-2-carboxylic acid diphenylmethyl ester (CAS No. 51999-37-2), [6R-(6α,7α)]-3-(bromomethyl)-7-methoxy-8-oxo-7-[(2-thienylacetyl)amino]-5-thia-1-azabicyclo[4.2.0]oct-3-ene-2-carboxylic acid 2,2,2-trichloroethyl ester (CAS No. 41095-79-8), [6R-(6α,7β)]-3-(bromomethyl)-8-oxo-7-[(2-thienylacetyl)amino]-5-thia-1-aza bicyclo[4.2.0]oct-3-ene-2-carboxylic acid phenylmethyl ester (CAS No 41095-53-8), [6R-(6α,7β)]-3-(bromomethyl)-8-oxo-7-[(phenoxyacetyl)amino]-5-thia-1-azabicyclo[4.2.0]oct-3-ene-2-carboxylic acid (4-nitrophenyl)methyl ester (CAS No 39876-53-4), 3-(bromomethyl)-4-(2-methyl-3-butenyl)-8-oxo-7-(2-phenoxyacetamido)-5-thia-1-azabicyclo[4.2.0]oct-3-ene-2-carboxylic acid (CAS No 28643-87-0) (6R,7R)-3-[[(amino-carbonyl)oxy]methyl]-7-[[(2Z)-2-(2-furanyl)-2-(methoxyimino)acetyl]amino]-8-oxo-5-thia-1-azabicyclo[4.2.0]oct-3-ene-2-carboxylic acid (CAS No 229499-08-5), [6R-(6α,7β)]-3-(bromomethyl)-8-oxo-7-[(phenoxyacetyl)amino]-5-thia-1-azabicyclo[4.2.0]oct-3-ene-2-carboxylic acid 1,1-dimethylethyl ester (CAS No 24670-49-3) and [6R-(6α,7β)]-3-(bromomethyl)-8-oxo-7-[(phenoxyacetyl)amino]-5-thia-1-azabicyclo[4.2.0]oct-3-ene-2-carboxylic acid (4-methoxyphenyl)methyl ester (CAS No 24144-89-6).

Examples of a compound of general formula (XXXI) include, but are not limited to, [2S-(2α,5α,6β)]-7-oxo-6-[(phenoxyacetyl)amino]-3-[2-(phenylmethoxy)ethylidene]-4-thia-1-azabicyclo[3.2.0]heptane-2-carboxylic acid (CAS No. 83089-77-4), [2S-(2α,5α,6β)]-3-(2-methoxyethylidene)-7-oxo-6-[(phenoxyacetyl)amino]-4-thia-1-azabicyclo[3.2.0]heptane-2-carboxylic acid (CAS No. 83089-76-3), [2R-(2α,5β,6α)]-3-(2-methoxyethylidene)-7-oxo-6-[(phenoxyacetyl)amino]-4-thia-1-azabicyclo[3.2.0]heptane-2-carboxylic acid phenylmethyl ester (CAS No. 83089-67-2, the 5α-compound has CAS No. 83089-66-1), and [2R-(2α,5β,6α)]-3-(2-methoxyethylidene)-7-oxo-6-[(phenoxyacetyl)amino]-4-thia-1-azabicyclo[3.2.0]heptane-2-carboxylic acid 1,1-dimethylethyl ester (CAS No. 83089-64-9, the [2S-(2α,5α,6β)]-compound has CAS No. 83089-63-8).

As a further example, a compound of general formula (XX) may be reacted with a compound of general formula (LIII) (see above). As a result a compound of general formula (VII) is formed. As another example, a compound of general formula (XX) may be reacted with a compound of general formula (XXI)

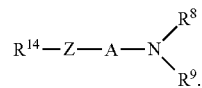

In this formula (XXI) $R^8$, $R^9$ and $R^{14}$ are as defined above. This reaction generally results in the formation of a compound of general formula (VIIa) (supra).

As yet two further examples, a compound of general formula (XXX) or of general formula (XXXI) may be provided:

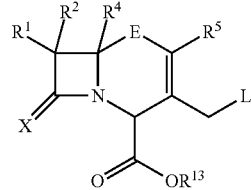

(XXX)

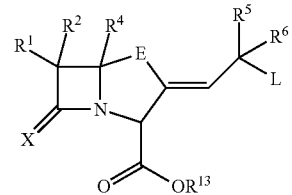

(XXXI)

L, $R^1$ to $R^5$ and $R^{13}$ in formulas (XXX) and (XXXI) as well as $R^6$ in formula (XXXI) are as defined above. In some embodiments $R^{13}$ is identical to $R^3$ (see above). In some embodiments $R^{13}$ is converted to $R^3$, for instance before, during or after the reaction with a compound of formula $R^{14}$—Z-A-Z—$R^{14}$. A reaction of a compound of general formula (XXX) and a compound of formula $R^{14}$—Z-A-Z—$R^{14}$ generally results in the formation of a compound of general formula II (supra). In some embodiments a compound of formula (XX), formula (XXX) or formula (XXXI) may be reacted with a compound of formula (LI), i.e., a compound of the structure $R^{18}$—Z-A-Z—$R^{18}$ (see above). Such a reaction generally results in the formation of a compound of general formula (XXII), (XXIII) and (XXIV), respectively (see above).

As a further example, a compound of formula (XX) may be reacted with one of the compounds of formulas (XXVI) and (XXVII):

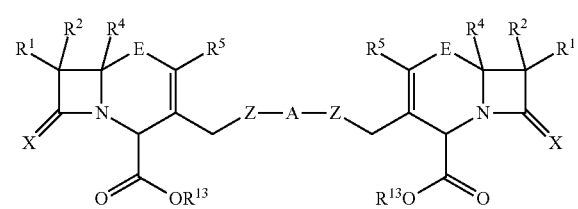

(XXVI)

(XXVII)

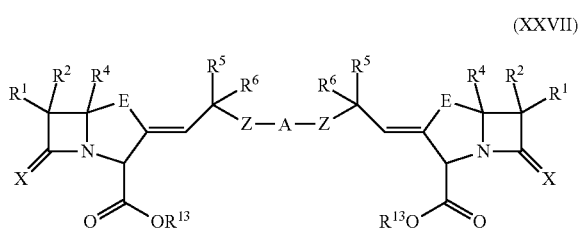

In these formulas E, X, Z, A, $R^1$ to $R^5$, $R^{13}$, and $R^6$ in formula (XXVII) are as defined above. Depending on the nature of $R^{13}$, the reaction of a compound of formula (XX) with a compound of formula (XXVI) generally results either in the formation of a compound of general formula (XXIII) or in the formation of general formula (LIX):

(LIX)

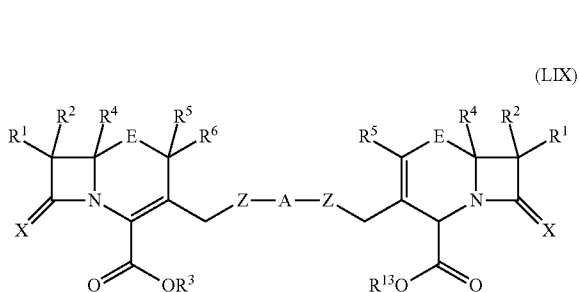

Likewise, the reaction of a compound of formula (XX) with a compound of formula (XXVII) generally results either in the formation of a compound of general formula (XXXIV) or in the formation of general formula (LX):

(LX)

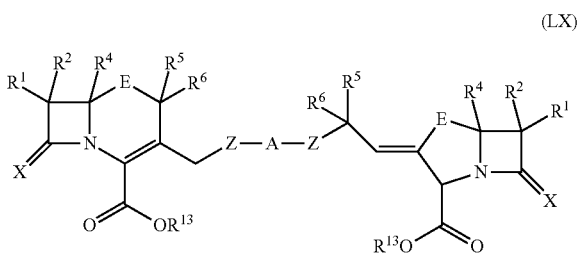

In this regard the compound of formula (XX) (see above) may for instance be represented by formula (LIV) and the compound of formula (XXX) may be represented by formula (LV):

(LIV)

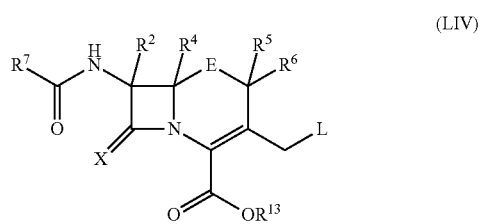

(LV)

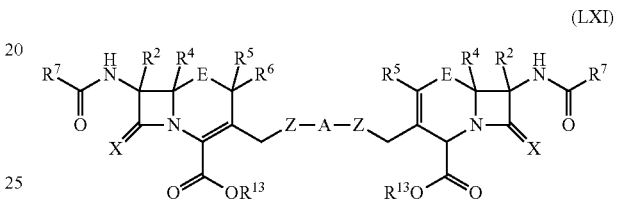

$R^7$ and $R^{13}$ in formulas (LIV) and (LV) are as defined above. A reaction of a compound of formula (LIV) with a compound of formula (XI) (see above) may for example result in the formation of a compound of formula (IXX) (see above) or of a corresponding compound of formula (LXI):

(LXI)

A compound of one of general formulas (I) to (XVIII), such as general formulas (I)-(IX), is also employed in a method according to the present invention. This method can be applied to any sample of any origin that might include β-lactamase activity. The sample may for instance, but not limited to, be derived from human or non-human animals, plants, bacteria, viruses, spores, fungi, or protozoa, or from organic or inorganic material of synthetic or biological origin. Accordingly, any of the following samples selected from, but not limited to, the group consisting of a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumor sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule, a production sample, a protein preparation sample, a lipid preparation sample, a carbohydrate preparation sample, a space sample, an extraterrestrial sample or any combination thereof may be processed in a method of the invention. Where desired, a respective sample may have been pre-processed to any degree. As an illustrative example, a tissue sample may have been digested, homogenized or centrifuged prior to being used with the device of the present invention. The sample may furthermore have been prepared in form of a fluid, such as a solution. Examples include, but are not limited to, a solution or a slurry of a nucleotide, a polynucleotide, a nucleic acid, a peptide, a polypeptide, an amino acid, a protein, a biochemical composition, an organic chemical composition, an inorganic chemical composition, a synthetic polymer, a metal, a lipid, a carbohydrate, a combinatory chemistry product, a drug candidate molecule, a drug molecule, a drug metabolite or of any combinations thereof. Further examples include, but are not limited to, a suspension of a metal, a suspension of metal alloy, and a solution of a metal ion or any combination thereof, as well as a suspension of a cell, a virus, a microorganism, a pathogen, a radioactive compound or of any combinations thereof. It is understood that a sample may furthermore include any combination of the aforementioned examples.

The sample is contacted with a nanoparticulate tag. The nanoparticulate tag may include a single particle of a maximal width from about 500 nm to about 1 nm or below. Such a particle may for instance be of a maximal width of about 200 nm to about 1 nm, about 200 nm to about 5 nm, including of about 200 nm to about 10 nm, of about 150 nm to about 10 nm, of about 150 nm to about 5 nm, of about 150 nm to about 1 nm, of about 100 nm to about 10 nm, 100 nm to about 5 nm or of about 100 nm to about 1 nm. While the use of particles of larger diameter, e.g., microparticles may also be tested if desired, the use of nanoparticles is recommended due to their large surface-to-volume ratio, their biocompatibility, high reactivity and their tailorable physicochemical properties. Examples of a suitable nanoparticle include, but are not limited to, a nanocrystal, a nanosphere, a nanoreef, a nanorod, a nanotube, a nanobox, a nanowire and a nanocup. The nanoparticulate tag may also include a plurality of such particles. It is understood that at least for the quantification of β-lactamase activity a plurality of nanoparticles is usually required. In a suitable β-lactamase activity range, where the method of the invention can be used to quantify such activity, generally an excess of nanoparticles in comparison to compounds or biological entities, such as cells, with β-lactamase activity is required. Nevertheless, plasmon resonance effects of a single nanoparticle can be detected using techniques used in the art. For example a nanoscale photodetector placed in the particle's near field has been shown to provide a detectable response (De Vlaminck, I., et al., *Nano Letters* (2007) 7, 3, 703-706).

The nanoparticulate tag may include any matter as long as a surface plasmon resonance can be detected. Typically nanoparticles of a nanoparticulate tag either include or consist of a metal or a metalloid, a combination of metals or a combination of one or more metals and/or one or more metalloids, or they include one or more carbon nanotubes or boron nitride nanotubes. A nanotube or nanotubes of a nanoparticulate tag may accordingly also be of a metal or a metalloid. In some embodiments, typically where the metal or the metalloid is included in the surface of the nanoparticulate tag, the metal or metalloid of a nanoparticulate tag is capable of forming a covalent bond or a coordinative bond with at least one of a thio group and a seleno group (see also below). In some embodiments, also typically where the metal or the metalloid is included in the surface of the nanoparticulate tag, the metal or metalloid is capable of forming non-covalent interactions with one or more of $R^{15}$ of the cleavage moiety Z-A-Z—$R^{15}$, $R^{16}$ of the cleavage moiety Z-A-Z—$R^{16}$, $R^{17}$ of the cleavage moiety Z-A-Z—$R^{17}$, $R^{18}$ of the cleavage moiety Z-A-Z—$R^{18}$, $R^8$ or $R^9$ of the cleavage moiety Z-G-N($R^8$)$R^9$ or the nitrogen atom of the cleavage moiety Z-G-N($R^8$)$R^9$ (see also above). Examples of non-covalent forces involved in establishing such a non-covalent interaction with the respective cleavage moiety are van-der-Waals interactions, Casimir interactions, electrostatic interactions, hydrophobic interactions, hydrogen bonding, solvation forces and Coulomb interactions. Two further examples are the formation of a coordinative bond and the formation of an ionic bond. As an illustration on such interactions, nitrogen atoms of nucleobases of nucleic acids are known to undergo interactions with metal nanoparticles, in particular silver nanoparticles that lead to the cross-linking and aggregation of the latter. The underlying interaction is thought to be particular strong in the case of presence of free valence electrons ("lone pair") at the nitrogen atom. The metal or metalloid of the nanoparticulate tag of the invention may for example undergo similar interactions with the nitrogen atom of the cleavage moiety Z-G-N($R^8$)$R^9$. The metal or metalloid may also be capable of forming a bond or interactions with other portions of a compound of the present invention.

In some embodiments matter included in the surface of the nanoparticulate tag that differs from the metal or metalloid is capable of forming a covalent bond, a coordinative bond, an ionic bond or other non-covalent interactions with a thio group and a seleno group. Such matter may also be capable of undergoing interactions with one of $R^{15}$, $R^{16}$, $R^{17}$, $R^{18}$, the nitrogen atom of the cleavage moiety Z-G-N($R^8$)$R^9$, or with other portions of a compound of the present invention.

The nanoparticulate tag may include nanoparticles with a metal core, surrounded by a shell of any desired matter such as carbon, a polymer. In some embodiments the nanoparticulate tag may include a shell, including a surface that consists of a metal or a combination of metals. In such embodiments the nanoparticulate tag may include nanoparticles with a core of any desired matter and a metal shell. The nanoparticulate tag may include a nanoparticle with a portion, such as a core or a shell that is of or includes a metal, while the residual nanoparticle is of other matter such as a metalloid, ceramic or a polymer. In some embodiments the nanoparticle(s) have a shell of a metal that is covered with an outer shell of any desired matter such as carbon, a polymer.

In some embodiments the nanoparticulate tag exhibits a surface plasmon resonance at visible wavelengths, possibly including at near-infrared frequencies. Such a nanoparticulate tag may be based on or more nanoparticles that include or consist of a noble metal such as gold or silver, i.e. an element of group 11 of the periodic table of elements (according to the new IUPAC system, group IB according to the old IUPAC system and the CAS system), or an element of group 10 of the periodic table of elements (according to the new IUPAC system, in group VIIIA according to the old IUPAC system and group VIII of the CAS system) such as palladium or platinum. Respective nanoparticles show strong plasmon resonance extinction bands in the visible spectrum, and therefore deep colors reminiscent of molecular dyes. These extinction bands occur if the incident photo frequency is resonant with the collective oscillation of the free (conduction) electrons, also known as the localized surface plasmon resonance (LSPR). LSPR excitation results in wavelength selective absorption with extremely large molar extinction coefficients, efficient Rayleigh scattering and enhanced local electromagnetic fields near the surface of the nanoparticle. A variety of reviews are available providing an introduction into surface plasmon resonance, which is a method well established in the art, as well as its application to sensors (see e.g. Willets, K. A., & Van Duyne, R. P., *Annu. Rev. Phys. Chem.* (2007) 58, 267-297; Homola, J. et al., *Anal Bioanal Chem* (2003) 377, 528-539; Schuck, P., *Annu. Rev. Biophys. Biomol. Struct.* (1997) 26, 541-566; or Hafner, J., *Laser Focus World* (2006) April, 99-101).

It is well established in the art that the peak extinction wavelength of the LSPR spectrum correlates to the size, shape, composition and interparticle spacing of the nanoparticles. It is further affected by its dielectric properties and those of the local environment. On an individual basis plasmon resonance characteristics and emission properties of nanoparticles correlate in situ (Steiner, M., et al., *J. Phys. Chem. C* (2008) 112, 3103-3108). In embodiments where one or more nanoparticles with a shell that includes or consists of a metal or a combination of metals is used, the thickness and the geometry of the shell can be used to tune the Plasmon resonance frequency (see e.g. Norton, S. J., & Vo-Dinh, T., *IEEE Transactions on Nanotechnology* (2007) 6, 6, 627-638). Nanoparticles of a variety of shapes, such as spheres, prisms, cubes, bipyramids or rods can be formed using standard methods known in the art. Furthermore, the shape of nanoparticles can be altered by means of a laser (see, e.g., Stalmashonak, A., et al., *Optics Letters* (2007) 32, 21, 3215-3127). A certain shape of nanoparticles used in the method of the invention may be selected according to the desired technique of detecting the presence of a cleavage moiety on its surface. In this regard elongated nanostructures have been found to show a large local field enhancement, making them particularly suitable for Raman and fluorescence spectroscopies (Liu, M., & Guyot-Sionnest, P., *Physical Review B* (2007) 76, 235428). In situ tuning of single nanoparticles by optically induced growth has also been reported, which allows providing a resonance blue shift for ellipsoidal particles and a resonance red shift for spheres (Härtling, T., et al., *Journal of Physical Chemistry C* (2008) 112, 13, 4920-4924).

As two illustrative examples, gold nanoparticles in a neutral aqueous solution have a deep red color while silver nanoparticles have a yellow color. The formation of gold nanorods, as well as their use in a surface plasmon resonance assay, has for instance been described by Mayer et al. (*ACS Nano* (2008) 2, 4, 687-692, doi: 10.1021/nn7003734) and Sau et al. (*J. Am. Chem. Soc.* (2004) 126, 28, 8648-8649). As a comparison, manganese nanoparticles covered by silica have been reported to have a plasmon resonance of about 300 nm, which is in the near ultraviolet (Yeshchenko, O. A. et al., *Applied Surface Science* (2008) 254, 2736-2742). Nanoparticles with a silica core and a gold film as a shell, which are suitable for the method of the invention, have been characterized by Hiep et al. (*Analytical Chemistry* (2008) 80, 6, 1859-1864, doi: 10.1021/ac800087u). With increasing thickness of the gold film a red shift and a signal increase was observed. The core size was also found to affect signal intensity and color. Highly monodisperse gold nanoparticles with urchin-like shape can be formed from $HAuCl_4$ and $K_2CO_3$ using gelatin and silver nanoparticles as seed (Lu, L., et al., *Langmuir* (2008) 24, 1058-1063). The surface plasmon resonance bands of these nanoparticles are tunable depending on their geometric shape.

Surface plasmon resonance is known to be capable of detecting sub-monolayer quantities of matter. It does furthermore not depend on additional labels that generate signals, e.g., fluorescent tags. In embodiments where the nanoparticle(s) have a metal covered with an outer shell of additional matter, such additional matter may facilitate the detection of plasmon resonance, depending on the selected technique. The additional matter may for example act as a waveguiding layer for optical evanescent-wave-based sensing devices. A metal-oxide layer including niobium oxide or silicon oxide, covered with e.g., a polycationic polymer, may for instance facilitate the use of surface plasmon spectroscopy, optical waveguide lightmode spectroscopy or plasmon-waveguide resonance spectroscopy.

Nanofilaments suitable for the present method of the invention typically have a diameter of about 1-500 nm, such as about 1-200 nm, about 3-200 nm, about 5-150 nm or about 10-100 nm. A respective nanofilament may be of any length and diameter. In some embodiments these nanofilaments may be carbon nanofilaments or boron nitride nanofilaments. Illustrative examples of a carbon nanofilament are a carbon nanotube, a carbon nanohorn and a carbon nanowire. Nanotubes are hollow while nanowires are solid. Carbon nanotubes can be either metallic or semiconducting, while boron nitride nanotubes are semiconducting (see e.g., Ishigami, M., et al., *Scanning Tunneling Microscopy/Spectroscopy and Related Techniques: 12th Internat. Conference*, CP696 [2003], edited by P. M. Koenraad and M. Kemerink, 94-99). A boron nitride nanotube is a cylinder rolled from a hexagonal sheet of boron nitride. Carbon nanotubes are pre-formed according to any desired method (see e.g., Rao, C. N. R., et al., *ChemPhysChem* [2001] 2, 2, 78-105). Similar to a boron nitride nanotube, a carbon nanotube is a cylinder of rolled up graphitic sheets. Both single- and multi-walled carbon nanotubes are known and can equally be used in the method of the present invention. The carbon nanotubes may be of any desired length, such as in the range from about 10 nm to about 500 μm, such as about 20 nm to about 100 μm or about 10 nm to about 10 μm. The conductivity of the carbon nanotubes used may be freely selected according to any specific requirements of particular embodiments. Depending on the arrangement of the carbon hexagon rings along the surface of the nanotube carbon nanotubes can be metallic or semiconducting. Any such carbon nanotubes may be used in a method according to the present invention as long as they have a suitable plasmon resonance.

Gold, silver, copper and nickel nanoparticles as well as carbon nanotubes that are suitable for the method of the invention are commercially available, e.g., from Nanocs Inc. (New York, N.Y.), Pchem Associates Inc. (Pennsylvania), NanoDynamics Inc. (Buffalo, N.Y.), Nanostructured & Amorphous Materials Inc. (Houston, Tex.), Nanoprobes Inc. (Yaphank, N.Y.), Nanoparts Inc. (Kailua, Hi.), Ted Pella Inc. (Redding, Calif.) or ItN Nanovation AG (Saarbrücken, Germany). Nanoparticles of various other metals are known in the art and generally suitable for use in the method of the present invention. For example, cobalt and nickel nanoparticles have been formed by laser ablation in organic solution from solid cobalt and nickel plates (Zhang, J., Lan, C. Q., *Materials Letters* (2008) 62, 1521-1524). As a further example, silver nanoparticles may be formed in the form of a silver sol by reducing silver nitrate with a reducing agent, for example sodium borohydride. Silver and copper nanoparticles can also be formed from a corresponding metal salt using sodium formaldehyde sulfoxylate and a surfactant such as myristic acid or oleic acid. Copper nanoparticles may further for example be formed by electrolytic methods, photochemically or sonochemically. Ascorbic acid has also been used as a reducing agent in the formation of copper nanoparticles. A variety of techniques is available for the formation of nanoparticles, including for instance lithographic techniques, such as nanosphere lithography or e-beam lithography. Vapor deposition, electrochemical reduction, radiolytic reduction, sputtering and thermal decomposition are further examples of techniques that can be employed to form metal nanoparticles. Where sputtering is for instance magnetron sputtering gas phase aggregation cluster source, a filter such as a time of flight mass filter can be used to select nanoparticles of a desired width, such as a desired diameter. Nanoparticles with a polymer core can for example be formed by first forming polymer spheres, dispersing them in a colloidal solution of a metal and adding a reducing agent.

As noted above, in the method of the invention the sample is further contacted with a compound as defined above, i.e. of one of general formulas (I) to (IX). The sample may be contacted with the nanoparticulate tag before, after or concomitantly with being contacted with a compound of general formula (I). Accordingly, in some embodiments the sample is for instance first contacted with the nanoparticulate tag, whereas in other embodiments it is contacted with the nanoparticulate tag and with a compound of one of general formulas (I) to (IX) at the same time.

The sample (supra) is generally suspected to include β-lactamase activity. Accordingly, the method of the invention is aimed at detecting any such activity, in particular any β-lactamase present. As used herein, the term 'detection', 'detecting' or 'detect' refers broadly to measurements which provide an indication of the presence or absence, either qualitatively or quantitatively, of an analyte. Accordingly, the term encompasses quantitative measurements of the concentration of an analyte nucleic acid molecule in a sample, as well as qualitative measurements in which for instance different types of analyte molecules in a given sample are identified, or, as a further example, the behavior of a particular analyte molecule in a given environment is observed. The term 'quantification' refers solely to quantitative measurements of the amount, e.g., the concentration, of an analyte molecule.

β-Lactamases are the most common reason of bacterial resistance to β-lactam antimicrobial agents. These enzymes hydrolytically cleave β-lactam antibiotics such as penicillins and cephalosporins. This type of resistance can often be transferred between bacteria by plasmids that are capable of rapidly spreading the resistance, not only to other members of the same strain of bacteria, but even to other species of bacteria. The beta lactamase activity in the sample is allowed to cleave at least one beta-lactam ring of the compound of one of general formulas (I) to (IX), and thus the respective beta-lactam moiety. In this regard, the term "cleave" is used in its common meaning in the art, referring to the disappearance of a previously present covalent bond. Where this bond was part of a ring structure, its removal leads to the cleavage of the ring, typically resulting in a linear structure. Where this bond was part of a linear structure, its cleavage typically leads to the disintegration of the molecule, resulting in the formation of two or more, typically shorter or smaller, products.

A further example of lactamase activity is a bacterial enzyme that is capable of cleaving one or more β-lactam substrates such as D-aminopeptidase (EC 3.4.11.19) from *Ochrobactrum anthropi*, which has been shown to have β-lactamase activity toward ampicillin and penicillin G (Asano, Y., et al., *J. Biol. Chem.* (1996) 271, 47, 30256-30262).

Figure 4A:
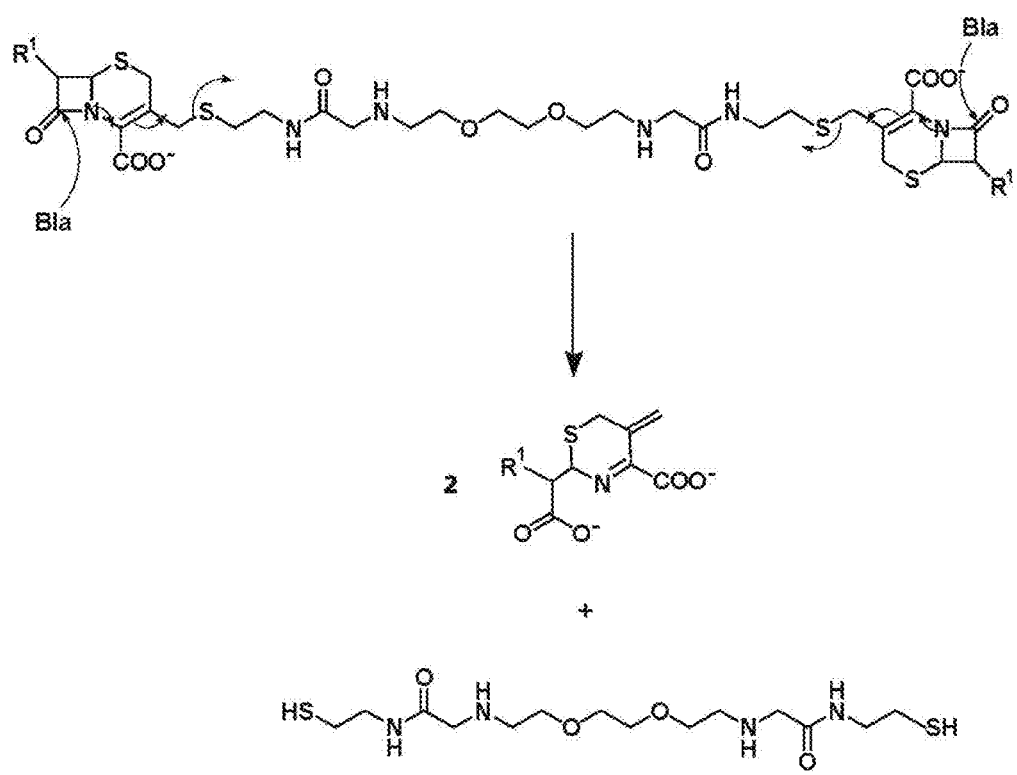
FIG. 4A illustrates the reaction mechanism of the cleavage of an embodiment of a compound of general formula (I), also represented by general formula (X), by lactamase activity, e.g., a lactamase enzyme.

In typical embodiments the β-lactamase activity will cleave both beta-lactam moieties in the compound used. As an illustration, FIG. 4A depicts the reaction mechanism of the cleavage of both β-lactam moieties of a corresponding embodiment of a compound of formula (I), e.g. formula (XXXII). Without being bound by theory, other compounds of the invention are assumed to undergo a cleavage reaction with a comparable mechanism, as briefly illustrated in FIG. 4B and FIG. 4C. β-Lactamase (Bla) activity, e.g., a protein having such catalytic activity, cleaves the β-lactam moiety. The term "β-lactam moiety" as used herein refers to a structural part of a compound that includes a β-lactam ring structure. Examples of compounds that include the beta-lactam moiety include clavulanic acid, penicillanic acid, and cephalosporanic acid. The β-lactam structure is:

The cleavage moiety Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$ is thereby released (cf. FIG. 4). In typical embodiments a thiol compound or a selenol compound, respectively, is formed. $R^8$, $R^9$, $R^{15}$, $R^{16}$ and/or $R^{17}$, where present in the released cleavage moiety, may be subject to a further reaction that may lead to its conversion to another group, such as hydrolysis.

In embodiments where the compound is of one of general formulas (XXXIII), (XXXIV) and (XXXVI) the released cleavage moiety is typically of the formula Z-A-Z. In embodiments where the compound is of the general formula (I) the released cleavage moiety is typically of the formula Z-A-Z—$R^{15}$ if $R^{15}$ does not further undergo a conversion. In embodiments where the compound is of the general formula (II) the released cleavage moiety is typically of the formula Z-A-Z—$R^{16}$ if $R^{16}$ does not further undergo a conversion. In embodiments where the compound is of the general formula (III) the released cleavage moiety is typically of the formula Z-A-Z—$R^{17}$ if $R^{17}$ does not further undergo a conversion. In embodiments where the compound is of one of the general formulas (XXII)-(XXIV) the released cleavage moiety is typically of the formula Z-A-Z—$R^{18}$ if $R^{18}$ does not further undergo a conversion. If $R^{18}$ is a bicyclic moiety such a moiety corresponding to a 4-thia-1-azabicyclo[3.2.0]heptane-2-carboxylic acid derivative, a 5-thia-1-azabicyclo[4.2.0]oct-2-ene-2-carboxylic acid derivative or a 5-thia-1-azabicyclo[4.2.0]oct-3-ene-2-carboxylic acid derivative, this bicyclic moiety may—depending on the specificity of the b-lactamase present (see below)—also be subject to cleavage of the latter activity. In such a case the released cleavage moiety is typically of the formula Z-A-Z. In embodiments where the compound is of one of the general formulas (VII)-(IX) the released cleavage moiety is typically of the formula Z-G-N—($R^8$)$R^9$ unless one or both of $R^8$ and $R^9$ undergoe(s) a further conversion such as hydrolysis.

The moiety Z-A-Z, Z-A-Z—$R^{15}$, Z-A-Z—$R^{16}$, Z-A-Z—$R^{17}$, Z-A-Z—$R^{18}$ or respectively Z-G-N($R^8$)$R^9$, typically via the corresponding thiol or selenol compound formed, is allowed to be immobilized on the surface of the nanoparticulate tag. The immobilization occurs in the form of covalent bond between the nanoparticulate tag, generally an individual nanoparticle, and an S or Se atom. This S or Se atom is one of the atoms Z in formulas Z-A-Z, Z-A-Z—$R^{15}$, Z-A-Z—$R^{16}$, Z-A-Z—$R^{17}$ or Z-A-Z—$R^{18}$, and the atom Z in formula Z-A-N($R^8$)$R^9$. In embodiments where the cleavage moiety has been formed by the cleavage of a compound of one of formulas (I) to (VI) the cleavage moiety is of the formula Z-A-Z, Z-A-Z—$R^{15}$, Z-A-Z—$R^{16}$, Z-A-Z—$R^{17}$ or Z-A-Z—$R^{18}$ or a corresponding compound obtained by a subsequent reaction, e.g., hydrolysis, of $R^{15}$, $R^{16}$, $R^{17}$ or $R^{18}$, respectively, thereof, if applicable. In these embodiments at least one of the S or Se atoms (symbolized by Z) is allowed to be immobilized on the surface of the nanoparticulate tag. In embodiments where the cleavage moiety has been formed by the cleavage of a compound of one of formulas (VII) to (IX) the cleavage moiety is of the formula Z-A-N($R^8$)$R^9$, or a corresponding compound obtained by a subsequent reaction, e.g. hydrolysis, of $R^8$ or $R^9$ thereof. In such embodiments the nitrogen atom may also be allowed to be immobilized on the surface of the nanoparticulate tag in addition to the Z atom. This may occur in the form of a covalent bond, a coordinative bond or non-covalent interactions (e.g., electrostatic interactions such as dipole-dipole interactions, or van-der-Waals interactions). Such immobilization via the N atom may in particular occur in embodiments where one or both of $R^8$ and $R^9$ are H.

As should be apparent from the above, there are two reactive sites in the linking moiety. The first reactive site is defined by a first atom Z and the second reactive site is defined by the second atom Z or the nitrogen atom (supra). Accordingly, these two reactive sites are also present in the cleavage moiety, which is being released from a compound of the invention and includes the linking moiety thereof. Thus the first reactive site of the released cleavage moiety Z-A-N($R^8$)$R^9$ from the cleaved compound of one of general formulas (VII)-(IX) is the atom Z present. The first reactive site of the released cleavage moiety Z-A-Z from the cleaved compound of one of general formulas (I)-(VI) is the first atom Z. The same applies to the first atom Z of the cleavage moiety Z-A-Z—$R^{15}$ released from a compound of general formula (I), the cleavage moiety Z-A-Z—$R^{16}$ released from a compound of general formula (II), the cleavage moiety Z-A-Z—$R^{17}$ released from a compound of general formula (I) or the cleavage moiety Z-A-Z—$R^{18}$ released from a compound of general formulas (XXII) to (XXIV)—or any corresponding compound obtained by a subsequent reaction of $R^{15}$, $R^{16}$, $R^{17}$ or $R^{18}$, respectively, The second reactive site of the released cleavage moiety Z-A-N($R^8$)$R^9$ from the cleaved compound of one of general formulas (VII)-(IX) is defined by the atom N. The second reactive site of the released cleavage moiety Z-A-Z from the cleaved compound of one of general formulas (I)-(VI) is the second atom Z. As a further example, the second reactive site of the released cleavage moiety Z-A-Z—$R^{15}$ from the cleaved compound of general formula (I) is also the second atom Z. With reference to FIG. 4 it is noted that in each molecule of a compound with two bicyclic moieties (IV)-(VI) (supra), such as a compound of one of formulas (XXVI) (XXXIII), (XXXIV) or (XXXVI), two cleavage reactions can occur. Each cleavage reaction leads to the breakage of a covalent bond between the atom Z and the residual portion of the molecule that includes a bicyclic moiety. This residual portion thus differs from the linker (symbolized by A). Upon each cleavage reaction a molecular reaction of the atom Z will occur. This may lead to the formation of a group ZH or to the formation of a covalent bond between a surface of the nanoparticulate tag and the atom Z. In contrast thereto, in each molecule of a compound of formulas (I)-(III) that does not include a bicyclic moiety in $R^{15}$, $R^{16}$, $R^{17}$ or $R^{18}$, only one cleavage reaction can generally occur upon the action of a β-lactamase activity. Likewise, only one cleavage reaction per molecule can generally occur in compounds of general formulas (VII) to (IX). In the latter compounds no cleavage will typically occur between the nitrogen atom and the moieties $R^8$ and $R^9$. Nevertheless the corresponding amino group may be able to associate to or form a bond with the nanoparticulate tag, in particular where one of $R^8$ and $R^9$ is H.

In the context of the method of detecting β-lactamase activity the compounds of general formulas (I) to (III), (VII)-(IXX), (XXV)-(XXVII), (IXXX), (XXXIII), (XXXIV), (XXXVI) and (XXXVII) and related compounds are also called the substrate for a β-lactamase enzyme or simply the "substrate". In some embodiments no immobilization of the substrate or of a molecule derived therefrom occurs in the absence of β-lactamase activity. Such embodiments are depicted in FIG. 1A and FIG. 1C. In embodiments where the moiety $R^8$ includes a reactive group, capable of immobilization on the nanoparticulate tag, for example a seleno group, a thio group, an azido group, a halogen group, or an amino group, immobilization of the substrate may however occur. In some embodiments the amino group of the cleavage moiety Z-A-N($R^8$)$R^9$ of the compound of one formulas (VII) to (IX) is a primary or a secondary amino group, i.e. one or both of $R^8$ and $R^9$ are H. In such embodiments immobilization of the substrate will generally occur in the absence of β-lactamase activity. Such an embodiment is depicted in FIG. 1E.

Based on the presence of the cleavage moiety Z-A-Z, Z-A-Z—$R^{15}$, Z-A-Z—$R^{16}$, Z-A-Z—$R^{17}$, Z-A-Z—$R^{18}$ or respectively Z-G-N($R^8$)$R^9$, immobilized onto the surface of the nanoparticulate tag, the presence of beta-lactamase activity is determined in the present method of the invention. In some embodiments the surface, which may be coated with further matter (supra), of the nanoparticulate tag is capable of creating a plasmon resonance effect. This plasmon resonance effect occurs upon exposure to electromagnetic radiation. Surface plasmon resonance is an electron charge density wave phenomenon occurring at a metal surface. Plasmon resonance is sensitive to the refractive index of the medium in contact with the metal surface. Accordingly, the ambience of the nanoparticulate tag may adapted, e.g., by exchanging the or adding a solvent or additives, when optimizing a particular embodiment of the invention for a specific purpose. Immobilization of matter on the surface of the nanoparticulate tag, such as a moiety Z-A-Z, a moiety Z-A-Z—$R^{15}$, Z-A-Z—$R^{16}$, Z-A-Z—$R^{18}$ or Z-G-N($R^8$)$R^9$, typically alters this plasmon resonance effect. In some embodiments determining the presence of beta-lactamase activity is based on the alteration of the plasmon resonance effect of the surface of the nanoparticulate tag by the immobilization of the cleavage moiety Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$ thereon.

As noted above, in some embodiments no immobilization of the substrate occurs in the absence of β-lactamase activity. In such embodiments the method is based on the immobilization of the cleavage moiety Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$ on the nanoparticulate tag. In other embodiments the substrate already immobilizes on the nanoparticulate tag regardless of the presence or absence of β-lactamase activity. As an example already used above as an illustration, in embodiments where the substrate is of one of formulas (IV) to (IX), the moiety $R^8$ may include a reactive group, capable of immobilization on the nanoparticulate tag, for example a seleno group, a thio group, an azido group, a halogen group, or an amino group, via this group the substrate may be immobilized on the nanoparticulate tag. In such embodiments the action of β-lactamase, cleaving a β-lactam ring of the substrate, leads to a detectable change on the surface of the nanoparticulate tag. The substrate may for example be immobilized on a first nanoparticle. The formation of one or more reactive sites (see above) due to cleavage reaction caused by the lactamase activity may for example lead to the reaction of a newly formed reactive site with the surface of a second nanoparticle. Thereby aggregation of nanoparticles may occur. An example of such an embodiment is depicted in FIG. 1E.

In some embodiments of the method of the invention no aggregation of nanoparticles occurs, whether in the presence or in the absence of β-lactamase activity. Such embodiments are exemplified by the use of a substrate of e.g. one of formulas (I) to (III), which neither include an additional β-lactam ring, nor a functional group capable of immobilization on the nanoparticulate tag. Action of β-lactamase activity, e.g. a β-lactamase enzyme, leads to the release of a cleavage moiety Z-A-Z—$R^{15}$, Z-A-Z—$R^{16}$, Z-A-Z—$R^{17}$, Z-A-Z—$R^{18}$ or Z-G-N($R^8$)$R^9$ with two reactive sites (see also above). The second reactive site defined by either the atom Z to which $R^{15}$, $R^{16}$, $R^{17}$ or $R^{18}$ are bonded, or by the nitrogen atom, may be of a low reactivity that does not allow for an immobilization on the nanoparticulate tag. An example of such an embodiment is illustrated in FIG. 1C, where upon cleavage of a substrate of formula (IV) a cleavage moiety Z-A-Z—$R^8$ is released.

In some embodiments both immobilization of the substrate and aggregation of nanoparticles occurs in the presence of β-lactamase activity, while no immobilization of the substrate occurs in the absence of β-lactamase activity. Such embodiments are exemplified by the action of a β-lactamase that—upon cleavage of a substrate of e.g., formula (XXV), (XXVI), (XXVII), or (XXXII)-(XXXVII)—results in the release of a cleavage moiety Z-A-Z with two reactive sites (see also above) that are of the same, similar or at least essentially comparable reactivity. An example of such an embodiment is illustrated in FIG. 1A, where upon cleavage of a substrate of formula (XXV) a cleavage moiety Z-A-Z is released. In any of the embodiments illustrated in this and the preceding paragraphs the action of β-lactamase activity alters the plasmon resonance effect of the nanoparticulate tag.

Various methods are known in the art to detect plasmon resonance and alterations thereof. The alteration of the plasmon resonance effect may be detected based on a characteristic selected from a color, fluorescence, Raman scattering, a refractive index, a dielectric constant, a magnetic permeability, an electrical property and second harmonic generation. Raman scattering is for instance based on the polarization of the dipoles excited in a particle when a laser beam interacts with collective vibrations of the particle. Raman scattering occurs if vibrations change polarizability. Subtle spectra alterations can be used to assess nanoscale structural changes. Additional effects such as resonance Raman scattering (typically with the energy of the laser excitation set in the UV-nIR range) may be included. Surface-enhanced Raman spectroscopy may be used, which is based on an amplification of a Raman signal by several orders of magnitude for molecules adsorbed on metal particles and metal nanowires. Amplification occurs due to interaction between the electromagnetic field of the laser excitation and the surface plasmon of the metal. Second harmonic generation (SHG) and sum frequency (SFG) spectroscopy as further examples are explained to be based on the intrinsically noncentrosymmetric structure of interfaces of nanoparticles. This technique thus probes the surface region of a nanoparticle. A second harmonic generation signal includes both electric dipole and electric quadrupole contributions, which have been attributed to plasmon resonances of the nanoparticle. As the interface of a nanoparticle is altered by the immobilization of the cleavage moiety Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$, respectively (see above), signals are altered and can thus be detected. Second harmonic generation has been found to be particularly suitable for embodiments where aggregation of nanoparticles occurs. This may be due to a change in the surface electronic structure, and has also been explained in terms of the formation of a noncentrosymmetric entity during the change in the surface profile from a centrosymmetric nanosphere to an aggregate. The technique may also be applied to particles with a metal core and e.g. a polymer or a metalloid shell or e.g. metalloid nanoparticles, such as silica nanoparticles, with a metal shell.

As already indicated above, in some embodiments the nanoparticulate tag exhibits a surface plasmon resonance at visible wavelengths. Hence, the nanoparticulate tag shows color due to surface plasmon resonance. An alteration of the plasmon resonance effect due to the immobilization of the cleavage moiety on the surface of the nanoparticulate tag alters this color.

As noted above, in some embodiments the nanoparticulate tag consists of a plurality of nanoparticles. In such embodiments the plurality of particles may include a first and a second nanoparticle. The cleavage moiety Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$ of a molecule of the compound of general formulas (I)-(III), (VII)-(IXX), (XXV)-(XXVII), (IXXX), (XXXIII), (XXXIV), (XXXVI) and (XXXVII) includes a first and a second atom Z, i.e., a first and a second sulfur or selenium atom. The action of beta-lactamase activity in the sample may lead to cleavage of both the beta-lactam moieties (supra) of a compound of general formulas (XXV)-(XXVI), (XXXIII), (XXXIV) or (XXXVI) to (XII). As a result the first thio or selenium atom of the respective released cleavage moiety Z-A-Z, Z-A-Z—$R^{15}$, Z-A-Z—$R^{16}$, Z-A-Z—$R^{17}$, Z-A-Z—$R^{18}$ may be immobilized on the surface of the first particle. The second thio or selenium atom of the released cleavage moiety may be immobilized on the surface of the second particle. Thus the first and the second particle are coupled (see also above). In such embodiments the presence of beta-lactamase activity may be determined based on the aggregation of nanoparticles. The detection based on aggregation and based on alteration of the surface plasmon resonance effect may be applied in the alternative, but also in combination. Accordingly, the alteration of the surface plasmon resonance effect may also be determined in embodiments where aggregation of the nanoparticles occurs. Such combination may be desired in some embodiments as the alteration of the plasmon resonance effect may be enhanced by aggregation of nanoparticles.

In typical embodiments, the result obtained in detecting the presence of beta lactamase activity is compared to that of a reference measurement (or control measurement). In a respective reference measurement a control compound resembling the compound of one of general formulas (I)-(III), (VII)-(IXX), (XXV)-(XXVII), (IXXX), (XXXIII), (XXXIV), (XXXVI) and (XXXVII) may for instance be used instead of the corresponding compound, i.e. the compound of general formula (I)-(III), (VII)-(IXX), (XXV)-(XXVII), (IXXX), (XXXIII), (XXXIV), (XXXVI) and (XXXVII). The control compound may however not be cleavable by β-lactamase activity, so that no linker Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$ can be released. In embodiments where the sample and the nanoparticulate tag are contacted before the compound of one of general formulas (I)-(III), (VII)-(IXX), (XXV)-(XXVII), (IXXX), (XXXIII), (XXXIV), (XXXVI) and (XXXVII) is added, a further example of a reference measurement is determining the respective characteristic or property, such as the color or the plasmon resonance before adding this compound. Determining the respective characteristic or property immediately upon, or even simultaneously with, contacting the sample with the respective compound and the nanoparticulate tag may in some embodiments also serve as a suitable reference measurement. Yet a further example of a reference measurement (that may also be performed on the same sample during analysis) is adding an inhibitor of β-lactamase activity to the sample. If the two measurements, i.e., "sample" and "control" measurement, differ in such a way that the difference between the values determined is greater than a pre-defined threshold value, the sample contained β-lactamase activity.

In typical embodiments a threshold value in relation to a reference measurement is defined. This threshold value may be a fixed value of a respective characteristic or property, on which determining the presence of β-lactamase activity is based. The presence or absence of β-lactamase activity is then determined by means of comparison of the value detected, typically in relation to the reference measurement, with the threshold value. If the obtained value exceeds the threshold value, then it is inferred that beta-lactamase activity is present in the sample, and if appropriate in what concentration. In the case that a detected value is below the threshold value it is inferred that no β-lactamase activity is present. In the same way the rate of change of a property/parameter more than a predetermined threshold value can be used to indicate the presence of β-lactamase activity in a sample. A respective threshold value may for instance be determined in a calibration experiment, e.g. using different amounts of β-lactamase activity in a medium that is known or expected to correspond to the sample.

The method of the invention can be carried out in any solvent, in which β-lactamase activity can occur, e.g., in which a β-lactamase enzyme is capable of hydrolyzing a β-lactam ring. Further, the respective solvent needs to allow the selected technique to be carried out that allows determining the presence of the cleavage moiety Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$ immobilized onto the surface of the nanoparticulate tag. The solvent may for instance need to allow the detection of changes of the surface plasmon resonance effect. In typical embodiments an aqueous solution is used. As used herein an "aqueous solution" is a solution that is predominantly water and retains the solution characteristics of water. Where the aqueous solution contains solvents in addition to water, water is typically the predominant solvent. Further matter may be added to the aqueous solution, for example dissolved or suspended therein. As an illustrative example an aqueous solution may include one or more buffer compounds. Numerous buffer compounds are used in the art and may be used to carry out the various processes described herein. Examples of buffers include, but are not limited to, solutions of salts of phosphate, carbonate, succinate, carbonate, citrate, acetate, formate, barbiturate, oxalate, lactate, phthalate, maleate, cacodylate, borate, N-(2-acetamido)-2-amino-ethane-sulfonate (also called (ACES), N-(2-hydroxyethyl)-piperazine-N'-2-ethanesulfonic acid (also called HEPES), 4-(2-hydroxyethyl)-1-piperazine-propanesulfonic acid (also called HEPPS), piperazine-1,4-bis(2-ethanesulfonic acid) (also called PIPES), (2-[Tris(hydroxymethyl)-methylamino]-1-ethansulfonic acid (also called TES), 2-cyclohexylamino-ethanesulfonic acid (also called CHES) and N-(2-acetamido)-imino-diacetate (also called ADA). Any counter ion may be used in these salts; ammonium, sodium, and potassium may serve as illustrative examples. Further examples of buffers include, but are not limited to, triethanolamine, diethanolamine, ethylamine, triethylamine, glycine, glycylglycine, histidine, tris(hydroxymethyl)aminomethane (also called TRIS), bis-(2-hydroxyethyl)-imino-tris(hydroxymethyl)methane (also called BIS-TRIS), and N-[Tris(hydroxymethyl)-methyl]-glycine (also called TRICINE), to name a few. The buffers may be or be included in aqueous solutions of such buffer compounds or solutions in a suitable polar organic solvent. One or more respective solutions may be used to accommodate the suspected biological analyte molecule as well as other matter used, throughout an entire method of the present invention. Further examples of matter that may be added, include salts, detergents or chelating compounds.

In some embodiments an ionic liquid is used as the solvent or the main solvent such as ethylammonium nitrate or a dihydrogen phosphate ionic liquid. Various protic ionic liquids may be tested for their suitability as a solvent for carrying out a method of the invention. Protic ionic liquids are formed through the combination of a Brønsted acid and Brønsted base (see Greaves, T. L., & Drummond, C. J., *Chem. Rev.* (2008) 108, 206-237). Where an ionic liquid is used, the ionic liquid proton activity may be altered in situ according to standard methods. The ionic liquid proton activity corresponds to the pH value of an aqueous solution.

The detection method of the invention may be carried out in the form of a screening method, for example analyzing a plurality of samples in parallel, delayed and/or in succession. Any lactamase activity may be detected using the method of the invention. The method of the invention is suitable for detecting all, any selected or one selected class of β-lactamase, depending on the substrate used. β-Lactamases of all known classes, presently class A, class B, class C and class D may be detected. β-Lactam compounds have a beta lactam ring (supra) and may include additional rings such as a thiazolidine ring for penicillins, a cephem nucleus for cephalosporins or a double ring structure for carbapenems. The β-lactam antibiotics include six different structural subtypes, penams, cephems, monobactams, clavams, penems, and carbapenems. The penams include benzyl-penicillin and ampicillin. The cephems include classical cephalosporins such as cephaloridine, nitrocefin, and cefotaxime, as well as cephamycins, which are 7-α-methoxy-cephalosporins. The monobactams are monocyclic β-lactams and include aztreonam. The penems have a 2,3-double bond in the fused thiazolidine ring (hence dihydrothiazole), similar to the carbapenems (e.g., imipenem, biapenem), which also have an unsaturated fused five membered ring, with carbon instead of sulfur at the 1-position.

An overview on β-lactamase names has been given by Jacoby (*Antimicrob. Agents Chemother.* (2006) 50, 4, 1123-1129). The compound used may in some embodiments be selected to have a preference or a specificity for a certain class of lactamase. As explained above, β-lactamases are classified into classes A, B, C and D. Enzymes of class A, C and D utilize a serine residue in their active site that irreversibly reacts with the carbonyl atom of the β-lactam ring (supra). Class B β-lactamases or metallo β-lactamases use one or two divalent transition metal ions such as zinc ($Zn^{2+}$) to react with the carbonyl group of the amide bond of most penicillins, cephalosporins and carbapenems, but not monobactams. Metallo-β-lactamases can degrade all classes of β-lactams except monobactams and are special for their constant and efficient carbapenemase activity. Furthermore, they are not susceptible to therapeutic β-lactamase inhibitors. An overview on the mechanism of action, genetics and dissemination, and inhibitors of the four classes of β-lactamases has for example been given by Majiduddin et al. (*Int. J. Med. Microbiol.* (2002) 292, 127-137).

Class A β-lactamases preferentially hydrolyze penicillins and compounds of the invention having a 4+5 member ring structure such as e.g. of general formula (III) (for an overview on the selectivities of β-lactamases see e.g. Bush, K., et al., *Antimicrob. Agents Chemother.* (1995) 39, 1211-1233). However, some class A β-lactamases have a specificity for cephalosporins and compounds of the invention having a 4+6 member ring structure such as e.g. of general formula (II), other members of this class having a specificity for both or penicillins and cephalosporins. Class B β-lactamases have a broad specificity that covers most beta-lactam compounds. Class C β-lactamases mainly cleave cephalosporins and compounds of the invention having a 4+6 member ring structure such as e.g., of general formula (II). Class D β-lactamases mainly react with penicillins and compounds of the invention having a 4+5 member ring structure such as e.g. of general formula (III). It is noted that all the A-D β-lactamase enzymes are able to cleave the four membered ring of the β-lactam structure (supra). It can thus be concluded that differences in specificity and/or selectivity are most likely due to other portions of the β-lactam compounds.

The detection method of the invention may be carried out as a screening method for screening compounds for their suitability as β-lactamase modulators, e.g., β-lactamase inhibitors. Beta-lactamase activity may for example be detected in the presence of one or more potential modulators, e.g., inhibitors, if desired in a plurality of concentrations. Such a potential modulator may be a compound that is an inhibitor candidate or an activator candidate in that it is suspected to be capable of modulating, e.g. inhibiting beta-lactamase activity. The term "candidate compound" is meant to refer to any compound wherein the characterization of the compound's ability to modulate lactamase activity is desired. "Modulate" is intended to mean an increase, decrease, or other alteration of any or all lactamase activities or properties. In this regard an alteration may include a preference or a specificity for a certain class of lactamase (supra).

The detection method of the invention may also be used as a screening method with regard to the effect of the properties of the cleavage moiety, Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$ respectively (see above), on β-lactamase activity and/or on the sensitivity of a selected method of screening compounds for their suitability as β-lactamase modulators. As an illustrative example, a compound, or a group of compounds, with a desired β-lactamase modulatory activity may have been identified, for instance using the method of the invention, or may have been selected. The compound(s) may be of general formulas (I)-(III) or (VII)-(IX). For further tests it may be desired to investigate and/or optimize the effect of bridge A or G, respectively, of the compound(s). Derivatives of the compound(s) may then be synthesized, differing in their cleavage moiety. The selected technique for determining the presence of the cleavage moiety on the nanoparticulate tag may then be carried out using an embodiment the method of the invention. The plurality of derivatives may for example be analyzed in parallel, successively, or a combination thereof. In one embodiment a pre-screen may be carried out using groups of mixtures of such derivatives in one experiment. Using for instance an optically resonant nanoantenna and an optical beam, the immobilization of individual linking moieties on the nanoparticulate tag within each mixture may then be analyzed, for example in an automated manner. The average signals of the analyzed groups of mixtures, or the presence of particular high or low signals may then be compared between analyzed mixtures of derivatives. Metallic nanoparticles can also be coded with Raman active dyes that give each particle a unique Raman signature. If desired, each of the nanoparticles used may be equipped with such a dye for their retrieval, e.g. once a cleavage moiety has been immobilized thereon.

Using the method of the invention the effect of a respective compound on β-lactamase activity can be determined and thereby the suitability of the compound as a β-lactamase modulator can be analyzed. Such an embodiment of the method of the invention may be taken to be a method of identifying a compound that is capable of modulating beta-lactamase activity. Typically in such an embodiment of the method of the invention a known beta-lactamase activity is provided. A sample, such as a microorganism or a solution that includes a beta-lactamase enzyme, may for instance be used. As an illustrative example, a cell that expresses a selected β-lactamase may for instance be cultured and then used in the present method of the invention. The respective sample may further be known to be of a certain class of β-lactamase (supra). This class may be selected according to the desired preference or specificity of a candidate compound. In some embodiments a plurality of samples, each with a different class of β-lactamase activity, may be used. The method may further include contacting the sample with a candidate compound to be analyzed for its β-lactamase modulating activity. The candidate compound may for example be added to the sample, including to a solution that includes the sample. The method may further include contacting the sample with a nanoparticulate tag as described above. In some embodiments the candidate compound may first be added to the nanoparticulate tag, and the mixture thus formed may then be added to the sample. In some embodiments the nanoparticulate tag is first added to the sample and subsequently the candidate compound is added.

The present method further includes contacting the sample with a compound selected from one of general formulas (I) to (IX), including one of general formulas (X) to (XVIII) (see above). The compound of one of general formulas (I) to (IX) may be added before, together with or after adding the nanoparticulate tag. It may also be added before, together with or after adding the candidate compound. It should however be noted that once the compound of one of general formulas (I) to (IX) and the sample with beta-lactamase activity have been contacted, cleavage of the compound of one of general formulas (I) to (IX) is to be expected. It may therefore be desired to contact the sample and the candidate compound at the same time as or earlier than contacting the sample and the compound selected from one of general formulas (I) to (IX). This sequence prevents β-lactamase activity from acting on the compound of one of general formulas (I) to (IX) in the absence of the candidate compound, which may otherwise result in a background signal, thereby reducing the sensitivity of the method. As explained above, the method further includes allowing beta-lactamase activity in the sample to cleave a beta-lactam moiety of the compound of one of general formulas (I) to (IX). A cleavage moiety Z-A-Z, Z-A-Z—$R^{15}$, Z-A-Z—$R^{16}$, Z-A-Z—$R^{17}$, Z-A-Z—$R^{18}$ or Z-G-N($R^8$)$R^9$, respectively, is released (supra), which is allowed to be immobilized on the surface of the nanoparticulate tag (supra). The presence of beta-lactamase activity is determined based on the presence of the cleavage moiety, e.g. Z-A-Z, Z-G-N($R^8$)$R^9$, etc., immobilized onto the surface of the nanoparticulate tag. Thereby the method includes determining the capability of the candidate compound to modulate lactamase activity and thus analyzing the suitability of the compound as a beta-lactamase modulator. The method may for example be used as a method of identifying a cell that has a resistance to one or more β-lactam antibiotics. The method may also be used to screen compound libraries, e.g. using conventional high-throughput screening technologies, to identify molecules that will alter β-lactamase activity.

In this context, it is noted that β-Lactamase resistance enables microorganisms to outlast antibiotics and is a continuing problem in medical therapy. Increasing resistance to all currently available antibiotics is observed with no new antibiotics with novel mechanisms expected to be developed in the foreseeable future (for a recent overview on multi-drug-resistance of gram-negative bacilli in North America see e.g., Nicasio, A. M., et al., *Pharmacotherapy* (2008) 28, 2, 235-249). An extensive and sometimes irresponsible use of β-lactam antibiotics in clinical and agricultural settings have contributed to the fast emergence and spread of resistant microorganisms, in particular gram-negative pathogens such as Enterobacteriaceae, *Pseudomonas aeruginosa* and *Acinetobacter*. Extended-spectrum β-lactamases have evolved as a result of point mutations in β-lactamase genes (e.g., Gniadkowski, M., *Clin. Microbiol. Infect.* (2008) 14 (Suppl. 1), 11-32), allowing them to hydrolyze a number of antibiotics of the latest generation such as cephalosporins and monobactams. Resistant microorganisms have spread worldwide, including in the US and Canada (see, e.g., Bush, *Clin. Microbiol. Infect.* (2008) 14 (Suppl. 1), 134-143) or Europe (see e.g., Cantón, R., et al., *Clin. Microbiol. Infect.* (2008) 14 (Suppl. 1), 144-153). Extended-spectrum β-lactamases are inhibited by clavulanic acid and other inhibitors of class A β-lactamases, such as sulbactam and tazobactam. Thus, the present invention can be used to determine whether microorganisms have developed resistance against known antibiotics, or alternatively, to determine, whether a known antibiotic is still capable of exert its antibiotic activity against a particular microorganism. The latter approach (screening of available antibiotics) is advantageous since such "re-screening" of antibiotics is certainly faster than developing a new antibiotic (although identifying such new antibiotics by means of a screening assay as described herein is of course also encompassed by the present invention).

The present method of the invention may include comparing the obtained results with those of a control measurement. Such a control measurement may be a measurement in which no candidate compound is added. As a further example of a respective control measurement, a compound that is known to be unable to alter β-lactamase activity may for instance be used. An illustrative example of such a "control" compound is a derivative or a structurally similar molecule that has previously been identified as not affecting the activity of any β-lactamase or of a certain β-lactamase of interest. A control measurement may also include the use of a modulator that is known to activate or inhibit the β-lactamase activity to be analyzed. A β-lactamase inhibitor of known specificity and activity may for instance be used. In such embodiments the method may identify a candidate compound as a modulator of β-lactamase activity based upon an amount of signal produced as compared to a control sample. If the two measurements, i.e., the measurement of the compound suspected to be suitable as a beta-lactamase modulator and the control measurement, differ in such a way that the difference between the values determined is greater than a pre-defined threshold value, the respective compound is taken to have β-lactamase modulatory activity. In such a case a β-lactamase modulator is identified.

Identifying a compound that is capable of modulating beta-lactamase activity may be carried out on a plurality of samples in parallel, delayed and/or in succession. A respective method may be a method of screening candidate compounds for an ability to modulate beta-lactamase activity. Compounds can be screened individually or in pools of a few, tens or hundreds of compounds. Compounds for screening can be contained within large libraries of compounds, for instance in embodiments where high-throughput in vitro screening formats are used. Methods for producing large libraries of chemical compounds, including simple or complex organic molecules, metal-containing compounds, carbohydrates, peptides, proteins, peptidomimetics, glycoproteins, lipoproteins, nucleic acids, antibodies, and the like, are well known in the art. Where desired a library of compounds can be screened sequentially, in a multi-sample format, in which each sample receives one compound, or multiplexed format, in which each sample receives more than one compound.

Any number of steps of the present method of the invention, including the entire method, may be performed in an automated way—also repeatedly, using for instance commercially available robots. As an illustrative example, the method may be an in-vitro screening method, for example carried out in multiple-well microplates (e.g. conventional 48-, 96-, 384- or 1536 well plates) using automated work stations. The method may also be carried out using a kit of parts, for instance designed for performing the present method (see below).

The present invention also provides a kit for detecting β-lactamase activity, which may for instance be a diagnostic kit. A respective kit includes a compound of one of general formulas (I)-(III) or (VII)-(IX) (supra). Several such compounds may be included in a kit, e.g. one or a plurality of a compound of general formula (I), one or a plurality of formula (II) and one or a plurality of formula (III). A kit according to the present invention furthermore includes a nanoparticulate tag as described above. In some embodiments the kit also includes means for determining the presence of beta-lactamase activity based on the presence of the cleavage moiety Z-A-Z, Z-A-Z—$R^{15}$, Z-A-Z—$R^{16}$, Z-A-Z—$R^{17}$ or Z-G-N($R^8$)$R^9$ immobilized onto the surface of the nanoparticulate tag. As described above, which cleavage moiety is being immobilized on the nanoparticulate tag depends on the compound included in the kit that was used to carry out the method of the invention. As an illustrative example, where a compound of general formula (II) is used, usually a cleavage moiety Z-A-Z—$R^{16}$, in some embodiments a cleavage moiety Z-A-Z (supra), is immobilized on the nanoparticulate tag, unless $R^{16}$ undergoes a further reaction such as hydrolysis. The kit may be used to carry out a method according to the present invention. Typically the kit is suitable for carrying out the method of the invention in an aqueous solution or in an ionic liquid (see above for details). In this regard the kit may include instructions for detecting (including quantifying) β-lactamase activity, for example in form of an instruction leaflet. It may include one or more devices for accommodating the above components before, while carrying out a method of the invention, and thereafter.

The invention is further illustrated by the following figures and non-limiting examples. Some of these examples together with additional illustrations have been disclosed by the present inventors (Liu, R., et al.) in *Angew. Chemie Int. Ed.* (2007) 46, 8799-8803 (DOI: 10.1002/anie.200702773) and the corresponding supporting information online, available at http://www.angewandte.org. This journal article and its supporting information online are incorporated by reference herein in their entirety for all purposes.

EXEMPLARY EMBODIMENTS OF THE INVENTION

FIG. 1 illustrates the method of using a nanoparticulate tag to detect β-lactamase (Bla). In the depicted examples a plurality of gold nanoparticles (Au-NPs) is shown as the nanoparticulate tag, FIG. 1A depicts an embodiment of the method in which a cephalosporin compound with two cephem nuclei is used as the substrate. The substrate is not capable of forming a covalent bond to the nanoparticles. Cleavage of the β-lactam ring in the substrate triggers spontaneous elimination of any leaving groups previously attached to the 3'-position. As a result a cleavage product that includes the linker is formed. This cleavage product has two functional groups ZH, which are capable of forming a covalent bond to the nanoparticles. Z may for instance be sulfur, in which case thiol groups are formed. In the non-cleaved substrate used in the method, two cephem nuclei are connected through a dithiol-modified 1,2-bis(2-aminoethoxy)ethane flexible linker after iodo substitution. The thiol group is an excellent leaving group and will facilitate fragmentation upon enzyme treatment. Furthermore a thiol group is capable of strong interactions with gold surfaces. The free thiol and amino groups in the released fragment lead to the aggregation of gold nanoparticles based on the cross-linking reactions, and thus demonstrate the significant color change from red to blue. This red-shifting aggregate can be used as a colorimetric sensor to identify β-lactamase activity in the absence and presence of the inhibitors. The efficiency of the enzyme activity inhibition can be screened based on the specific color changes.

FIGS. 1C and 1E depict embodiments in which the substrate molecule contains only one cephem nucleus. In embodiments where the linker is connected to the moiety —Z—R⁸ and where R⁸ is different from H, the substrate is again not capable of forming a covalent bond to the nanoparticles (see FIG. 1C). The same applies to embodiments where the linker is connected to the moiety —N(—R⁸)—R⁹ and where both R⁸ and R⁹ are different from H (cf. FIG. 1E). The formed cleavage product, which includes the linker, is capable of forming a covalent bond to the nanoparticles via its ZH-group. The linker or one of moieties R⁸ and R⁹ may further be sensitive to selected reaction conditions under which a further cleavage may occur, thereby forming an additional group that is capable of associating to the nanoparticles—including of forming a covalent bond therewith. In such embodiments aggregation of the nanoparticles occurs.

In embodiments where the linker is connected to the moiety —N(—R⁸)—R⁹ and where at least one of R⁸ and R⁹ is H, the substrate is typically capable of forming a covalent bond to the nanoparticles (see FIG. 1E). Thus immobilization of the substrate occurs in the presence or absence of β-lactamase activity, or in the presence or absence of an inhibitor where a β-lactamase enzyme is added. Cleavage of the substrate leads to the formation of a group ZH, which may for instance be a thiol group. As a result aggregation of the nanoparticles occurs. The substrate may for example be the following compound (substrate 3):

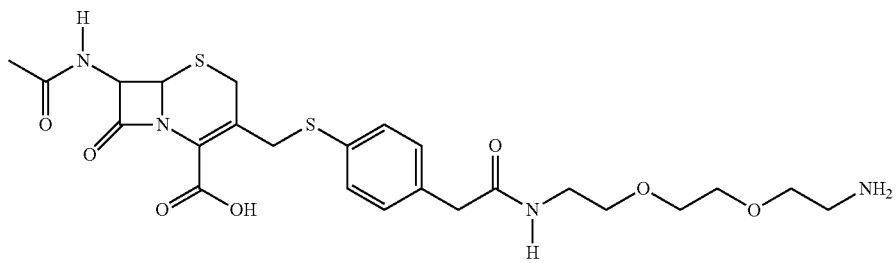 [SMILES: CC(=O)NC1C(=O)N2C(C(=O)O)=C(CSc3ccc(CC(=O)NCCOCCOCCN)cc3)CSC12]

In this embodiment a flexible 2-(4-mercaptophenyl) acetic acid coupled 1,2-bis(2-aminoethoxy) ethane linker is connected to the 3'-position of cephalosporin through iodo-thiol substitution. As an excellent leaving group, the thiol group facilitates the release of the fragment on the β-lactam ring upon the enzyme hydrolysis. The free thiol and positively charged amino groups in the released fragment lead to the aggregation of gold nanoparticles based on the cross-linking reactions, and thus demonstrate the significant color change from red to blue. This red-shifting aggregate can be used as a colorimetric sensor to identify Bla activity in the absence and presence of the inhibitors. The efficiency of the enzyme activity inhibition can be screened based on the specific color changes.

In an illustrative embodiment of the method depicted in FIG. 1A, 1,2-Bis(2-aminoethoxy)ethane was used as the linker to improve the substrate solubility and to minimize the steric interactions between the substrates and the enzyme. To optimize the kinetic properties of the substrates, two different thiol groups, 2-mercaptoethylamine- and 4-aminothiolphenol-conjugated 1,2-bis(2-aminoethoxy)ethane linkers, were connected to the 3'-position of the cephem nucleus. A simple deprotection (that is, removal of the diphenyl methyl ester at the 4'-position by trifluoroacetic acid and anisole) followed by HPLC purification produced the substrates 1 and 2 with yields of 60 and 66.7%, respectively (FIG. 2A).

Figure 2B:
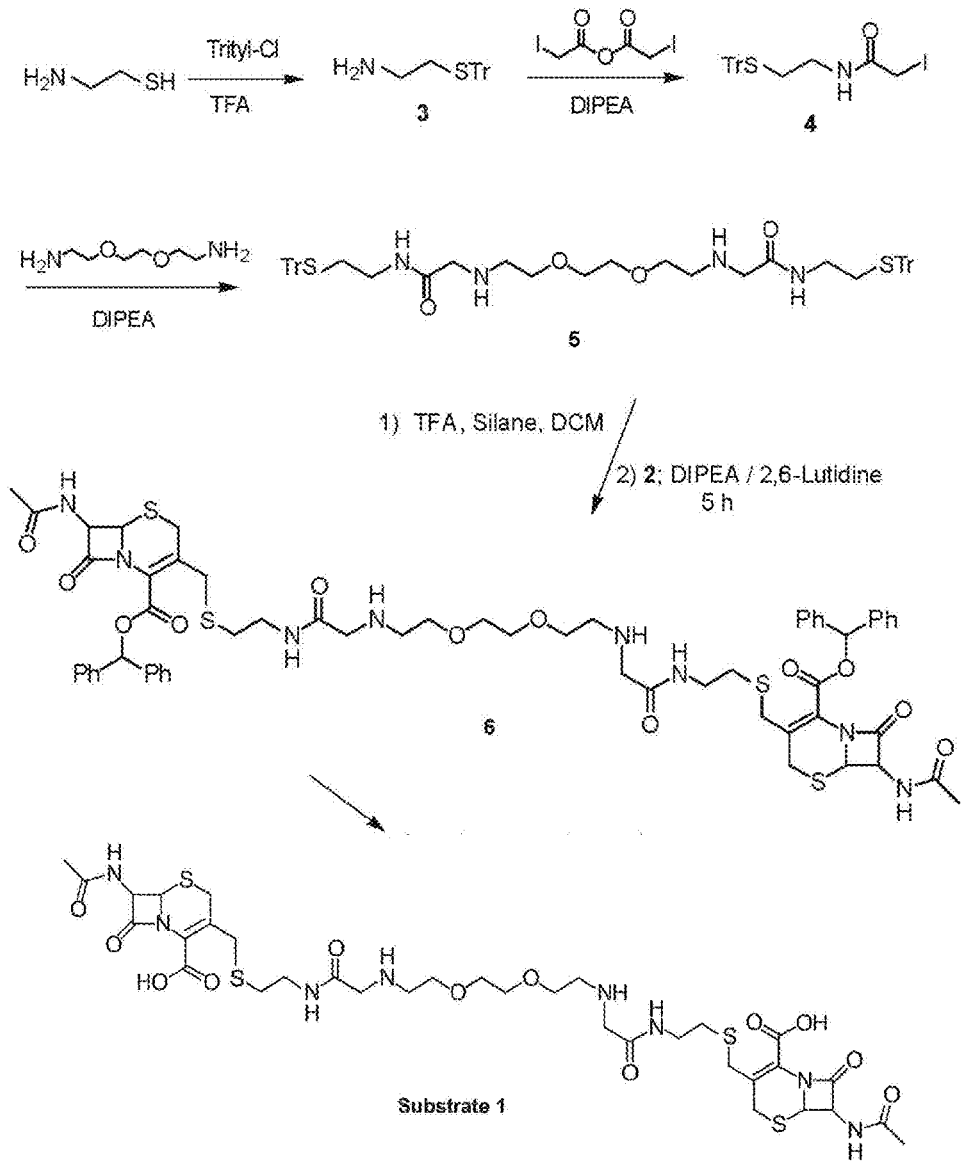
FIG. 2B depicts the synthesis of substrate 1 (see Example 1) from 3,6-dioxaoctyl-1,8-diamine and 2-aminoethanethiol.

FIG. 2B depicts the synthesis of substrate 1 from 3,6-dioxaoctyl-1,8-diamine and 4-[(triphenylmethyl)thio]-benzeneacetic acid (3). Compound 3 is prepared from 4-mercaptophenylacetic acid.

FIG. 2C depicts the synthesis of substrate 2 from 4-aminothiolphenol (DIPEA=N, N-diisopropylethylamine).

Figure 3:
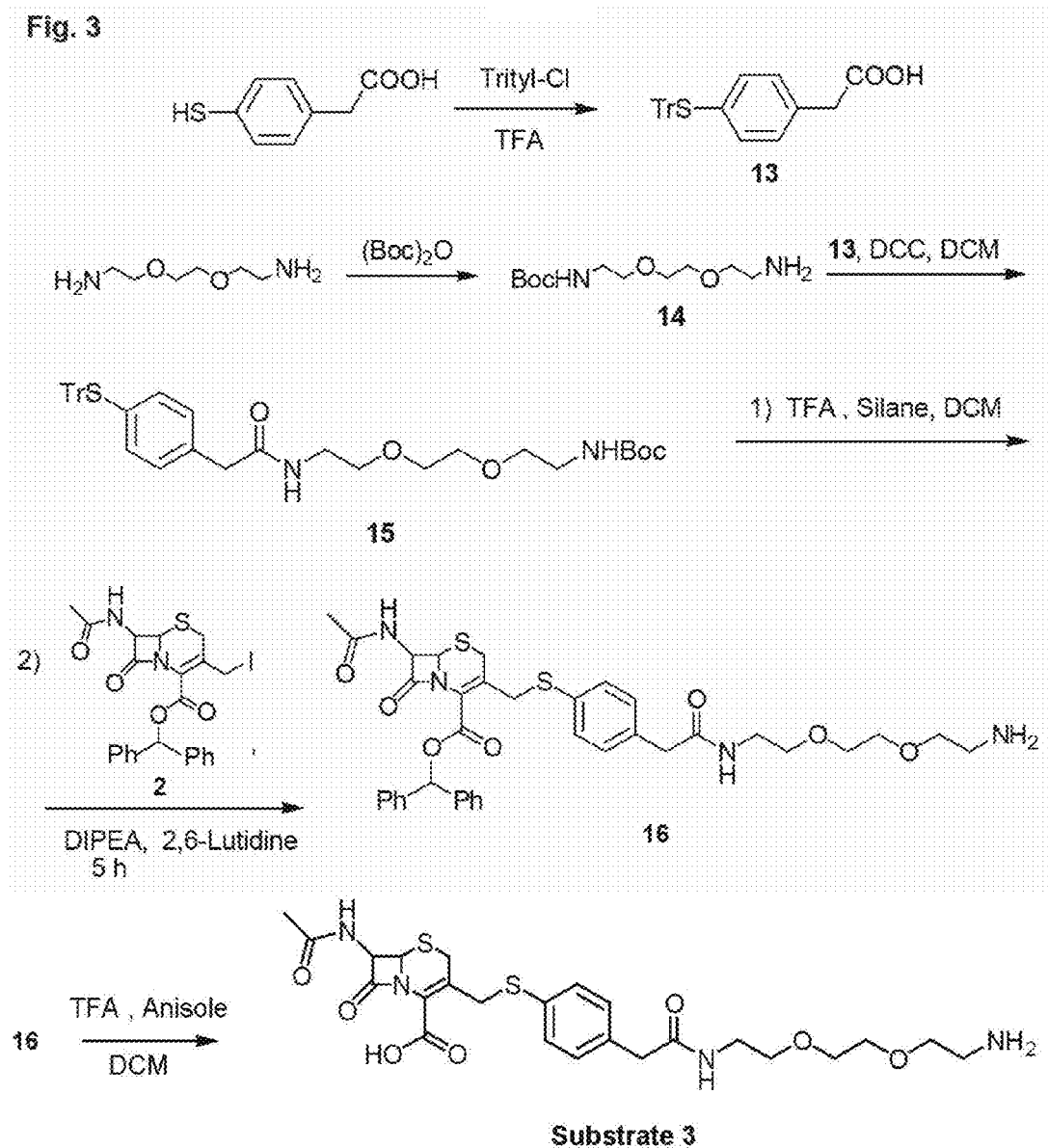
FIG. 3 depicts the synthesis of substrate 3 (see Example 3) from 3,6-dioxaoctyl-1,8-diamine and 4-mercaptophenylacetic acid.

FIG. 3 depicts the synthesis of substrate 3 from 3,6-dioxaoctyl-1,8-diamine and 4-mercaptophenylacetic acid.

Figure 4B:
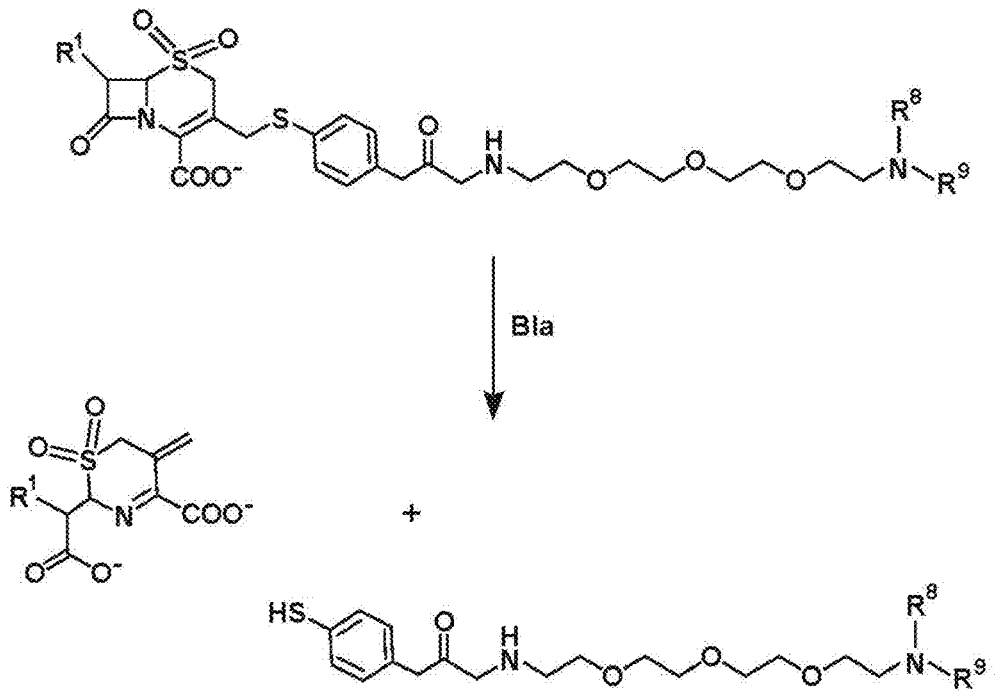
FIG. 4B illustrates the reaction of the cleavage of an embodiment of a compound of general formula (VII) by lactamase activity.
Figure 4C:
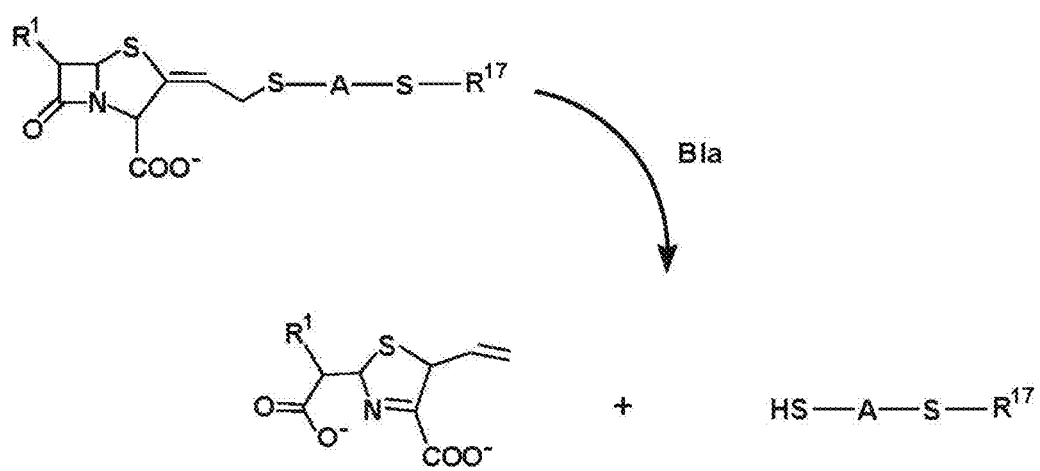
FIG. 4C illustrates the reaction of the cleavage of an embodiment of a compound of general formula (IX) by lactamase activity.

FIG. 4A illustrates the suggested reaction mechanism of the cleavage of substrate 1 by the β-lactamase enzyme. FIG. 4B and FIG. 4C further illustrate the cleavage reaction of a compound of general formula (VII) and of general formula (IX), respectively, by the lactamase enzyme.

Figure 5A:
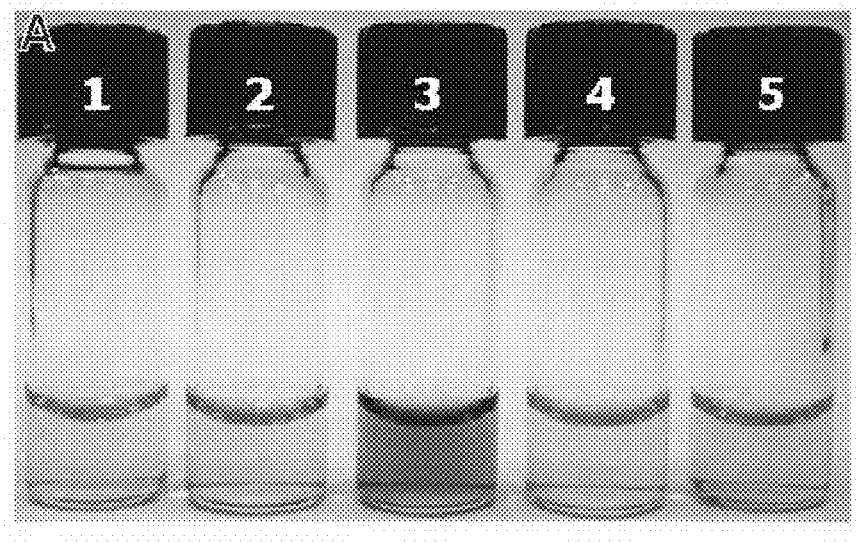
FIG. 5A depicts the coloring of a solution of gold nanoparticles in the absence or presence of Bla treated substrates (1: gold nanoparticles only; 2: gold nanoparticles+substrate 2; 3: gold nanoparticles+Bla treated substrate 2; 4: gold nanoparticles+substrate 1; 5: gold nanoparticles+Bla treated substrate 1).
Figure 5B:
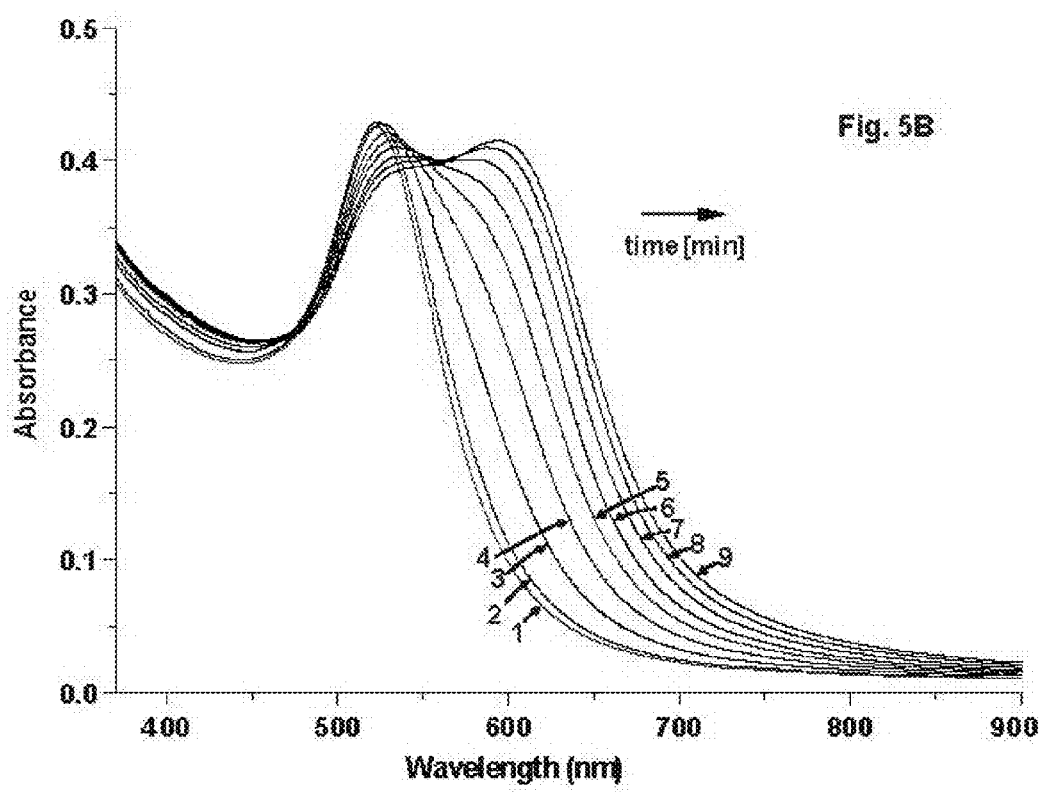
FIG. 5B depicts UV/Vis spectra of gold nanoparticles at each 2 min for 30 min after the addition of Bla (5.0 nM) treated substrate 2 (40 μM).
Figure 5C:
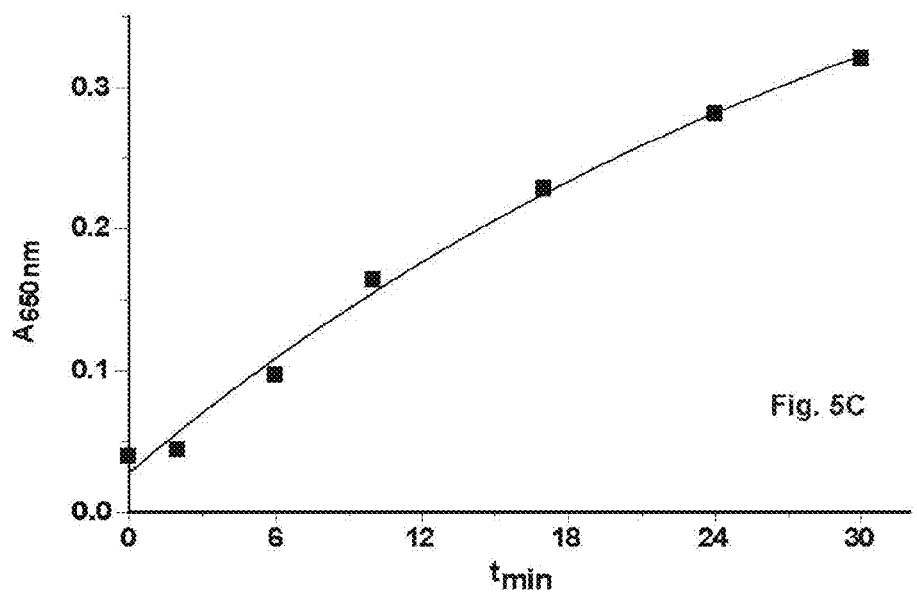
FIG. 5C shows the increase in absorbance at 650 nm up to 30 min after the addition of Bla (5.0 nM) treated substrate 2 (40 μM).

FIG. 5 depicts the colorimetric effect of β-lactamase inhibition in the method of the invention. Substrates (8 μm) were initially incubated with β-lactamase (5 nm) in phosphate buffered saline (PBS) buffer solution (pH 7.4) for 20 minutes. Then, the resulting solutions were transferred into suspensions of gold nanoparticles (15 nm in size and with a concentration of 2.6 nm as determined by method previously used in the art (Jin, R., et al., *J. Am. Chem. Soc.* (2003) 125, 1643-1654). To stabilize the nanoparticles and also to prevent the interaction of proteins with gold particles, 0.1% poly(ethylene glycol) (PEG) 8000 was added to the reaction mixture (Guarise, C., et al., *Proc. Natl. Acad. Sci. USA.* (2006) 103, 3978-3982). FIG. 5A shows colors of the gold nanoparticles solution in the absence or presence of β-lactamase treated substrates; 1: gold nanoparticles only; 2: gold nanoparticles and substrate 2; 3: gold nanoparticles and Bla treated substrate 2; 4: gold nanoparticles and substrate 1; 5: gold nanoparticles and Bla treated substrate 1. The color of the suspension of gold nanoparticles alone remained unchanged over time. When the intact substrates were added, no further color changes of the gold nanoparticles demonstrated that both of the β-lactam substrates were stable under the experimental conditions. In the presence of the Bla-pretreated substrate 1, no color change was detected within 30 minutes. A clear change was only observed after a longer incubation time (>9 h; data not shown). In contrast thereto, after adding the Bla-pretreated substrate 2 into the gold nanoparticles, the color dramatically changed from pink red to violet blue within seconds, visible in the grey scale image by a darkening of the liquid. FIG. 5B shows UV/Vis spectra of gold nanoparticles at each 2 min for 30 min after the addition of β-lactamase (5.0 nM) treated substrate 2 (40 μM). Significant changes in the UV/Vis absorption were identified 30 minutes after mixing the enzyme-treated substrate 2 with the gold nanoparticles. Above about 580 nm (corresponding to yellow color) absorbance increased with time. Both a decreased absorbance of the plasmon band at 520 nm (corresponding to red color) and an increased absorbance at 650 nm (corresponding to blue color) were observed with increasing time. The shifting of the absorbance to a longer wavelength over time correlated with the color change seen in FIG. 5A. FIG. 5C shows the increase in absorbance at 650 nm up to 30 min after the addition of β-lactamase (5.0 nM) treated substrate 2 (40 μM).

Figure 6:
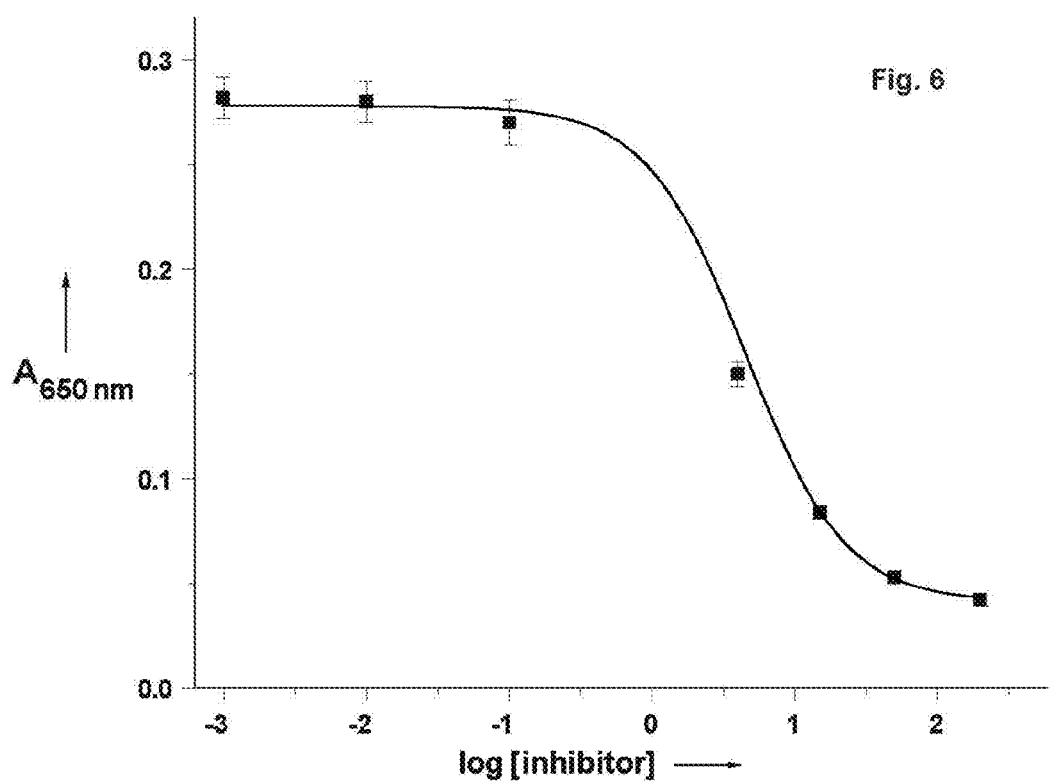
FIG. 6 depicts the effect of the Bla inhibitor sulbactam, monitored by the absorbance change at 650 nm.

FIG. 6 depicts the effect of the β-lactamase inhibitor sulbactam, monitored by the absorbance change at 650 nm (analyses were performed in triplicate). The $IC_{50}$ value was found to be about 4.4 μm, which is similar to the previously reported value (Bush, K., et al., *Antimicrob. Agents Chemother.* (1995) 39, 1211-1233).

Figure 7:
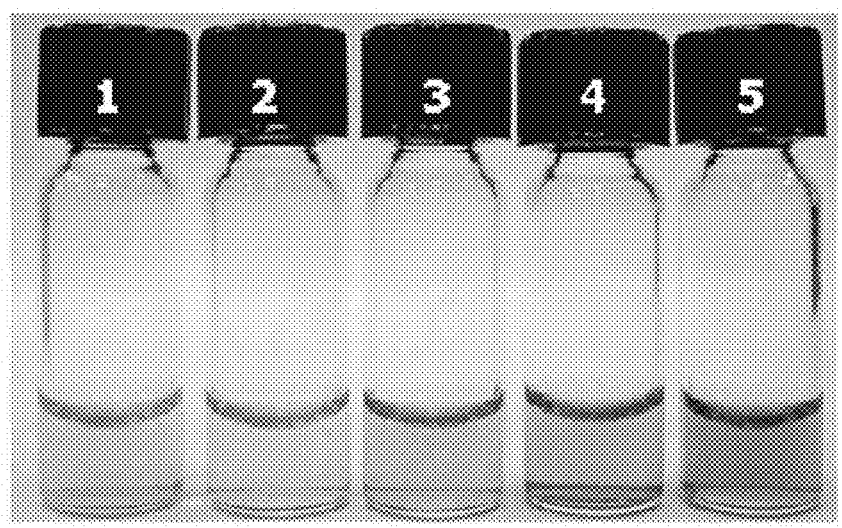
FIG. 7 shows vials containing gold nanoparticles, 20 min after different Bla concentrations were added. (1: suspension of gold nanoparticles without substrate; 2: gold nanoparticles mixed with 0 μM Bla treated substrate 2; 3: gold nanoparticles and 60 pM Bla treated substrate 2; 4: gold nanoparticles and 1.0 nM Bla treated substrate 2; 5: gold nanoparticles and 5.0 nM Bla treated substrate 2).

FIG. 7 illustrates the aggregation kinetic of gold nanoparticles after mixing with different Bla concentrations within 20 min. 10 μL β-lactamase solution was mixed with 19 μL of substrates for the enzyme interactions. 1: suspension of gold nanoparticles without substrate; 2: gold nanoparticles mixed with 0 μM Bla treated substrate 2; 3: gold nanoparticles and 60 pM Bla treated substrate 2; 4: gold nanoparticles and 1.0 nM Bla treated substrate 2; 5: gold nanoparticles and 5.0 nM Bla treated substrate 2. The final substrate concentrations were maintained at 8 μM. The enzymatic reaction was performed by incubating the different Bla concentration with substrates for 20 min at room temperature. All the tests were performed in triplates.

Figure 8:
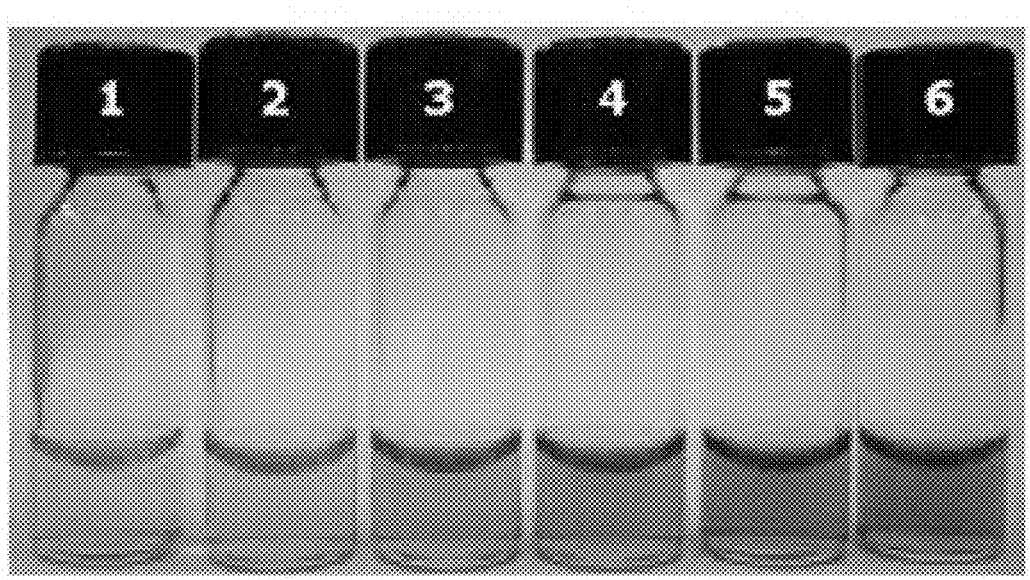
FIG. 8 shows vials containing gold nanoparticles after mixing with different concentrations of substrate 2, 20 min after different Bla concentrations were added (1: suspension of gold nanoparticles without substrate; 2: gold nanoparticles mixed with 4 μM of Bla treated substrate 2; 3: 6 μM of Bla treated substrate 2; 4: 8 μM of Bla treated substrate 2; 5: 10 μM of Bla treated substrate 2; 6: 12 μM of Bla treated substrate 2).

FIG. 8 illustrates the aggregation kinetic of gold nanoparticles after mixing with different concentrations of substrate 2. 10 μL Bla solution was mixed with 190 μL of different concentrations of substrates for the enzyme interactions. 1: a suspension of gold nanoparticles without substrate; 2: gold nanoparticles mixed with 4 μM of Bla treated substrate 2; 3: 6 μM of Bla treated substrate 2; 4: 8 μM of Bla treated substrate 2; 5: 10 μM of Bla treated substrate 2; 6: 12 μM of Bla treated substrate 2. The enzymatic reaction was performed by incubating the different concentration of substrate with Bla for 20 min at room temperature.

FIG. 9 depicts a further example of the colorimetric effect of β-lactamase inhibition in the method of the invention. FIG. 9A shows UV-Vis spectra of gold nanoparticles before (a) and after (b) incubation with Bla treated substrate in the absence of inhibitor. FIG. 9B shows a similar test as FIG. 9A, but in the presence of an inhibitor (0.1 μM). The insets show the color change of gold nanoparticles. 1: gold nanoparticles only; 2: gold nanoparticles, Bla and substrate; 3: gold nanoparticles only; 4: gold nanoparticles, Bla, inhibitor and substrate.

Figure 10A:
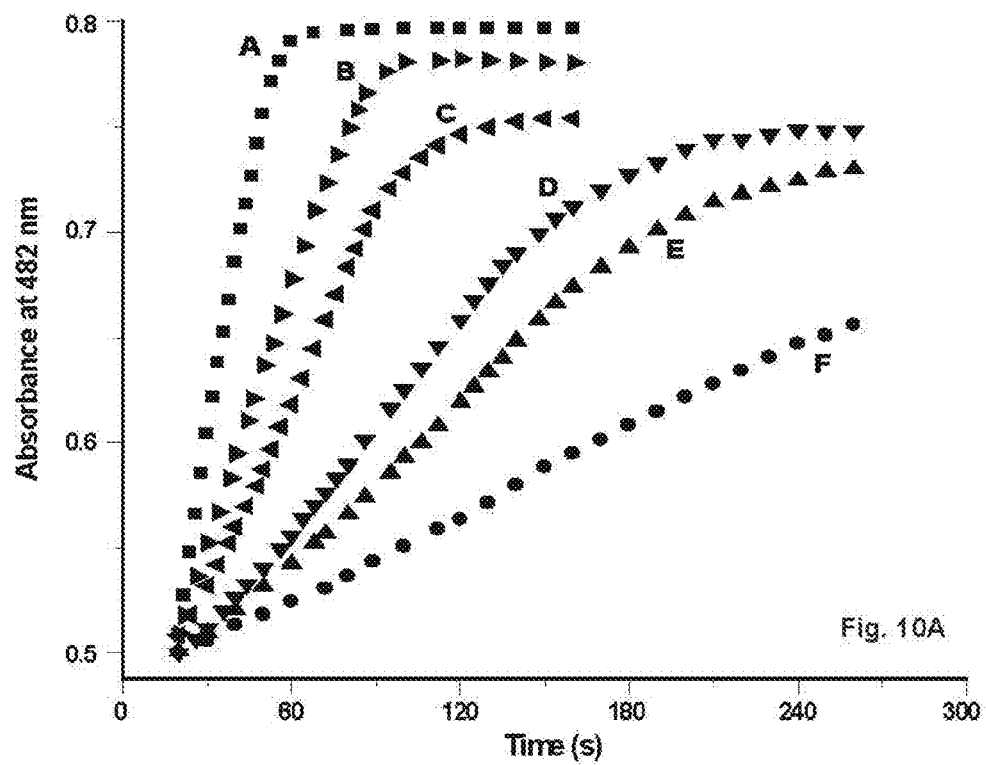
FIG. 10A depicts the nitrocefin based detection of Bla activity (P99 *Enterobacter cloacae* beta-lactamase) using substrate 3 in the absence and presence of different inhibitors (A: no inhibitor, B: clavulanic acid, C: ceftazidime, D: Sulbactam, E: tazobactam, F: aztreonam).

FIG. 10A depicts the absorbance change (at 482 nm) in a nitrocefin based β-lactamase inhibition assay. Nitrocefin is a chromogenic β-lactamase substrate sensitive to hydrolysis by lactamases. Its hydrolysis can be conveniently monitored by a distinctive color change from yellow ($\lambda_{max}$=390 nm at pH 7.0) to red ($\lambda_{max}$=486 nm at pH 7.0). Nitrocefin hydrolysis was monitored using substrate 3 in the absence and presence of different inhibitors (40 μM): A: no inhibitor, B: clavulanic acid (CA), C: ceftazidime (TAZ), D: Sulbactam (SUL), E: tazobactam (TZB), F: aztreonam (ATM). The inhibitors are of the following structural formulas:

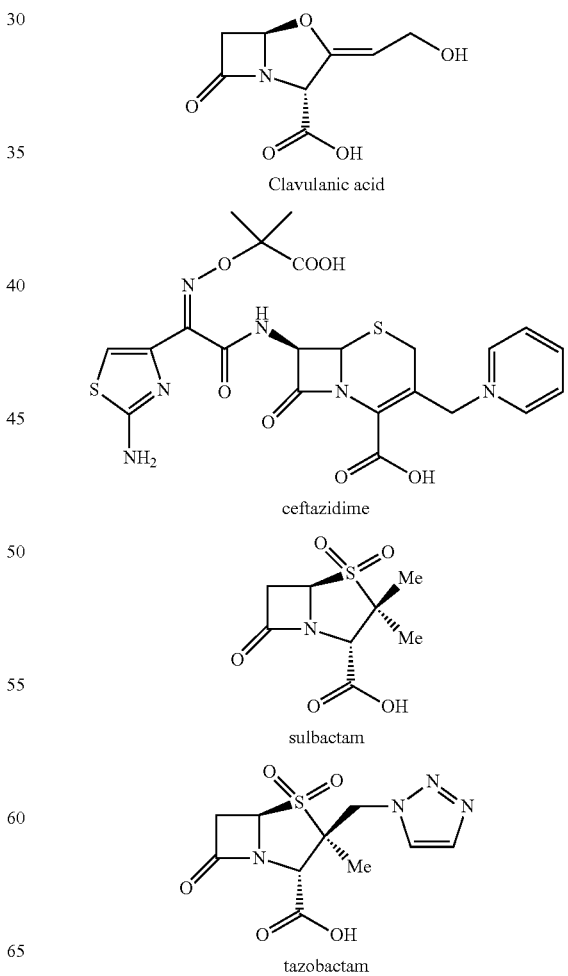

Clavulanic acid ceftazidime sulbactam tazobactam

-continued

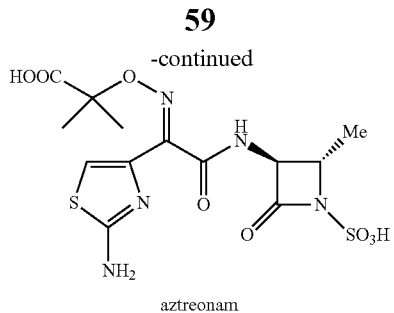

aztreonam

Figure 10B:
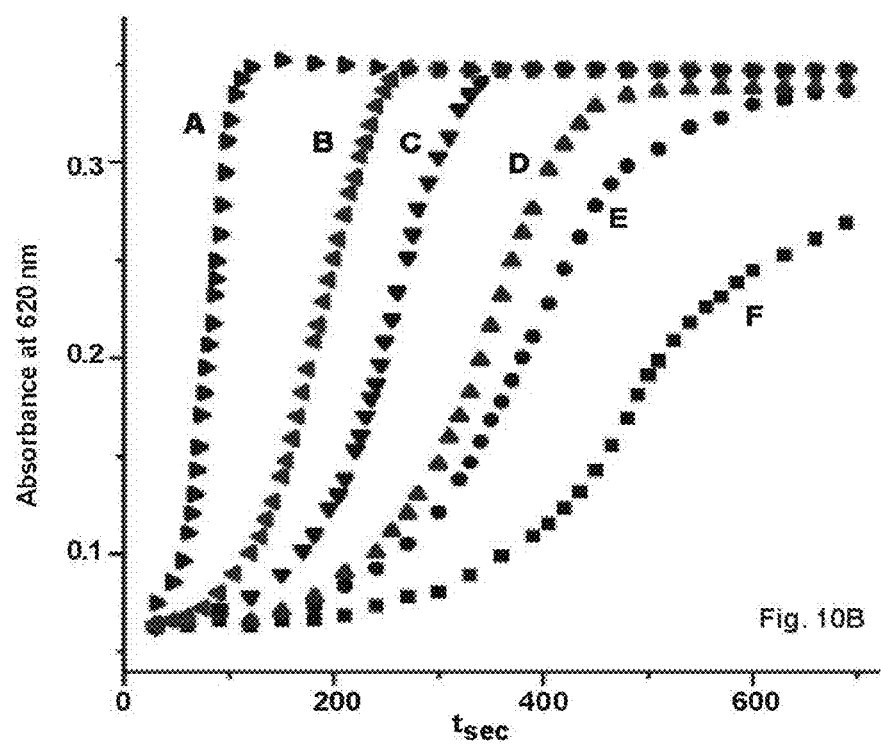
FIG. 10B depicts the gold nanoparticles based detection of Bla activity (P99 *Enterobacter cloacae* beta-lactamase) using substrate 3 in the absence and presence of different inhibitors (cf.

FIG. 10B depicts the effect of Bla inhibition on the absorbance change in the gold nanoparticles based method, using substrate 3 in the absence and presence of different inhibitors (0.25 μM). A: no inhibitor, B: clavulanic acid (CA), C: ceftazidime (TAZ), D: Sulbactam (SUL), E: tazobactam (TZB), F: aztreonam (ATM).

FIG. 11 depicts a comparison of the colorimetric effect of Bla inhibition in vitro using gold nanoparticles (Au-NPs) (2.5 nM) and using nitrocefin (40 μM) at a Bla concentration of 2 nM using 4 μM of substrate 3. A digital photo was taken and saved in the CMYK and in the RGB format. A: Lightness of red and green colors was set to maximum and thus only shadows and blue coloring depicted. B: Lightness of blue and green colors was set to maximum and thus only shadows and red coloring depicted. C: Lightness of cyan and magenta was set to maximum and thus only shadows and yellow coloring depicted. Optical appearance of the samples is indicated on top of each sample. The inhibitor used is indicated below each sample (cf. legend of FIG. 8). A red solution reveals enzyme inhibition, while the blue solution indicates the aggregation of gold nanoparticles induced by the enzymatic reaction. The inhibitors decreased the β-lactamase activities and exhibited the following trend for enzyme inhibition: TZB>CA>SUL. TAZ and ATM exhibit the lowest activity. This is consistent with the results by using standard indicator: Nitrocefin only when the inhibitor concentrations are larger than 3.5 μM (see FIG. 12). FIG. 11 D is a graphical representation of the ratio of the absorbance change ($A_{620nm}/A_{520nm}$) of Bla inhibition assay in the absence and presence of different inhibitors (inhibitor concentration: 0.1 μM). At low concentrations no color difference is observed in the conventional method using nitrocefin. The results indicate that the method of the invention, in an embodiment as a gold nanoparticles based enzyme inhibition assay, has the potential to efficiently screen inhibitor activity.

FIG. 12 depicts the colorimetric effect of Bla inhibition in vitro using gold nanoparticles (2.5 nM) and substrate 3 in a 96-well microplate. Different inhibitors (indicated above the sample, n.i.=no inhibitor) were used on four β-lactam resistant bacteria that contained class A Bla (indicated on the right, I: transformed E. coli; II: TEM-1 E. coli; III: B. cereus; IV: K. pneumoniae). Bacteria without inhibitor were used as positive control. Wild type E. coli Bl21 and gold nanoparticle solutions were used as negative controls. The final concentration of substrate and inhibitors were maintained at 8 μM and 0.1 μM, respectively. Appearance in blue (A), red (B) and yellow (C) is shown. A digital photo was taken and saved in the CMYK and in the RGB format. A: Lightness of red and green colors was set to maximum and thus only shadows and blue coloring depicted. B: Lightness of blue and green colors was set to maximum and thus only shadows and red coloring depicted. C: Lightness of cyan and magenta was set to maximum and thus only shadows and yellow coloring depicted. Optical appearance of the samples is indicated below each sample. The inhibitor/reference used is indicated on top of each sample (cf. legend of FIG. 8).

FIG. 13 depicts the colorimetric detection of Bla activity using substrate 3 and nitrocefin (40 μM). The concentration of inhibitors (see FIG. 12) was maintained at 3.5 μM, which was larger than that used in the method employing nanoparticles. The same bacteria were used as in FIG. 12 (see above), color presented as in FIG. 12.

FIG. 14 depicts the time course for the color change of the gold nanoparticles upon the addition of Bla-pretreated substrates. FIG. 14A shows the absorbance change (at 650 nm) of a suspension of gold nanoparticles with time in the presence of Bla-pretreated substrates (5 mm): substrate 1 (■, see FIG. 2B), substrate 2 (●, see FIG. 2C). For substrate 1, the absence of a significant color change within 30 minutes demonstrates the slow process of the overall enzyme assay. For substrate 2, about two thirds of the change in the total absorbance occurred within the first five minutes. Accordingly, this reaction process was very fast. FIG. 12B shows the dependence of absorbance change on time for the interactions of free dithiol linkers (5 mm) with the suspension of gold nanoparticles, the two linkers (▲, ○) are indicated in the figure: (▲=di-2-mercaptoethylamine-conjugated 1,2-bis(2-aminoethoxy)ethane, ○=di-4-aminothiolphenol-conjugated 1,2-bis(2-aminoethoxy)ethane). Both of the linkers exhibited similar affinities to that of the gold nanoparticles, and their binding was rapid, occurring within seconds.

FIG. 15 shows the quantitative relationship between the absorbance change (($A-A_0)/A_0$) at 650 nm and different concentrations of gold particles towards 60 pm Bla. Absorbance was measured at 2 h after mixing 60 pm Bla-pretreated substrate 2 (8 mm) with various concentrations of gold particles (ranging from 0.65, 1.3, 2.2, 2.6, 3.0, 3.4, 4.0, 4.8, to 10.4 nm; analyses were performed in triplicate). The significant change in the absorbance at the gold nanoparticle concentrations ranging from 1.0 to 4.0 nm indicates a high sensitivity for the colorimetric enzyme assay for Bla. The largest change in absorbance from dispersed to fully aggregated nanoparticles was observed when the concentration of gold nanoparticles was approximately 2.6 nm.

FIG. 16 depicts the absorbance at 620 nm of gold nanoparticles, in the presence of substrate 3 (8 μM), pretreated for 20 min with a range of concentration of TEM-1Bla. After incubating Bla solution with substrate 3 for 20 min at room temperature, the mixture was transferred into a suspension of gold nanoparticles. The absorbance at 620 nm was measured by UV spectrophotometry.

Figure 17B:
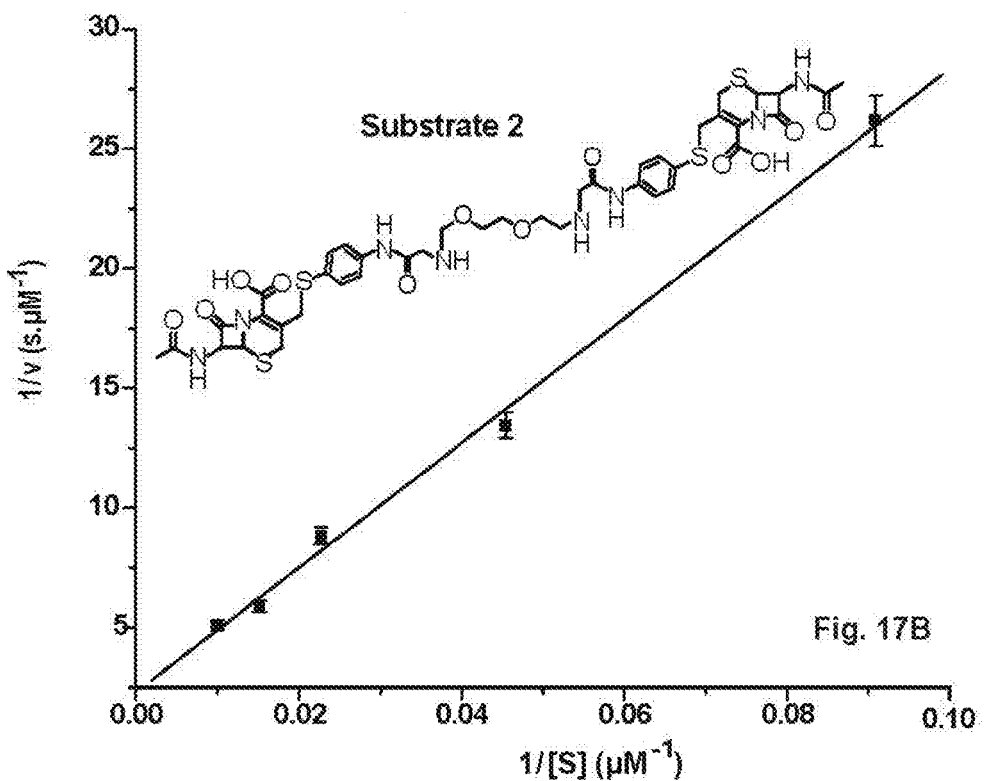
Figure 17C:
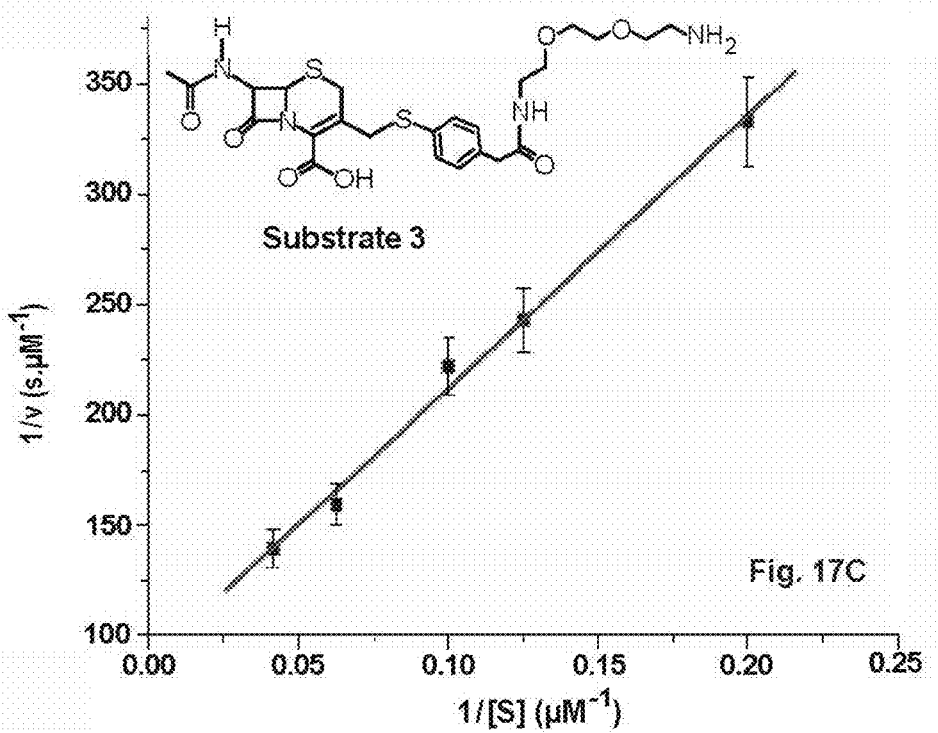

FIG. 17 depicts the kinetics data of the gold particle based colorimetric method as a double reciprocal plot of substrates hydrolyzed per enzyme per second (v) versus substrate concentrations of substrate 1 (FIG. 17A), substrate 2 (FIG. 17B) and substrate 3 (FIG. 17C). The kinetic measurements were carried out at 25° C. in PBS (phosphate buffered saline) buffer at pH 7.4. The absorbance change at 650 nm was measured by means of a UV spectrophotometer.

A solution of β-lactamase (5.0 nM) was added to a series of different concentration of substrates (ranging from 0 to 30 μM). The reaction mixture was then added to a suspension of gold nanoparticles (2.50 nM). The rate of enhancement in absorbance at 650 nm was applied to determine the kinetic properties of enzyme hydrolysis. The values of the kinetic parameters ($K_m$ and $K_{cat}$) were determined from the double-reciprocal plot of the hydrolysis rate versus substrate concentrations (Lineweaver-Burk plot, based on the Michaelis-Menten model). Analysis of the enzymatic kinetics of the three substrates determined a $k_{cat}$=(0.33±0.1) s$^{-1}$ and a $K_m=(140\pm11)$ μm for substrate 1, a $k_{cat}=(8.69\pm1.3)$ s$^{-1}$ and a $K_m=(113\pm8.0)$ μm for substrate 2, and a kcat$_{cat}$ of 22.7 s$^{-1}$ and a $K_m$ of 14.1 μM for substrate 3.

Figure 18:
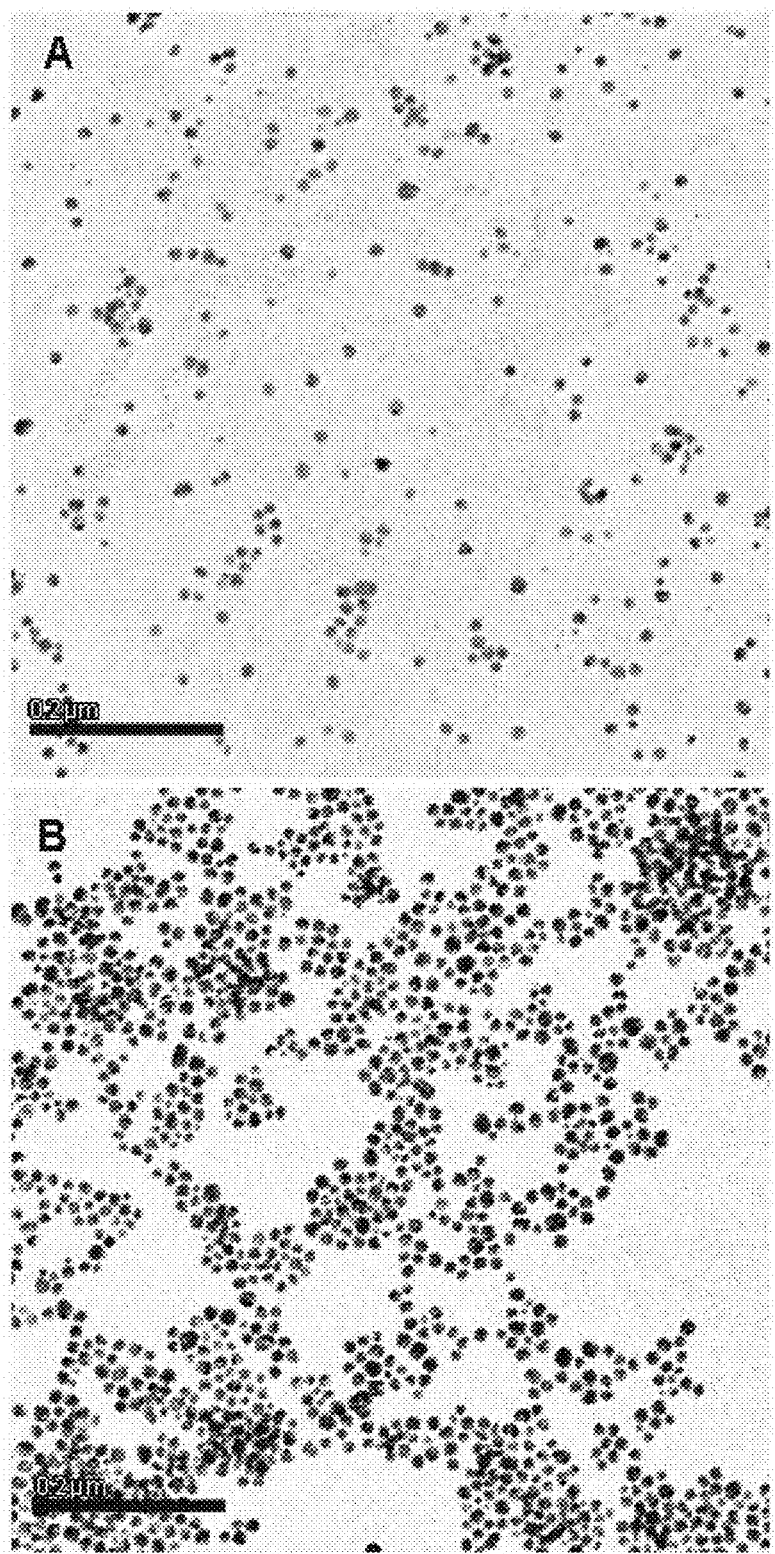
FIG. 18A-B depicts TEM images of substrate 2 in gold nanoparticles only (FIG. 18A) and after incubation of substrate 2 with Bla (5 nm) in a gold nanoparticle solution (FIG. 18B).

FIG. 18 depicts transmission electron microscopy (TEM) images of substrate 2 (8 μM) in gold nanoparticles only (FIG. 18A) and incubation of substrate 2 (8 μM) with Bla (5 nm) in gold nanoparticle solutions (FIG. 18B). Scale bars: 200 nm. As shown in FIG. 15A, substrate 2 itself (8 μm) was unable to induce the aggregation of the gold nanoparticle suspensions. Upon treatment of the same concentration of substrate 2 with Bla (5 nm), the enzyme interaction triggered the release of the modified dithiol linker, thus inducing the cross-linking of the gold nanoparticle and increasing the aggregation dramatically (FIG. 18B). Although some agglomerations could also be detected in FIG. 15A, possibly caused by self-assembly during the drying process in the sample preparation, most of the gold nanoparticles were dispersed randomly in the solution with diameters of approximately 15 nm. Images of the gold nanoparticles were acquired by using a JEOL 2000 EX TEM operating at 200 kV. TEM samples were prepared by the slow evaporation of one drop of an aqueous solution of the particles placed on a carbon-coated copper mesh grid.

Figure 19A:
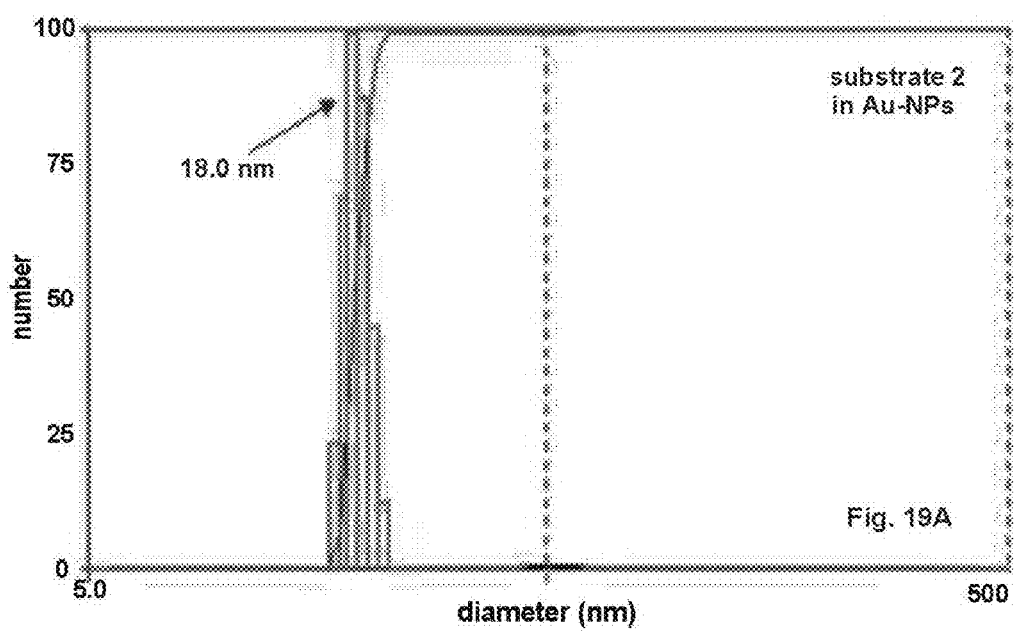
FIG. 19A-B illustrates the size distribution in solution of gold nanoparticles with substrate 2 (FIG. 19A) and with Bla pretreated substrate 2 (FIG. 19B), using dynamic light scattering.
Figure 19B:
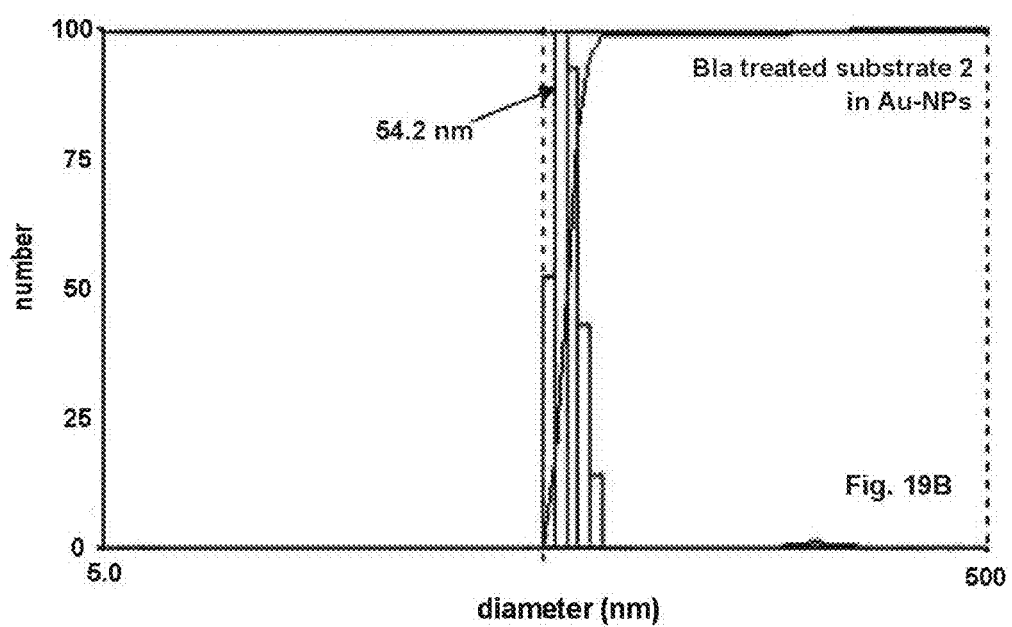

FIG. 19 illustrates the size distribution in solution by means of dynamic light scattering (DLS) measurements of substrate 2 (8 μM) only in gold nanoparticles (FIG. 19A), and Bla pretreated substrate 2 (8 μM) in gold nanoparticles (FIG. 19B). These data confirmed a well-dispersed population of gold nanoparticles in the solution with substrate 2 only (FIG. 19A) and highly aggregated gold nanoparticles in the solution with Bla-pretreated substrate 2 (FIG. 19B). The sizes and size population distributions of gold particles were determined on a Brookhaven Instruments spectrophotometer. Dust-free solution vials were used for the aqueous solutions, and measurements were performed at an angle of 90° under room temperature. The CONTIN algorithm was used for analyze the DLS data. The light scattering measurements clearly indicated the monodispersion of gold nanoparticles in average diameters of 18±2 nm in the solution only treated with substrate 2 and highly aggregated Au-NPs in average diameters of 54.2±4 nm in the solution treated with β-lactamase and substrate 2.

Figure 20:
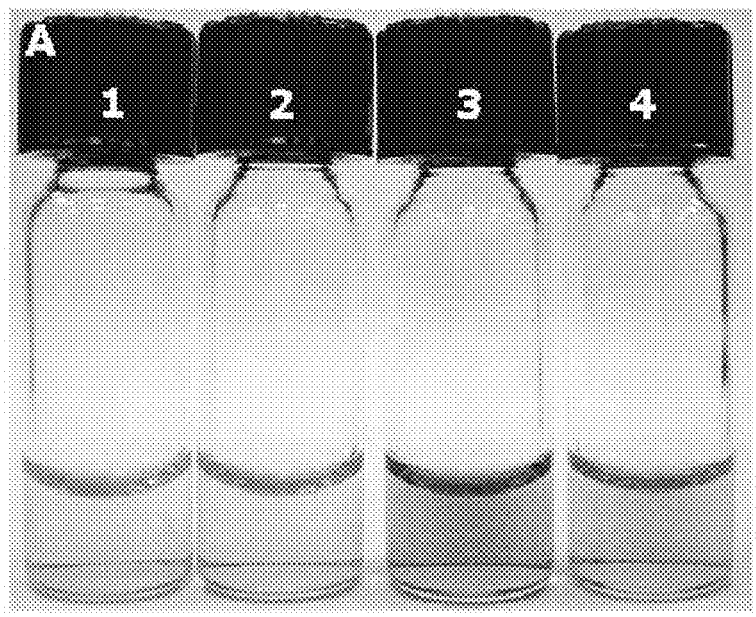
FIG. 20 depicts the coloring of a solution of gold nanoparticles in the absence or presence of different bacterial strains and substrate 2 (1: gold nanoparticles only; 2: nanoparticles+substrate 2 treated with wild-type *E. coli* Bl21; 3: nanoparticles+substrate 2 treated with plasmid-encoded antibiotic-resistant *E. coli* Bl21; 4: nanoparticles+substrate 2 treated with clinically isolated β-lactam-resistant *K. pneumoniae*).

FIG. 20 depicts a colorimetric measurement of the gold nanoparticle aggregation at 30 min after incubation with different bacterial strains (ca. 10$^8$ cfu mL$^{-1}$; cfu=colony-forming units). 1: gold nanoparticles only; 2: substrate 2 (8 μM) treated with wild-type *E. coli* Bl21. 3: substrate 2 treated with antibiotic-resistant plasmid-encoded *E. coli* Bl21; 4: substrate 2 treated with clinically isolated β-lactam-resistant *K. pneumoniae* (ATCC 700603). Substrate 2 treated with wild-type *E. coli* Bl21 does not lead to a color change of gold nanoparticles because it is unable to express Bla. However, significant color change was observed within 30 minutes after adding plasmid-encoded *E. coli* Bl21 or substrate 2 treated with *K. pneumoniae* to the gold nanoparticle suspensions. The different color changes (violet blue in Bla encoded *E. coli* Bl21 and reddish purple in *K. pneumoniae*) were attributed to the different Bla expressions. These two β-lactam-resistant bacterial cells contained different kinds of β-lactamases (ESBLs; TEM-1 in plasmid encoded *E. coli* Bl21 and extended-spectrum β-lactamases (ESBLs) SHV-18 in *K. pneumoniae*; Rasheed, J. K., et al., *Antimicrob. Agents Chemother.* (2000) 44, 2382-2388). The different types of Blas exhibited different enzymatic conversions for the same substrate, which is consistent with results reported recently (Yang, Z. M., et al., *J. Am. Chem. Soc.* (2007) 129, 266-267).

Figure 21:
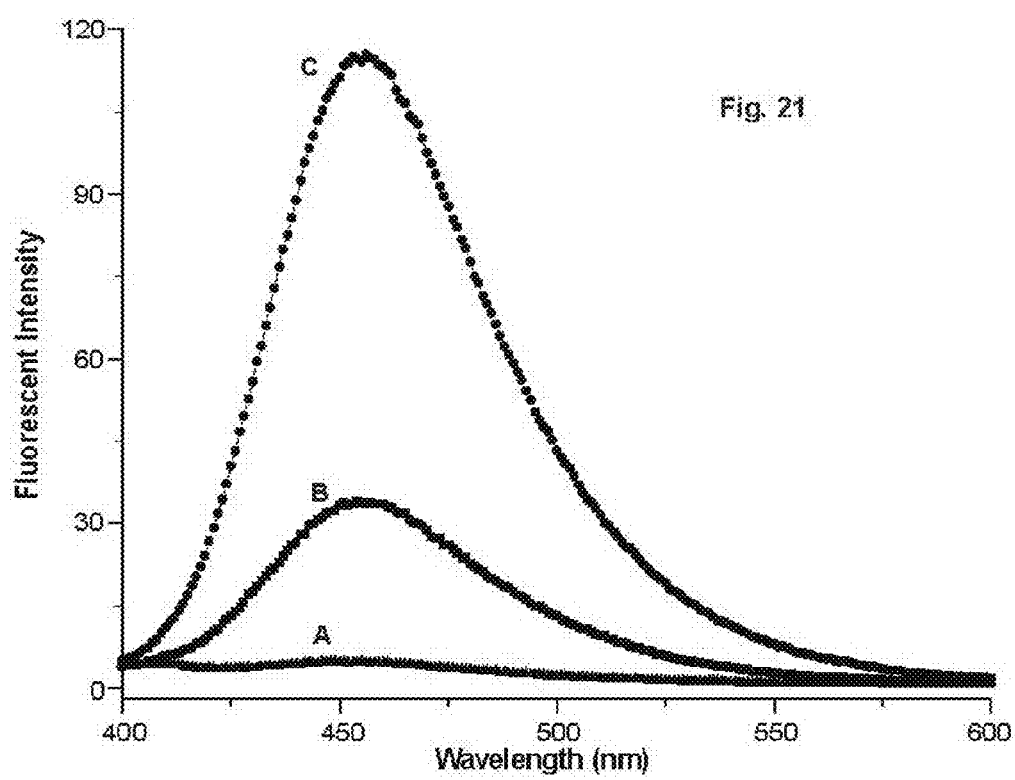
FIG. 21 depicts fluorescent emission of CC1 in wild-type *E. coli* Bl21 (A), *K. pneumoniae* (B), and plasmid-encoded *E. coli* Bl21 (C).

FIG. 21 depicts fluorescent emission ($I_f$) of CC1 (2 μM) in wild-type *E. coli* Bl21 (A), *K. pneumoniae* (B), and plasmid-encoded *E. coli* Bl21 (C). The excitation was measured at 360 nm. No significant fluorescent signal was detected in wild-type *E. coli* Bl21. Emission of CC1 in *E. coli* Bl21 (with Bla) was approximately four times higher than that in *K. pneumoniae*, which confirmed the highest enzyme activity in the Bla-(TEM-1)-encoded *E. coli* Bl21 strains. As a commonly used fluorogenic probe, CC1 was more sensitive in the detection of Blas than was the colorimetric assay. However, CC1 itself was not as stable and spontaneous hydrolysis easily occurred. In addition, the whole fluorescent assay had to be conducted with specific instrumentation, such as with a fluorometer or a fluorescent microscope.

FIG. 22 depicts a colorimetric measurement after mixing nitrocefin with different bacterial suspensions. 1: Nitrocefin solution (8 μM) only; 2: Nitrocefin (8 μM) mixed with wild type *E. coli* Bl21; 3: Nitrocefin (8 μM) mixed with β-lactam antibiotics resistant *E. coli* Bl21; 4: Nitrocefin (8 μM) mixed with clinical isolate *K. pneumoniae* (ATCC 700603) strains. The result indicated that nitrocefin could induce a similar color change from yellow to pink in both of the β-lactam-resistant bacteria. There was no color difference between the Bla-encoded *E. coli* Bl21 and the *K. pneumoniae* strains. Moreover, the pink color was also detected in the wild-type *E. coli* Bl21 bacteria where no β-lactamase was present, which is possibly due to a nonspecific hydrolysis of nitrocefin. Therefore, compared to the nitrocefin-based colorimetric method, the significantly different color change observed in different β-lactam-resistant bacteria and the absence of background activity in wild-type bacterial strains in the colorimetric embodiment of the method of the invention indicate that the latter has a higher reporting threshold than that of the nitrocefin assay.

EXAMPLES

Material and General Methods

Chemicals: 7-Amino-3-chloromethyl 3-cephem-4-carboxylic acid diphenylmethyl ester hydrochloride (ACLH) was provided from Otsuka chemical Co. Ltd. Nitrocefin was purchased from Merck. β-lactam resistant *K. pneumoniae* bacterial strain (ATCC 700603), TEM-1 *E. coli* strain (ATCC 35218) and *Bacillus cereus* strain (ATCC 13061) were purchased from ATCC. TEM-1 β-lactamase, which is the most prevalent plasmid-mediated β-lactamase in gram-negative bacteria, (a class A enzyme) was obtained from Biologics Process Development, CA, USA. P99 β-lactamase (a class C enzyme) was obtained from Sigma-Aldrich. All the other starting materials were obtained from Sigma or Aldrich. Commercially available reagents were used without further purification, unless noted otherwise. The solvents were dried according to regular protocols. All other chemicals were analytical grade or better.

The synthesized compounds were characterized using $^1$H NMR (Bruker Advance 400 MHz) using CDCl$_3$ as the solvent. ESI-MS spectrometric analyses were performed at the Thermo Finnigan LCQ Deca XP Max and transmission electron micrograph on a JEOL 2000 EX TEM. Absorbance spectra were measured on Beckman Coulter DU 800 UV-Vis spectrophotometer. Dynamic light scattering measurement was conducted at 90 Plus particle size analyzer to study the particle size distribution in solution.

Purification and Preparation: Analytical reverse-phase high performance liquid chromatography (HPLC) was performed on Alltima C-18 column (250×3.0 mm) at a flow rate of 1.0 mL/min and semi-preparative HPLC was performed on the similar C-18 column (250×10 mm) at a flow rate of 3 mL/min. An eluting system consisting of A (water with 0.1% TFA) and B (acetonitrile with 0.1% TFA) was used under a linear gradient to elute the products, which was monitored by UV-Visible absorbance at 280 nm. The linear gradient started from 80% solution A and 20% solution B, changed to 20% solution A and 80% solution B in 30 minute and to 0% solution A and 100% solution B in the following 5 minutes, and then back to 80% solution A and 20% solution B in the next 5 minutes.

Example 1

Synthesis and Characterization of Enzyme Substrate 1

The synthesis of enzyme substrate 1 is shown in FIG. 2A and FIG. 2B.

Preparation of 7-(acetylamino)-3-(chloromethyl)-8-oxo-5-thia-1-azabicyclo[4.2.0]oct-2-ene-2-carboxylic acid diphenylmethyl ester (1, CAS-No 1003884-87-4): 7-Amino-3-chloromethyl cephalosporanic acid benzylhydryl ester hydrochloride (ACLH) (451 mg, 1 mmol) was suspended in dichloromethane. Then acetyl chloride (78.5 mg, 1 mmol) was added drop wise into the suspension. Finally 2,6-lutidine (214 mg, 2 mmol) was added into the reaction mixture and the solution was stirred for 2 hrs under nitrogen. After the removal of the solvent on the rotary evaporator, the residue was purified by flash chromatography on silica gel (eluent: ethyl acetate/hexane=1/1) to afford 223.5 mg (yield: 85.4%) of title compound. $^1$H NMR (400 MHz, CDCl$_3$) 7.47-7.45 (m, 2H), 7.41-7.31 (m, 7H), 7.28-7.26 (m, 1H), 6.98 (s, 1H), 5.90 (dd, J=8.9 and 4.92 Hz, 1H), 5.01 (d, J=4.95 Hz, 1H), 4.40 (s, 2H), 3.65 (d, J=18.3 Hz, 1H), 3.51 (d, J=18.3 Hz, 1H), 2.02 (s, 3H). ESI-MS observed [M+H]$^+$: 457.7, calculated: 456.9.

Preparation of 7-(acetylamino)-3-(iodomethyl)-8-oxo-5-thia-1-azabicyclo[4.2.0]oct-2-ene-2-carboxylic acid diphenylmethyl ester (2, CAS-No 1003884-90-9): A mixture of 7-(acetylamino)-3-(chloromethyl)-8-oxo-5-thia-1-azabicyclo[4.2.0]oct-2-ene-2-carboxylic acid diphenylmethyl ester (1, 155 mg, 0.34 mmol) and sodium iodide (253 mg, 1.7 mmol) in 5 mL of acetone was stirred for 1 hr at room temperature. The reaction mixture was concentrated on the rotary evaporator and diluted with 5 mL water. The suspension was extracted with 25 mL of ethyl acetate, and the organic phase was washed with 10% sodium thiosulfate (5 mL×2), brine (5 mL×3) and dried over anhydrous magnesium sulfate. The slightly orange powder 2 (152 mg, 0.45 mmol) was used without further purification.

Preparation of 4-[(triphenylmethyl)thio]-benzeneacetic acid (13, CAS-No 883566-52-7): 2-Mercaptoethylamine hydrochloride (261.4 mg, 2.3 mmol) was added to the solution of chlorotriphenylmethane (557.6 mg, 2 mmol) in 1.0 mL of anhydrous dichloromethane. Then trifluoroacetic acid (TFA, 0.4 mL) was added to afford dark brown solution. The solution was stirred for 2 hrs under nitrogen. The reaction was quenched by 1N NaOH (3 mL). The suspension was extracted with 10 mL of ethyl acetate, and the organic phase was washed with brine (5 mL×3) and dried over anhydrous magnesium sulfate. The solvent was removed and residue was purified by flash chromatography on silica gel (eluent: ethyl acetate/hexane=1/3) to afford 543 mg of the desired product (85%). $^1$H NMR (400 MHz, CDCl$_3$) δ 7.50-7.48 (m, 6H), 7.34-7.26 (m, 6H), 7.25-7.23 (m, 3H), 2.63 (t, J=6.5 Hz, 2H), 2.36 (t, J=6.5 Hz, 2H), ESI-MS: observed [M+Na]$^+$: 342.5, calculated: 319.3.

Preparation of N-[2-[2-(2-aminoethoxy)ethyl]-carbamic acid 1,1-dimethylethyl ester (4, CAS-No 153086-78-3): To a clear solution of compound 3 (150 mg, 0.47 mmol) in anhydrous dichloromethane (1.5 mL) was added iodoacetic anhydride (20.0 mg, 0.56 mmol) at room temperature, followed by N,N-diisopropylethylamine (DIPEA, 106 μL, 0.61 mmol). The reaction mixture was stirred under room temperature for 12 hours. After removing the solvent in vacuum, the residue was applied to flash chromatography on silica gel (eluent: ethyl acetate/hexane=1/8) to afford 80 mg of 4 (70%). $^1$H NMR (400 MHz, CDCl$_3$) δ 7.46-7.45 (m, 15H), 3.63 (s, 2H), 3.10 (dd, J=6.08 Hz and J=12.36 Hz, 2H), 2.45 (t, J=6.2 Hz, 2H). ESI-MS observed [M+Na]$^+$: 510.5, calculated: 487.4.

Preparation of (5): To a cooled (ice bath) and stirred solution of compound 4 (75 mg, 0.154 mmol) in 3.0 mL anhydrous dichloromethane was added N,N-diisopropylethylamine (DIPEA, 25 μL, 0.33 mmol). Then 2,2'-(ethylenedioxy)bis-ethylamine (10 μL, 0.069 mmol) was added drop-wise into this solution. The solution was stirred overnight. The reaction mixture was concentrated on the rotary evaporator. Purification of the crude product by flash chromatography on silica gel (eluent: methanol/dichloromethane=1/20) afforded 50 mg of the desired product (41%). $^1$H NMR (400 MHz, CDCl$_3$) δ 7.38-7.37 (m, 12H), 7.28-7.25 (m, 10H), 7.21-7.20 (m, 8H), 3.81 (t, J=5.48 Hz, 4H), 3.62 (m, 4H), 3.59 (s, 4H), 3.47 (s, 2H), 3.22 (dd, J=7.36 Hz and J=7.32 Hz, 4H), 3.09 (m, 2H), 2.88 (m, 2H), 2.40 (m, 2H) ESI-MS: observed [M+Na]$^+$: 891.1; calculated: 868.1.

Preparation of 6: To a cooled solution of 5 (20 mg, 0.024 mmol) in 350 mL of anhydrous dichloromethane was added trifluoroacetic acid (1 mL) and triisopropylsilane (50 μL) with cooling (ice bath). The mixture was stirred for 1 hr at the same temperature, then the solvent was removed under reduced pressure. The residue was washed with cold hexane (1 mL×3) to afford 15.5 mg of the light yellow crude product. The crude product was used for next step reaction without further purification. The product was added drop-wise to a solution of compound 2 (23.3 mg, 0.051 mmol) in 0.1 mL anhydrous N,N-dimethylformamide (DMF), followed by addition of N,N-diisopropylethylamine (DIPEA, 8.8 μL, 0.05 mmol) and 2,6-lutidine (28 μL, 0.24 mmol). The mixture was stirred at room temperature for 5 hrs. Then, the reaction mixture was diluted with water (5 mL) and extracted by ethyl acetate (10 mL). The organic phase was washed by brine (5 mL) and dried over anhydrous magnesium sulfate. The solvent was removed and the crude product was further purified by RP-HPLC to collect 3.5 mg of compound 6. ESI-MS observed [M+Na]$^+$: 1246.6, calculated: 1223.

Preparation of Substrate 1: A solution of compound 6 (3.0 mg, 0.00245 mmol) was dissolved in 150 μL of anhydrous dichloromethane. Then trifluoroacetic acid (100 μL) and anisole (4.5 μL) were added. The mixture was stirred for 1 hr at the cooled temperature (ice bath). The solvent was removed under reduced pressure. The precipitate was collected and washed with hexane (1 mL×3) and then purified by RP-HPLC to afford 1.3 mg (60%) of substrate 1. ESI-MS observed [M+H]$^+$: 891.6, calculated: 890.2.

Example 2

Synthesis and Characterization of Enzyme Substrate 2

The synthesis of enzyme substrate 2 is shown in FIG. 2C.
Preparation of p-(tritylthio)-aniline (7, CAS-No 22948-03-4): To a solution of chlorotriphenylmethane (557.6 mg, 2 mmol) in 1.5 mL of anhydrous dichloromethane was added 4-aminoithiolphenol (275.4 mg, 2.2 mmol). Then trifluoroacetic acid (TFA, 0.35 mL) was added to afford dark brown solution. The solution was stirred for 2 hrs at ambient temperature under nitrogen. After the removal of the solvent on the rotary evaporator, the residue was quenched by 1N NaOH (3 mL). The suspension was extracted with 10 mL of ethyl acetate, and the organic phase was washed with brine (5 mL×3) and dried over anhydrous magnesium sulfate. The solvent was removed and residue was purified by flash chromatography on silica gel (eluent: ethyl acetate/hexane=1/3) to afford 625 mg of desired product (85%). $^1$H NMR (400 MHz, CDCl$_3$) δ 7.43 (d, J =7.24 Hz, 6 H), 7.28-7.19 (m, 9 H), 6.78 (d, J=8.4 Hz, 2H), 6.35 (d, J=8.4 Hz, 2 H), 3.66 (s, 2 H). ESI-MS: observed [M+H]$^+$: 368.4, calculated: 367.3.

Preparation of 2-iodo-N-[4-[(triphenylmethyl)thio]phenyl]-acetamide (8, CAS-No 1003885-10-6): To a clear solution of compound 7 (150 mg, 0.41 mmol) in anhydrous dichloromethane (1.5 mL) was added iodoacetic anhydride (173 mg, 0.49 mmol) at room temperature, followed by N,N-diisopropylethylamine (DIPEA, 107 µL, 0.61 mmol). The precipitate was formed within 3 minutes. The reaction mixture was stirred under room temperature for 12 hours. After the removal of the solvent in vacuum, the residue was applied to flash chromatography on silica gel (eluent: ethyl acetate/hexane=1/8) to afford 120 mg of title compound (79%). $^1$H NMR (400 MHz, CDCl$_3$) δ 7.44-7.39 (m, 6 H), 7.29-7.18 (m, 12 H), 6.96 (d, J=8.64 Hz, 2 H), 3.82 (s, 2 H). ESI-MS: observed [M+Na]$^+$: 558.3, calculated: 535.4.

Preparation of 9 (CAS-No 1003885-12-8): To a cooled (ice bath) and stirred solution of compound 8 (75 mg, 0.135 mmol) in 3.0 mL anhydrous dichloromethane was added N,N-diisopropylethylamine (DIPEA, 21.7 µL, 0.29 mmol). Then 2,2'-(ethylenedioxy)bis-ethylamine (8.0 µL, 0.055 mmol) was added drop-wise into this solution. The solution became clear after three hours and the reaction mixture was stirred overnight. The solvent was removed in vacuum. Purification of the crude product by flash chromatography on silica gel (eluent: methanol/dichloromethane=1/20) afforded title compound 38.6 mg (73%). $^1$H NMR (400 MHz, CDCl$_3$) δ 7.42-7.40 (m, 12 H), 7.30-7.20 (m, 22H), 6.93 (d, J=8.0 Hz, 4 H), 3.59-3.40 (m, 8H), 3.40 (s, 4H), 2.84 t, J=4.7 Hz, 4 H). ESI-MS: observed [M+H]$^+$: 965.4; calculated: 964.3.

Preparation of 10 (CAS-No 1003885-15-1): To a cooled solution of compound 9 (15 mg, 0.018 mmol) in 350 µL of anhydrous dichloromethane was added trifluoroacetic acid (1 mL) and triisopropylsilane (45 µL) with cooling (ice bath). The mixture was stirred for 1 hr at the same temperature, and then the solvent was removed in vacuum. The residue was washed with cold hexane (1 mL×3) to afford 13 mg of the light yellow crude product. The crude product was used for next step reaction without further purification. The product was added drop-wise to a solution of compound 2 (23 mg, 0.045 mmol) in 0.1 mL anhydrous N, N-dimethylformamide (DMF), followed by addition of N, N-diisopropylethylamine (DIPEA, 7 µL, 0.04 mmol) and 2,6-lutidine (28 µL, 0.24 mmol). The mixture was stirred at room temperature for 5 hrs. Then, the reaction mixture was diluted with water (5 mL) and extracted by ethyl acetate (10 mL). The organic phase was washed by brine (5 mL) and dried over anhydrous magnesium sulfate. The solvent was removed and the crude product was further purified by RP-HPLC to collect 3.0 mg of compound 6. ESI-MS observed [M+Na]$^+$: 1342.5; calculated: 1319.4.

Preparation of Substrate 2 (CAS-No 1003885-17-3): A solution of 10 (3.0 mg, 0.0023 mmol) was dissolved in 150 µL of anhydrous dichloromethane. Then trifluoroacetic acid (150 µL) and anisole (50 µL) was added under the cooling condition (ice bath). The mixture was stirred for 1 hr at the same temperature. The solvent was removed in vacuum. The precipitate was collected, washed with hexane (1 mL×3) and then further purified by RP-HPLC to afford 1.5 mg (66.7%) of the title product. ESI-MS: observed [M+H]$^+$: 988.7: calculated: 987.2.

Example 3

Synthesis and Characterization of Enzyme Substrate 3

The synthesis of enzyme substrate 3 is shown in FIG. 3.

Preparation of 4-[(triphenylmethyl)thio]-benzeneacetic acid (13, CAS-No 883566-52-7): 4-mercaptophenylacetic acid (369.6 mg, 2.2 mmol) was added to the solution of chlorotriphenylmethane (557.6 mg, 2 mmol) in 2.0 mL of anhydrous dichloromethane. The solution was stirred for 2 hrs under nitrogen. The reaction was quenched by 1N NaOH (3 mL). The suspension was extracted with 10 mL of ethyl acetate, and the organic phase was washed with brine (5 mL×3) and dried over anhydrous magnesium sulfate. The solvent was removed and residue was purified by flash chromatography on silica gel (eluent: ethyl acetate/hexane=1/3) to afford 713.4 mg of desired product (87%). $^1$H NMR (400 MHz, CDCl$_3$) δ 7.43-7.40 (m, 6H), 7.26-7.17 (m, 9H), 6.93 (m, 4H), 3.52 (s, 2H) ESI-MS: observed [M+Na]$^+$: 433.6, calculated: 410.5.

Preparation of N-[2-[2-(2-aminoethoxy)ethoxy]ethyl]-carbamic acid 1,1-dimethylethyl ester (14, CAS-No 153086-78-3): 3,6-Dioxaoctyl-1,8-diamine (244 mg, 1.65 mmol) was stirred in dry dichloromethane (1 mL), then di-tert-butyl carbonate (120 mg, 0.55 mmol) in dry dichloromethane (1 mL) was added slowly over 2 hours. The reaction was stirred overnight at room temperature, the solvent evaporated, and the residue purified by column chromatography (silica gel, ethanol:ethyl acetate:triethylamine eluent=5/4/1). The product was obtained as a pale yellow oil (96 mg, 71%). $^1$H-NMR (400 MHz, CDCl$_3$) δ 3.67 (s, 4H), 3.55-3.62 (m, 4H), 3.34-3.40 (m, 2H), 2.94 (t, J=5.2 Hz, 2H), 1.49 (s, 9H). ESI-MS observed [M+Na]$^+$: 271.2, calculated: 248.3.

Preparation of (15): To a cooled (ice bath) and stirred solution of compound 14 (74.4 mg, 0.30 mmol) in 1.0 mL anhydrous dichloromethane was added compound 13 (123.2 mg, 0.30 mmol). Then N,N'-dicyclohexylcarbodiimide (123.6, 0.30 mmol) in dry dichloromethane (1 mL) was added slowly over 2 hours. The solution was stirred overnight. The reaction mixture was concentrated on the rotary evaporator. Purification of the crude product by flash chromatography on silica gel (eluent: methanol/dichloromethane=5/95) afforded the desired product 65.8 mg (60%). $^1$H NMR (400 MHz, CDCl$_3$) δ 7.41-7.38 (m, 6H), 7.27-7.15 (m, 9H), 6.91 (m, 4H), 3.52-3.49 (m, 8H), 3.42-3.27 (m, 4H), 3.27 (m, 2H), 1.43 (m, 9H) ESI-MS: observed [M+Na]$^+$: 663.7; calculated: 640.8.

Preparation of (16): To a cooled solution of compound 15 (43.8 mg, 0.12 mmol) in 0.5 mL of anhydrous dichloromethane was added trifluoroacetic acid (1 mL) and triisopropylsilane (80 µL) with cooling (ice bath). The mixture was stirred for 1 hr at the same temperature, then the solvent was removed under reduced pressure. The residue was washed with cold hexane (1 mL×3) to afford 25.6 mg of the light yellow crude product. The crude product was used for next step reaction without further purification. The product was added drop-wise to a solution of compound 2 (82.3 mg, 0.051, 0.15 mmol) in 0.5 mL anhydrous N, N-dimethylformamide (DMF), followed by addition of N, N-diisopropylethylamine (DIPEA, 26.4 µL, 0.15 mmol) and 2,6-lutidine (84 µL, 0.72 mmol). The mixture was stirred at room temperature for 5 hrs. Then, the reaction mixture was diluted with water (5 mL) and extracted by ethyl acetate (10 mL). The organic phase was washed by brine (5 mL) and dried over anhydrous magnesium sulfate. The solvent was removed and the crude product was further purified by RP-HPLC to collect 8.9 mg of compound 6. $^1$H NMR (400 MHz, CDCl$_3$) δ 7.41-7.28 (m, 10H), 7.13 (d, J=8.0 Hz, 2H), 7.06 (d, J=8.0 Hz, 2H), 6.80 (s, 1H), 5.74 (dd, J=8.9 and 4.92 Hz, 1 H), 4.93 (m, 3H), 4.07 (d, J=13.2 Hz, 1H), 3.75 (d, J=13.2 Hz, 1H), 3.63-3.52 (m, 12H), 3.46 (m, 2H), 3.05 (m, 2H), 2.06 (s, 3H). ESI-MS observed [M+Na]$^+$: 1246.6, calculated: 1223.

Preparation of Substrate 3: A solution of compound 16 (3.5 mg, 0.0049 mmol) was dissolved in 150 µL of anhydrous dichloromethane. Then trifluoroacetic acid (200 µL) and anisole (9.0 µL) were added. The mixture was stirred for 1 hr at the cooled temperature (ice bath). The solvent was removed under reduced pressure. The precipitate was collected and washed with hexane (1 mL×3) and then purified by RP-HPLC to afford 1.8 mg (65%) of the title product. ESI-MS observed [M+H]$^+$: 891.6, calculated: 890.2.

Example 4

Citrate-Coated Gold Nanoparticles

Gold nanoparticles (15 nm) were prepared by citrate reduction of chloroauric acid, HAuCl$_4$ (see Turkevich, J., et al., *J. Discuss. Faraday Soc.* (1951) 11, 55-75). 2.5×10$^{-5}$ mol of HAuCl$_4$ are dissolved in 95 ml of deionized water. The aqueous solution of HAuCl$_4$ (100 ml, 0.25 mM) was refluxed for 5-10 min. Under vigorous stirring, 5 ml of 0.5% sodium citrate solution was added quickly and reflux was continued for another 30 min until the color of the solution would change gradually from faint yellowish to wine-red. Water was added to the solution as necessary to maintain the volume at 100 ml. Subsequently the pH value was adjusted to 7.4 by diluted NaOH and filtration was carried out through a 0.45 µM Millipore syringe to remove the precipitate. The filtrate was stored at room temperature.

Example 5

Quantitative Analysis of β-Lactamase Induced Gold Nanoparticle Aggregation

1. Enzyme Hydrolysis of Substrate 2 by β-Lactamase (Bla)
Substrate solutions were prepared in deionized water and Bla was dissolved in PBS buffer (pH 7.4). Then Bla solution (10 µl) was mixed with substrates (190 µl) for the enzyme interactions. The final substrate concentrations were maintained at 8.0 µM. The enzymatic reaction was performed by incubating the different Bla concentrations with substrates for 20 min at room temperature. All the tests were performed in triplates. Finally, the substrate solution was added into a suspension of gold nanoparticles to induce the aggregation of gold nanoparticles. In some experiments the absorbance change at 650 nm was analyzed every 10 seconds for 30 min at room temperature by Beckman Coulter DU 800 UV-Vis spectrophotometer.

The color appearance of the gold nanoparticle suspensions with different β-lactamase concentrations is shown in FIG. 7. The effect of different concentrations of substrate 2 is shown in FIG. 8.

2. Changes in Color and UV-Vis Absorption of Gold Nanoparticles after Enzyme Treatment
After 20 min enzyme treatment, the resulting substrate solution was mixed with a suspension of gold nanoparticles (15 nm, 800 µL). The pictures were captured at intervals of every 2 minutes in order to detect color changes of gold nanoparticles. UV-Vis spectra were also collected at different time intervals after mixing the enzyme-treated substrates with gold nanoparticles. As a control, a suspension of gold nanoparticles (800 µL) was mixed with 200 µL DI water, and the color as well as the UV-Vis spectrum of the suspension was analyzed following the same procedure. The color of the gold nanoparticle suspension alone, with substrates 1 and 2, and with Bla treated substrates 1 and 2 with time is depicted in FIG. 5A. The change of UV/Vis spectra with time for Bla treated substrate 2 is shown in FIGS. 5B and 5C.

3. Kinetics of Gold Nanoparticles Based Colorimetric Enzymatic Assay
The kinetic experiments were carried out at 25° C. in PBS buffer with pH 7.4. The absorbance change at 650 nm was measured using a UV spectrophotometer. To a series of different concentration of substrates (range from 160 to 20 µM) were added a solution of β-lactamase. The reaction mixture was then added into suspensions of gold nanoparticles (2.6 nM). The rate of enhancement in absorbance at 650 nm was applied to determine the kinetic properties of enzyme hydrolysis. The 9 values of the kinetic parameters ($K_m$ and $K_{cat}$) were determined from the double-reciprocal plot of the hydrolysis rate versus substrate concentrations (Lineweaver-Burk plot). FIG. 17 depicts the obtained results for substrates 1-3.

4. Colorimetric Assay by Using β-Lactamase, Inhibitors and Nitrocefin
Various β-lactamase inhibitors (40 µM) were mixed with Bla (2.0 nM) solution first. Then the mixture was incubated at room temperature for 10 minutes to inhibit Bla activity. The inhibitor solution pre-treated with Bla was added into nitrocefin solution. The final concentration of nitrocefin was maintained at 40 µM. After 3 mins interaction the solution was applied for colorimetric image. The observed absorbance changes at 482 nm and 620 nm using substrate 3 are depicted in FIGS. 10A and 10B. FIG. 11 depicts the corresponding color change.

Example 6

Inhibition Assay for β-Lactamase Activity by Using Gold Nanoparticles

For the inhibition assay of β-lactamase activity using substrate 1 and 2, the procedure is the same as that in the enzyme reaction for aggregation of gold nanoparticles. The final concentration of β-lactamase was maintained at 5.0 nM. The substrate concentrations were ranged from 4 to 12 µM. Various β-lactamase inhibitors (0.25 µM, pH 7.4) were mixed with Bla solution first, were applicable. Then the mixture was incubated at room temperature for 10 minutes to inhibit β-lactamase activity. Finally, the substrate solution with inhibitor pre-treated β-lactamase was added into the gold nanoparticle suspension to induce the aggregation of gold nanoparticles. The absorbance change at 650 nm was analyzed every 10 seconds for 30 min at room temperature by Beckman Coulter DU 800 UV-Vis spectrophotometer.

FIG. 6 shows the measured absorbance change at 650 nm with substrate 2 and the inhibitor sulbactam.

In a further set of experiments substrate 3 was used at a final concentration of 8.0 μM and β-lactamase solutions at a final concentration of 2.0 nM. A commonly used β-lactamase inhibitor; sulbactam (10 μL in PBS buffer, pH 7.4) was mixed with β-lactamase solution (10 μL in PBS, pH 7.4) first. Then the mixture was incubated at room temperature for 20 minutes to inhibit Bla activity. The inhibitor pre-treated β-lactamase solution was added into 180 μL solution of substrate for the further enzyme interactions. Finally, after 20 min incubation, 200 μL of the substrate solution (with inhibitor pre-treated β-lactamase) was added into 800 μL of gold nanoparticles suspension to induce the aggregation of gold nanoparticles. The absorbance change at 650 nm was analyzed every 3 min for 30 min at room temperature by Beckman Coulter DU 800 UV-Vis spectrophotometer. The observed absorbance change at 482 nm is depicted in FIG. 9.

Example 7

Transmission Electron Microscopy (TEM) for Size Distribution

Images of the gold nanoparticles were acquired by using a JEOL 2000 EX TEM operating at 200 kV. TEM samples were prepared by the slow evaporation of one drop of an aqueous solution of the particles placed on a carbon-coated copper mesh grid. Images of gold nanoparticles in presence of substrate 2 with and without β-lactamase are shown in FIG. 18.

Example 8

Dynamic Light Scattering (DLS) for Size Distribution in Solution

The sizes and size population distributions of gold particles in substrate 2 (8 μM) treated suspensions of gold nanoparticles and β-lactamase pretreated substrate 2 (8 μM) suspensions of gold nanoparticles were determined on a Brookhaven Instruments spectrophotometer. Dust-free solution vials were used for the aqueous solutions, and measurements were performed at an angle of 90° under room temperature. The CONTIN algorithm was used for analyze the DLS data. The light scattering measurements clearly indicated the monodispersion of gold nanoparticles in average diameters of 18±2 nm in the solution only treated with substrate 2 and highly aggregated gold nanoparticles in average diameters of 54.2±4 nm in the solution treated with β-lactamase and substrate 2.

FIG. 19 shows an example of obtained size distribution data using substrate 2.

Example 9

β-Lactamase Activity in β-Lactam Antibiotics Resistant Bacterial Strains

β-lactam antibiotics resistant gene encoding E. coli Bl21 and clinical isolate K. pneumoniae (ATCC 700603) strains were grown at 37° C. in LB broth (Fischer). When the optical density (OD) at 600 nm reached 0.8, the suspension was chilled on ice for 5 min, 1 ml aliquots were taken into 1.5 mL vial, and bacteria were harvested by centrifugation at 10,000 rpm for 5 min. After centrifugation, supernatant was removed and cells were washed three times with 1 mL of PBS (approximately $1\times10^8$ cfu/mL). The bacterial cells were then re-suspended in 2.5 mL deionized water for CC1 assay (Gao, W. Z., et al., J. Am. Chem. Soc (2003) 125, 11146-11147). Fluorogenic substrate CC1 was prepared according the literature (ibid.) 5 μl of CC1 (1 mM in PBS, pH 7.4) was added into 2.5 mL of bacteria suspensions, Fluorescence spectra were recorded on Varian Cary Eclipse fluorescence spectrophotometer. The excitation wavelength was 360 nm and 10 nm of slit was used for detection. The enhancement of fluorescent signal at 450 nm was detected every ten minutes until no any further fluorescence increase. In contrast, wild type E. coli Bl21 strains without β-lactam resistant gene 11 were also used as negative control. The different fluorescent signal in wild type E. coli Bl21, β-lactam antibiotics resistant E. coli Bl21 and clinical isolate K. pneumoniae (ATCC 700603) strains were recorded at the same conditions. Fluorescent emission data are shown in FIG. 21.

Example 10

Aggregation Test with Gold Nanoparticles in Living E. coli Cells

Bacterial cells (~$10^8$ cfu/mL) were suspended in 200 μl of deionized water which contained substrates under the room temperature. The suspension was incubated for 20 minutes for further enzyme interactions. After centrifugation, supernatant was applied for colorimetric image. The 200 μl of the bacterial solution was added into 800 μl of gold nanoparticles suspension to induce the aggregation of gold nanoparticles. The color change of the gold nanoparticles was recorded at different time intervals. FIG. 20 shows the color change of gold nanoparticles using substrate 2.

Example 11

Colorimetric Assay by Using Standard β-Lactamase Indicator, Nitrocefin in Living Bacteria Bacterial cells (~$10^8$ cfu/mL) were suspended in 1 ml of PBS buffer (pH 7.4) which contained substrates under the room temperature. Nitrocefin solution (from Merck) was incubated with bacteria for further enzyme interactions. The final concentration was maintained at 8 μM, which was the same as the gold nanoparticles based enzymatic assay. After 20 mins interaction and followed by centrifugation, supernatant was applied for colorimetric image. The color change with different bacterial suspensions is depicted in FIG. 22.

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:
1. A compound of one of general formula (I):

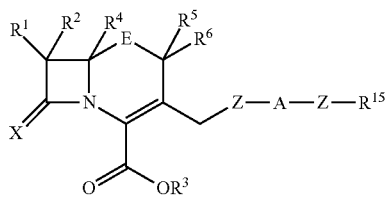

general formula (II):

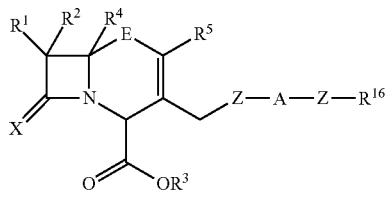

general formula (III):

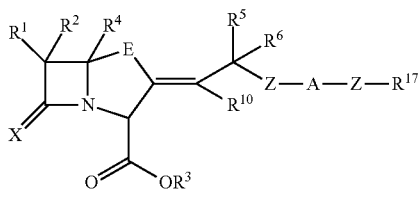

general formula (VII):

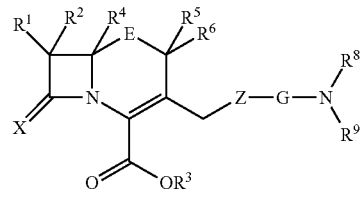

general formula (VIII):

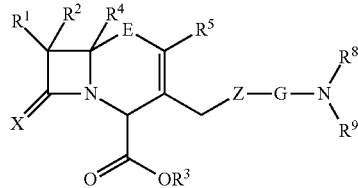

and general formula (IX):

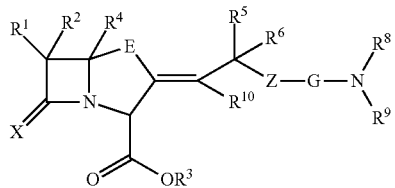

wherein $R^1$ is selected from the group consisting of H, halogen and

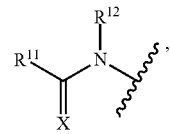

wherein X is one of O, S, Se and NH,
and $R^{11}$ and $R^{12}$ are independently from each other H or selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si;
$R^2$ is one of H, halogen, an aliphatic group, an alicyclic group, an aromatic group, an arylaliphatic group and an arylalicyclic group, comprising 0 to about 3 heteroatoms selected from the group consisting of N, O, S, Se and Si;
$R^3$ to $R^5$, in formulas (I), (III), (VII) and (IX) $R^6$, in formulas (VII)-(IX) $R^8$ and $R^9$, and in formulas (III) and (IX) $R^{10}$, are independently from each other selected H or one of an aliphatic group, an alicyclic group, an aromatic group, an arylaliphatic group and an arylalicyclic group, comprising 0 to about 3 heteroatoms selected from the group consisting of N, O, S, Se and Si;
$R^{15}$ in formula (I), $R^{16}$ in formula (II) and $R^{17}$ in formula (III) are independently selected from H or one of an aliphatic group, an alicyclic group, an aromatic group, an arylaliphatic group and an arylalicyclic group, including 0 to about 5 heteroatoms selected from the group consisting of N, O, S, Se and Si;
X is one of O, S, Se and NH;
E is one of S, SO, $SO_2$, and $CH_2$;
Z is S or Se; and
A in formulas (I)-(III) and G in formulas (VII)-(IX) are independently from each other a bridge selected from an aliphatic, alicyclic, aromatic, arylaliphatic, and arylalicyclic radical with a main chain of 1-50 carbon atoms and 0-50 heteroatoms;

with the proviso that, where in formula (I) R$^{15}$ is

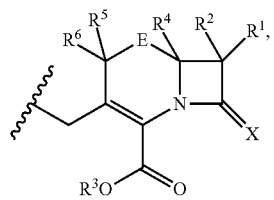

from the bridge A of the compounds of formulas (I) and (II) the following group is excluded:

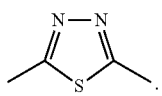

2. The compound of claim 1, wherein R$^{15}$ in formula (I), R$^{16}$ in formula (II) and R$^{17}$ in formula (III) are independently selected from one of the bicyclic moieties (IV)-(VI):

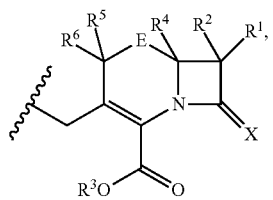

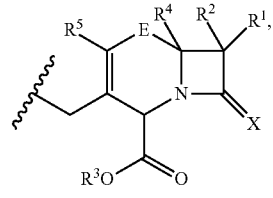

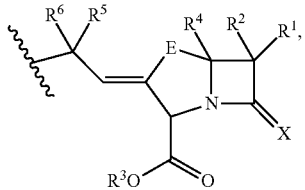

wherein in formulas (IV) and (VI) R$^6$ is selected from H or one of an aliphatic group, an alicyclic group, an aromatic group, an arylaliphatic group and an arylalicyclic group, comprising 0 to about 3 heteroatoms selected from the group consisting of N, O, S, Se and Si.

3. The compound of claim 2, comprising two identical bicyclic moieties, wherein R$^{15}$ in formula (I) is the bicyclic moiety (IV), R$^{16}$ in formula (II) is the bicyclic moiety (V) and R$^{17}$ in formula (III) is the bicyclic moiety (VI).

4. The compound of claim 1, wherein the bridge A in formulas (I)-(III) and the bridge G in formulas (VII)-(IX) comprise the structure J-Q-M,
   wherein J and M are independent from each other an aliphatic spacer with a main chain of 0 to about 10 carbon atoms and 0- about 3 heteroatoms selected from the group consisting of N, O, S, Se and Si, and
   wherein Q is an aliphatic or an alicyclic radical with a main chain of 1 to about 50 carbon atoms and 0 to about 50 heteroatoms selected from the group consisting of N, O, S, Se and Si.

5. The compound of claim 4, wherein the bridge A in formulas (I)-(III) and the bridge G, in formulas (VII)-(IX) comprise the structure ar-J-Q-M-ar,
   wherein ar is an aromatic radical.

6. The compound of claim 4, wherein J and M are identical.

7. The compound of claim 4, wherein the bridge G in formulas (VII)-(IX) comprises the structure ar-J-Q-M,
   wherein ar is an aromatic radical.

8. The compound of claim 1, wherein the main chain of the bridge A in formulas (I)-(III) and of the bridge G in formulas (VII)-(IX) comprise an amide bond.

9. The compound of claim 1, wherein the bridge A of formulas (I)-(III) is selected from the group consisting of a polymer of one of formulas (XXXX) to (XXXXVI);

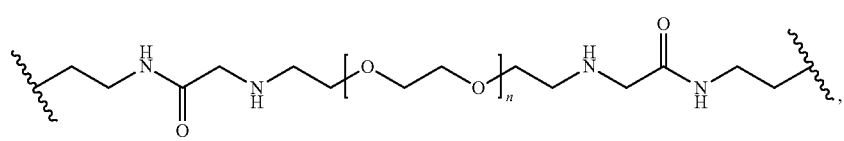

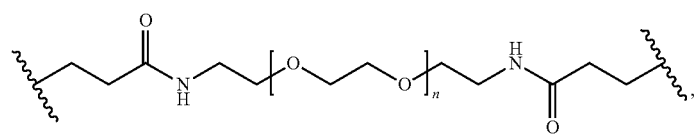

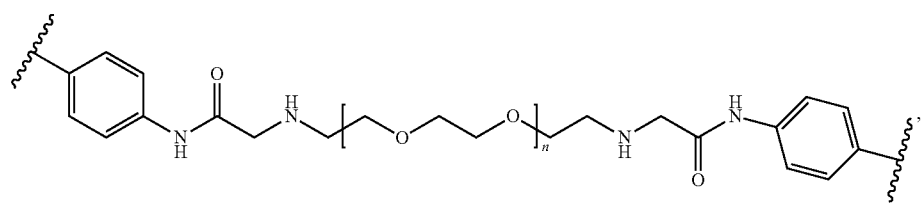

-continued (XXXXIII)
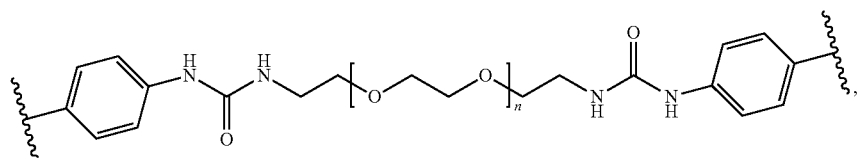

(XXXXIV)
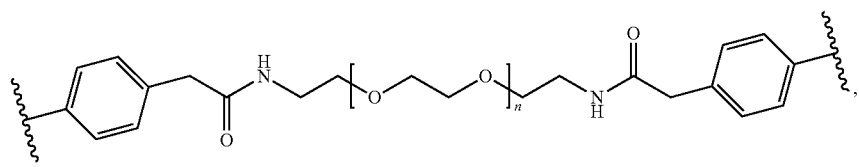

(XXXXV)
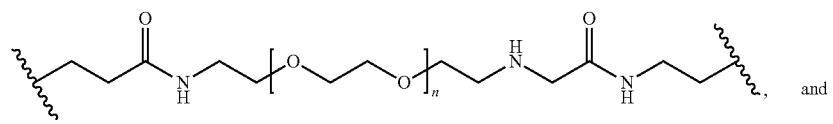

(XXXXVI)
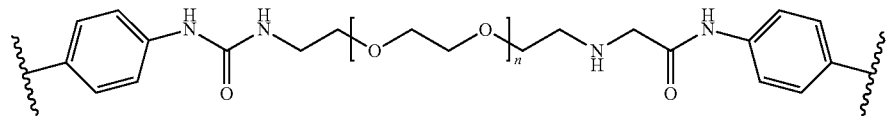

wherein in formulas (XXXX) to (XXXXVI) n is an integer from 0 to 20.

10. The compound of claim 1, wherein the bridge G of formulas (VII)-(IX) is selected from the group consisting of a polymer of one of formulas (XXXXVII)-(XXXXVIIII), and (LXII) to (LXIV):

(XXXXVII)
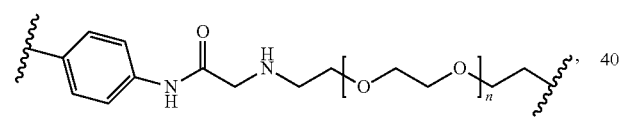

(XXXXVIII)
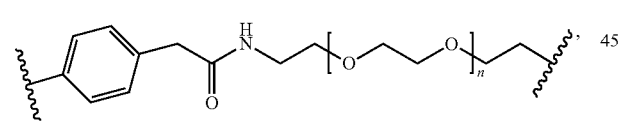

(XXXXVIIII)
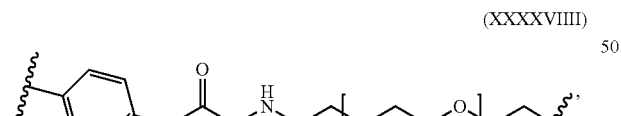

(LXII)
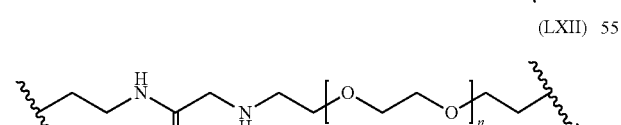

(LXIII)
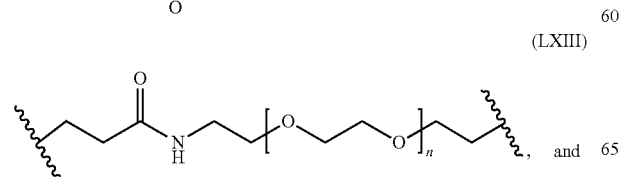

-continued (LXIV)
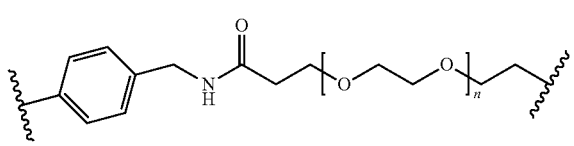

wherein in formulas (XXXXVII)-(XXXXVIIII) and (LXII) to (LXIV) n is an integer from 0 to 20.

11. A method of forming a compound of one of general formulas (I)-(III)

(I)
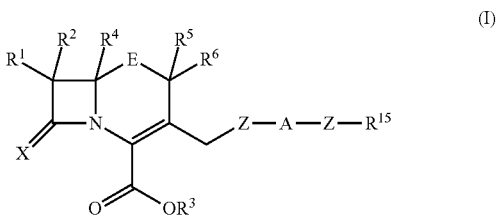

(II)
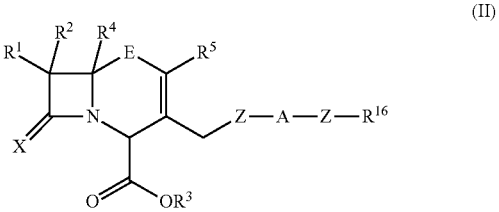

(III)

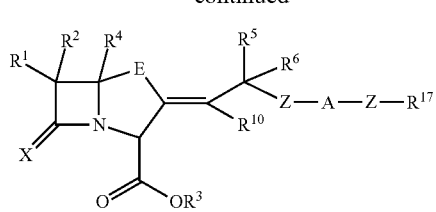

wherein R¹ is selected from the group consisting of H, halogen and

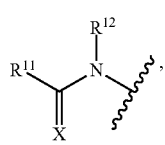

wherein X is one of O, S, Se and NH, and R¹¹ and R¹² are independently from each other H or selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si;

R² is one of H, halogen, an aliphatic group, an alicyclic group, an aromatic group, an arylaliphatic group and an arylalicyclic group, comprising 0 to about 3 heteroatoms selected from the group consisting of N, O, S, Se and Si;

R³ to R⁵, in formulas (I) and (III) R⁶, and in formula (III) R¹⁰ are independently from each other selected H or one of an alicyclic group, an aromatic group, an arylaliphatic group and an arylalicyclic group, comprising 0 to about 3 heteroatoms selected from the group consisting of N, O, S, Se and Si;

R¹⁵ in formula (I), R¹⁶ in formula (II) and R¹⁷ in formula (III) are independently selected from H or one of an aliphatic group, an alicyclic group, an aromatic group, an arylaliphatic group and an arylalicyclic group, including 0 to about 5 heteroatoms selected from the group consisting of N, O, S, Se and Si;

Z is S or Se;

X is one of O, S, Se and NH; and

A is a bridge selected from an aliphatic, alicyclic, aromatic, arylaliphatic, and arylalicyclic radical with a main chain of 1-50 carbon atoms and 0-50 heteroatoms;

the method comprising reacting a compound of one of general formulas (XX), (XXX) and (XXXI):

(XX)

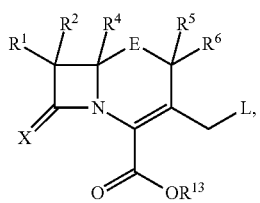

(XXX)

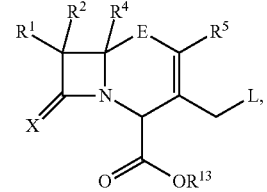

(XXXI)

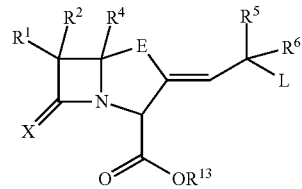

wherein L is a suitable leaving group,

R⁶ in formulas (XX) and (XXXI) is H or one of an aliphatic group, an alicyclic group, an aromatic group, an arylaliphatic group and an arylalicyclic group, comprising 0 to about 3 heteroatoms selected from the group consisting of N, O, S, Se and Si; and R¹³ is selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si, with a compound of general formula R¹⁴—Z-A-Z—R¹⁴ (L)

wherein R¹⁴ in formula (L) is selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si.

12. The method of claim 11, wherein the leaving group L is selected from the group consisting of halogen, cyano, thiocyano, trifluoromethyl sulfonyl, p-toluenesulfonyl, bromobenzenesulfonyl, nitrobenzenesulfonyl, methanesulfonyl and azido.

13. A method of forming a compound of one of general formulas (VII) to (IX):

(VII)

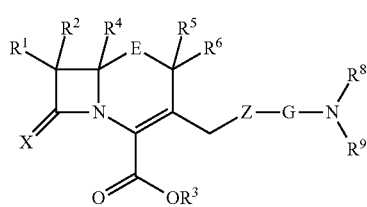

(VIII)

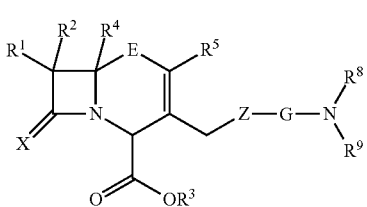

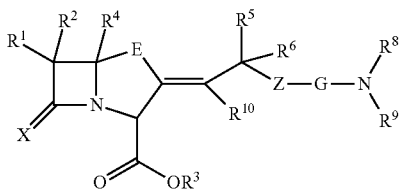

(IX)

wherein R¹ is selected from the group consisting of H, halogen and

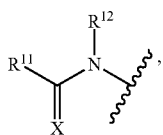

wherein X is one of O, S, Se and NH,
and R¹¹ and R¹² are independently from each other H or selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si;

R² is one of H, halogen, an aliphatic group, an alicyclic group, an aromatic group, an arylaliphatic group and an arylalicyclic group, comprising 0 to about 3 heteroatoms selected from the group consisting of N, O, S, Se and Si;

R³ to R⁵, in formulas (VII) and (IX) R⁶, R⁸ and R⁹ are independently from each other H or selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si;

E is one of S, SO, SO₂, and CH₂;

X is one of O, S, Se and NH;

Z is S or Se; and

G is a bridge selected from an aliphatic, alicyclic, aromatic, arylaliphatic, and arylalicyclic radical with a main chain of 1-50 carbon atoms and 0-50 heteroatoms;

the method comprising reacting a compound of one of general formulas (XX), (XXX) and (XXXI):

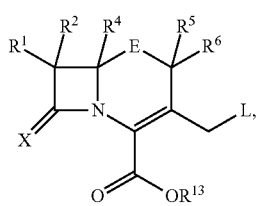

(XX)

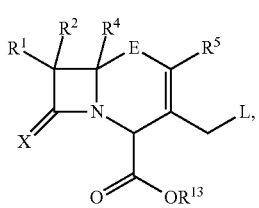

(XXX)

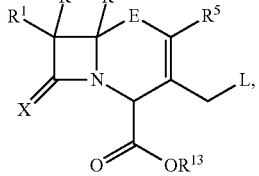

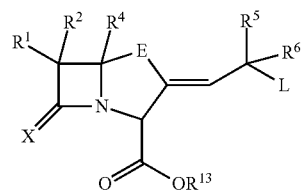

(XXXI)

wherein L is a suitable leaving group,

R¹³ is selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si, R⁶ in formulas (XX) and (XXXI) is H or one of an aliphatic group, an alicyclic group, an aromatic group, an arylaliphatic group and an arylalicyclic group, comprising 0 to about 3 heteroatoms selected from the group consisting of N, O, S, Se and Si, and X is one of O, S, Se and NH;

with a compound of general formula (LII)

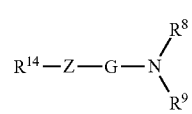

(LII)

wherein R⁸ and R⁹ are independently from each other selected H or one of an aliphatic group, an alicyclic group, an aromatic group, an arylaliphatic group and an arylalicyclic group, comprising 0 to about 3 heteroatoms selected from the group consisting of N, O, S, Se and Si; and R¹⁴ is selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si.

14. The method of claim 13, wherein the leaving group L is selected from the group consisting of halogen, cyano, thiocyano, trifluoromethyl sulfonyl, p-toluenesulfonyl, bromobenzenesulfonyl, nitrobenzenesulfonyl, methanesulfonyl and azido.

15. A kit for detecting beta-lactamase activity in a sample, the kit comprising:

a compound of one of general formulas (I)-(III) and (VII)-(IX):

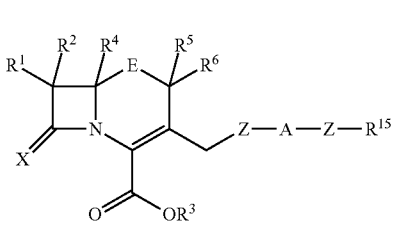

(I)

-continued

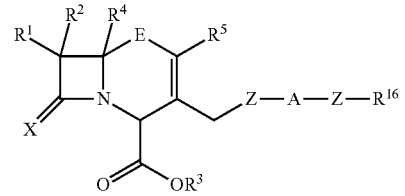 (II)

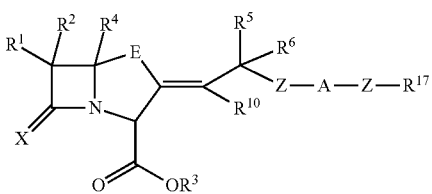 (III)

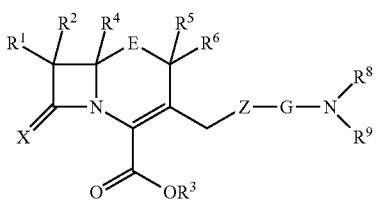 (VII)

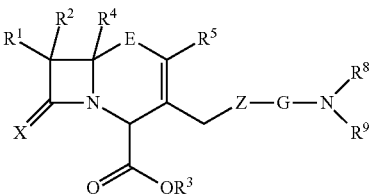 (VIII)

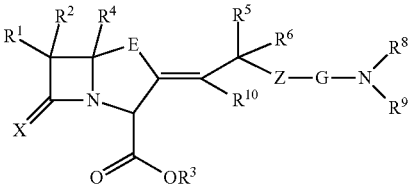 (IX)

wherein $R^1$ is selected from the group consisting of H, halogen and

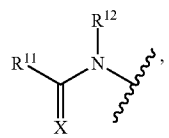

wherein X is one of O, S, Se and NH,
and $R^{11}$ and $R^{12}$ are independently from each other H or selected from the group consisting of an aliphatic group, an alicyclic group, an aromatic group, an arylaliphatic group, and an arylalicyclic group, comprising 0 to about 3 heteroatoms selected from the group consisting of N, O, S, Se and Si;

$R^2$ is one of H, halogen, an aliphatic group, an alicyclic group, an aromatic group, an arylaliphatic group and an arylalicyclic group, comprising 0 to about 3 heteroatoms selected from the group consisting of N, O, S, Se and Si;

$R^3$ to $R^5$, to $R^5$, in formulas (I), (III), (VII) and (IX) $R^6$, in formulas (VII)-(IX) $R^8$ and $R^9$, and in formulas (III) and (IX) $R^{10}$, are independently from each other selected H or one of an aliphatic group, an alicyclic group, an aromatic group, an arylaliphatic group and an arylalicyclic group, comprising 0 to about 3 heteroatoms selected from the group consisting of N, O, S, Se and Si;

$R^{15}$ in formula (I), $R^{16}$ in formula (II) and $R^{17}$ in formula (III) are independently selected from H or one of an aliphatic group, an alicyclic group, an aromatic group, an arylaliphatic group and an arylalicyclic group, including 0 to about 5 heteroatoms selected from the group consisting of N, O, S, Se and Si;

X in formulas (III) and (IX) is one of O, S, Se and NH;

E is one of S, SO, $SO_2$, and $CH_2$;

Z is S or Se; and

A in formulas (I)-(III) and G in formulas (VII)-(IX) are independently from each other a bridge selected from an aliphatic, alicyclic, aromatic, arylaliphatic, and arylalicyclic radical with a main chain of 1-50 carbon atoms and 0-50 heteroatoms; and a nanoparticulate tag.

16. The kit of claim 15, further comprising:

means for determining the presence of beta-lactamase activity based on the presence of the cleavage moiety Z-A-Z, Z-A-Z—$R^{15}$, Z-A-Z—$R^{16}$, Z-A-Z—$R^{17}$, Z-A-Z—$R^{18}$ and Z-G-N($R^8$)$R^9$, respectively, immobilized onto the surface of the nanoparticulate tag.

* * * * *